US012690808B1

(12) United States Patent
Lukyanchikov et al.

(10) Patent No.: US 12,690,808 B1
(45) Date of Patent: Jul. 28, 2026

(54) NEUROLOGICAL EXAMINATION SYSTEM

(71) Applicant: RemNeuro, L.L.C., West Jordan, UT (US)

(72) Inventors: Nikolay Lukyanchikov, Salt Lake City, UT (US); Christian Andrew Balbin, Salt Lake City, UT (US); Olivia May Snyder, Salt Lake City, UT (US); Carson Walter Irving Moore, North Salt Lake, UT (US)

(73) Assignee: RemNeuro, L.L.C., West Jordan, UT (US)

( * ) Notice: Subject to any disclaimer, the term of this patent is extended or adjusted under 35 U.S.C. 154(b) by 0 days.

(21) Appl. No.: 19/080,513

(22) Filed: Mar. 14, 2025

Related U.S. Application Data

(60) Provisional application No. 63/694,658, filed on Sep. 13, 2024, provisional application No. 63/575,624, (Continued)

(51) Int. Cl.
*A61B 5/00* (2006.01)
*A61B 5/12* (2006.01)
(Continued)

(52) U.S. Cl.
CPC ............ *A61B 5/483* (2013.01); *A61B 5/0051* (2013.01); *A61B 5/125* (2013.01); *A61B 5/224* (2013.01);
(Continued)

(58) Field of Classification Search
CPC ..... A61B 5/4827; A61B 5/483; A61B 5/0048; A61B 5/0051; A61B 5/121; A61B 5/125;
(Continued)

(56) References Cited

U.S. PATENT DOCUMENTS 4,949,729 A * 8/1990 Haski ..................... A61B 5/225
600/595
6,575,575 B2 * 6/2003 O'Brien ............... A61B 3/0033
351/245
(Continued)

FOREIGN PATENT DOCUMENTS

CN 107468478 A * 12/2017 ............. A61G 13/08
FR 3041876 A1 * 4/2017 .......... A61G 15/125
WO WO-2016016410 A1 * 2/2016 .......... A61B 5/4824

OTHER PUBLICATIONS

G. V. Kondraske, A. R. Potvin, W. W. Tourtellotte and K. Syndulko, "A Computer-Based System for Automated Quantitation of Neurologic Function," in IEEE Transactions on Biomedical Engineering, vol. BME-31, No. 5, pp. 401-414, May 1984, doi: 10.1109/TBME.1984.325279. (Year: 1984).*

(Continued)

*Primary Examiner* — John R Downey
(74) *Attorney, Agent, or Firm* — Lowenstein Sandler LLP

(57) ABSTRACT

A system includes a patient placement module configured to receive a patient, one or more arms connects to the patient placement module, and two or more assessment module devices. Each of the two or more assessment module devices is connected to a respective arm of the one or more arms. Each of the two or more assessment module devices is configured to provide a respective set of assessment data of a variety of sets of assessment data associated with a neurological examination of the patient.

20 Claims, 60 Drawing Sheets

Related U.S. Application Data filed on Apr. 6, 2024, provisional application No. 63/566,227, filed on Mar. 16, 2024.

(51) Int. Cl.
  A61B 5/22 (2006.01)
  G16H 80/00 (2018.01)
(52) U.S. Cl.
  CPC .......... A61B 5/4011 (2013.01); A61B 5/7465 (2013.01); G16H 80/00 (2018.01); A61B 2562/168 (2013.01)
(58) Field of Classification Search
  CPC ..... A61B 5/224; A61B 5/4005; A61B 5/4011; A61B 5/7465
  USPC .................................................. 600/300, 301
  See application file for complete search history.

(56) References Cited

U.S. PATENT DOCUMENTS

| | | | | |
|---|---|---|---|---|
| 6,705,990 | B1 * | 3/2004 | Gallant | G16H 40/63 |
| | | | | 600/490 |
| 7,467,871 | B2 * | 12/2008 | Lawhorn | A61B 3/0033 |
| | | | | 351/244 |
| 10,335,339 | B1 * | 7/2019 | Stees | A61G 15/10 |
| 10,568,547 | B1 * | 2/2020 | Johanning | A61B 5/224 |
| 2008/0216570 | A1 * | 9/2008 | Andres | A61B 5/1071 |
| | | | | 73/379.01 |
| 2010/0286492 | A1 * | 11/2010 | Baudino | G16H 20/00 |
| | | | | 600/301 |
| 2011/0082384 | A1 * | 4/2011 | Harte | A61B 5/4827 |
| | | | | 600/557 |
| 2013/0281887 | A1 * | 10/2013 | David | A61B 5/282 |
| | | | | 600/587 |
| 2016/0007921 | A1 * | 1/2016 | Galea | A61B 3/113 |
| | | | | 600/301 |
| 2018/0064386 | A1 * | 3/2018 | Johns | A61B 5/459 |
| 2020/0215329 | A1 * | 7/2020 | Kilgard | A61N 1/36103 |
| 2020/0368090 | A1 * | 11/2020 | Waterson | A61G 15/10 |
| 2021/0369530 | A1 * | 12/2021 | Turocy | A61B 90/35 |
| 2022/0117489 | A1 * | 4/2022 | Jagadeesan | G16H 10/40 |

OTHER PUBLICATIONS

C. Wang, S. Hassan and J. A. Covington, "A Multi-scent Olfactory Display for Smell Identification Testing," 2024 IEEE International Symposium on Olfaction and Electronic Nose (ISOEN), Grapevine, TX, USA, 2024, pp. 1-3, doi: 10.1109/ISOEN61239.2024. 10556127. (Year: 2024).*

* cited by examiner

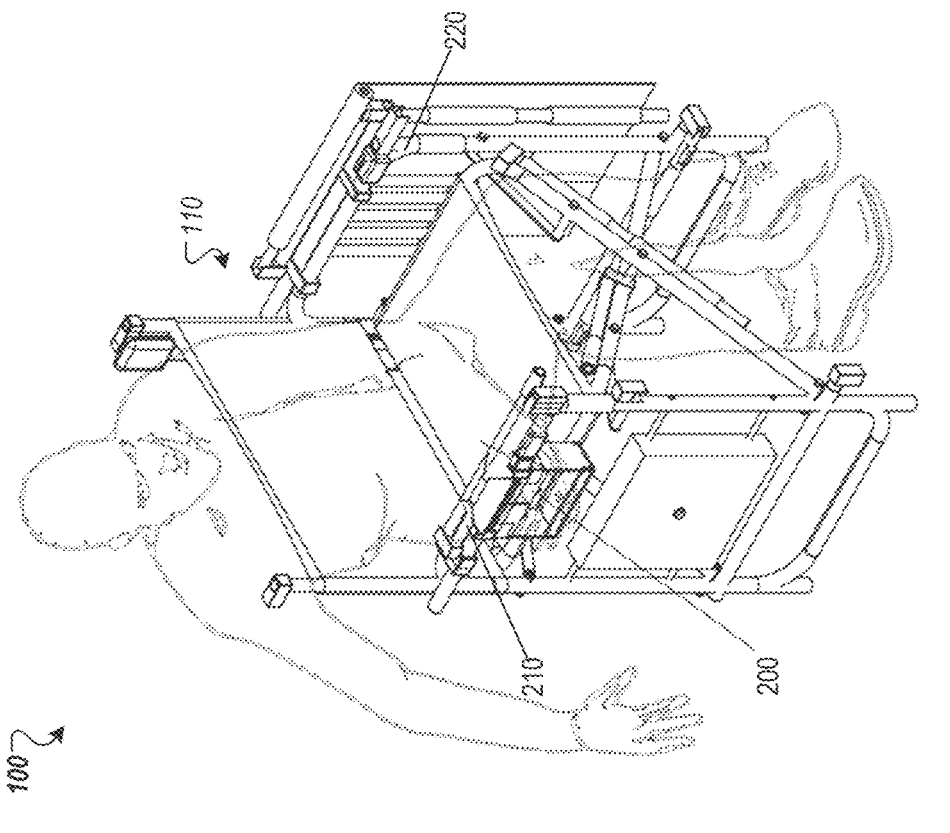
FIG. 2B
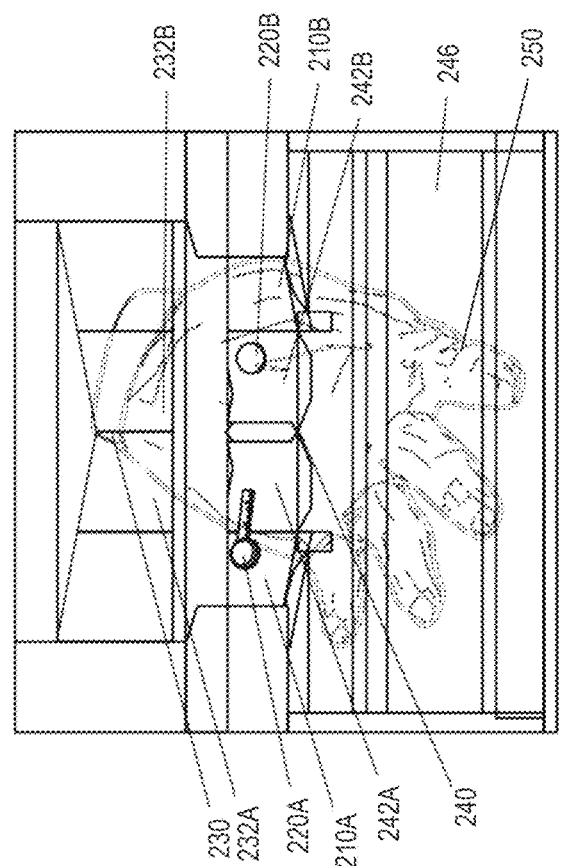
FIG. 2A

100

120A

600A

110

600B

120B

600D

500

120C

500

600C

FIG. 10

1200

1200

1400

Exam Components

1410

1520

1520

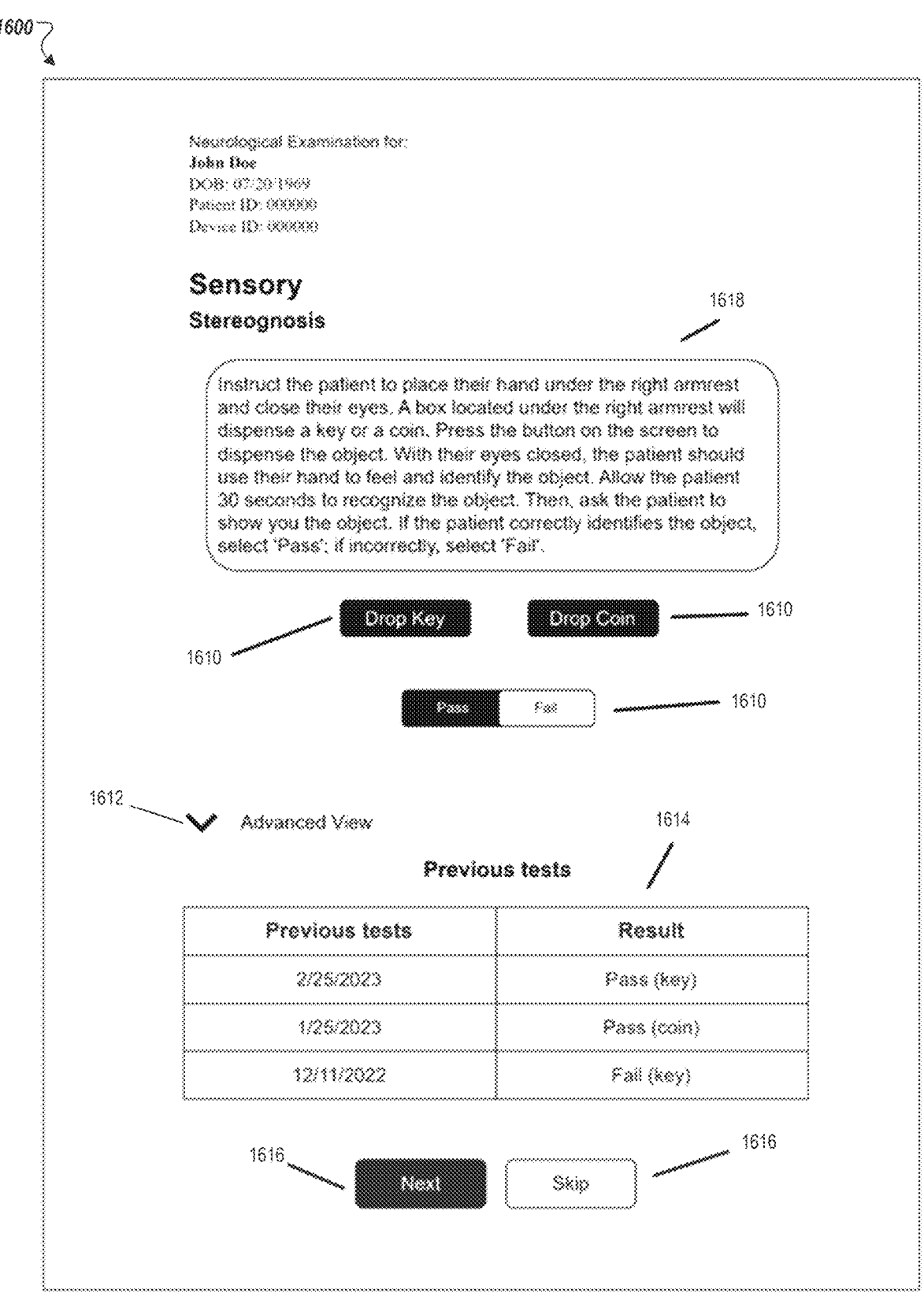

*1600*

Neurological Examination for:
John Doe
DOB: 07/20/1969
Patient ID: 000000
Device ID: 000000

Sensory
Stereognosis

1618

Instruct the patient to place their hand under the right armrest and close their eyes. A box located under the right armrest will dispense a key or a coin. Press the button on the screen to dispense the object. With their eyes closed, the patient should use their hand to feel and identify the object. Allow the patient 30 seconds to recognize the object. Then, ask the patient to show you the object. If the patient correctly identifies the object, select 'Pass'; if incorrectly, select 'Fail'.

Drop Key          Drop Coin          1610

1610

Pass    Fail          1610

1612    Advanced View          1614

Previous tests

| Previous tests | Result |
|---|---|
| 2/25/2023 | Pass (key) |
| 1/25/2023 | Pass (coin) |
| 12/11/2022 | Fail (key) |

1616          Next          Skip          1616

1700

Neurological Examination for:
John Doe
DOB: 07-20-1964
Patient ID: 00000
Device ID: 00000

Sensory
Temperature (Right Hand)

1718

Instruct the patient to place their right hand on the vibration/temperature module in the right armrest. Ask the patient to select what they feel (Cold, Hot, or No Sensation) on the screen. If the patient correctly identifies the temperature, select 'Pass'; if incorrectly, select 'Fail'.

Cold     Hot     1710

1710

Pass | Fail     1710

1712

⌄ Advanced View

1715     Current temperature     1714

Previous tests

| Previous tests | Result |
|---|---|
| 2/25/2023 | Pass (key) |
| 1/25/2023 | Pass (coin) |
| 12/11/2022 | Fail (key) |

Temperature (F)

1716     Next     Skip     1716

FIG. 17A

1800

Neurological Examination for:
John Doe
DOB: 07/20/1989
Patient ID: 999999
Device ID: 999999

Sensory
Vibratory (Right Hand)

1818

Instruct the patient to put their right hand on the vibration/temperature module in the right armrest. If the patient feels vibration, patient has to press the button on their right armrest.

Start Test ──── 1810

1812

⌄ Advanced View

Current vibration strength

1815

| | |
|---|---|
| 4.5 | |
| 4 | |
| 3.5 | |
| 3 | |
| 2.5 | |
| 2 | |
| 1.5 | |
| 1 | |

Vibration strength (G)

1814

Previous tests

| Previous tests | Result |
|---|---|
| 2/25/2023 | Pass (2) |
| 1/25/2023 | Pass (2.5) |
| 12/11/2022 | Fail (4.5) |

1816 ──── Next    Skip ──── 1816

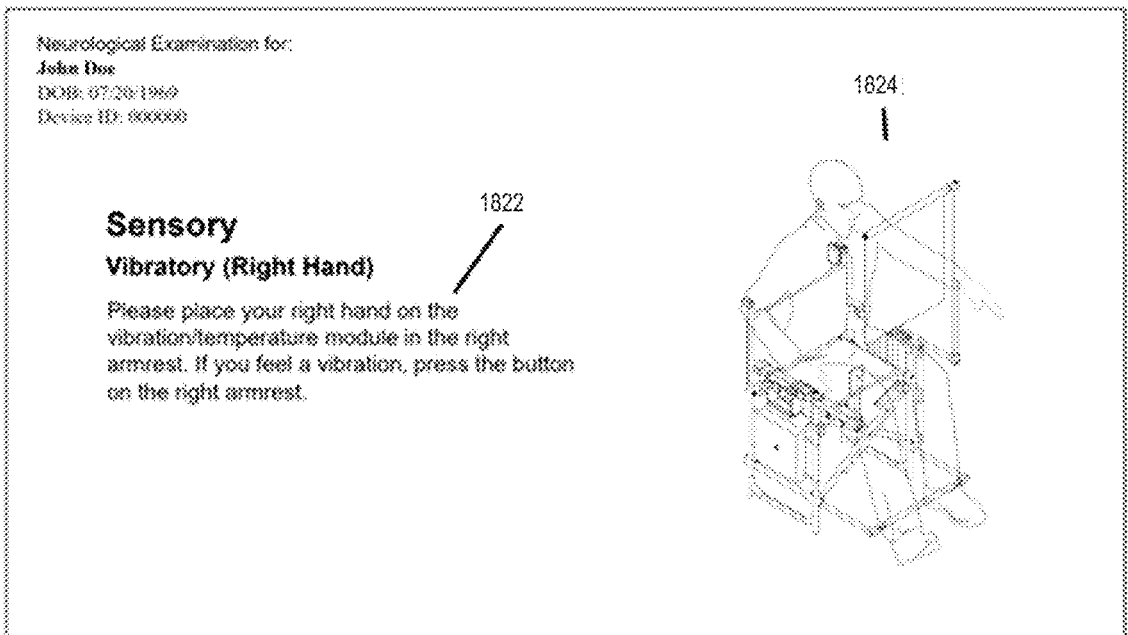

Neurological Examination for:
John Doe
DOB: 07/20/1969
Device ID: 888888

Sensory   1822
Vibratory (Right Hand)

Please place your right hand on the
vibration/temperature module in the right
armrest. If you feel a vibration, press the button
on the right armrest.

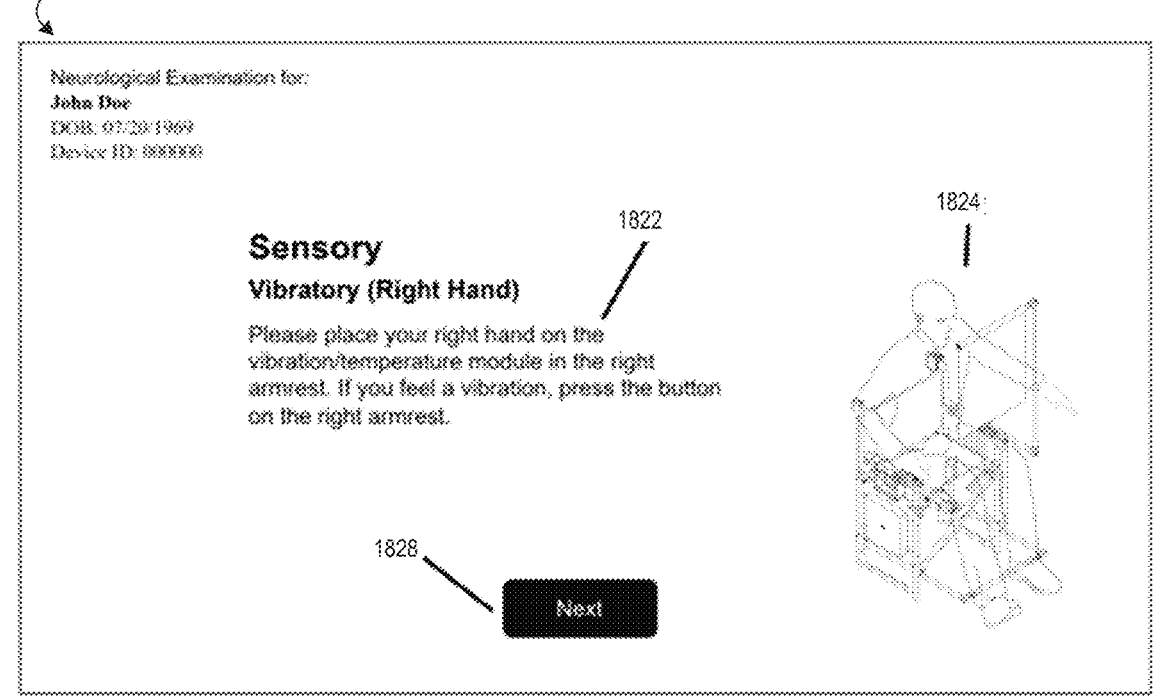

Neurological Examination for:
John Doe
DOB: 07/20/1969
Device ID: 888888

Sensory   1822
Vibratory (Right Hand)

Please place your right hand on the
vibration/temperature module in the right
armrest. If you feel a vibration, press the button
on the right armrest.

1824

1828   Next

2000

Neurological Examination for:
Jake Doe
DOB: 10-20-1949
Patient ID: 000000
Device ID: 000000

Cranial Nerve
CN I (Olfaction)

2018

Instruct the patient to identify the emitted odor by choosing the corresponding option on the display screen.

Emit Lemon     Emit Coffee     Emit Chocolate 2012     2010     2010     2010

∨ Advanced View

2014

Currently being emitted: Coffee

Previous tests

2015

| Previous tests | Result |
|---|---|
| 2/25/2023 | Pass (Coffee) |
| 1/25/2023 | Pass (Chocolate) |
| 12/11/2022 | Fail (Lemon) |

2016 —— Next     Skip —— 2016

FIG. 20A

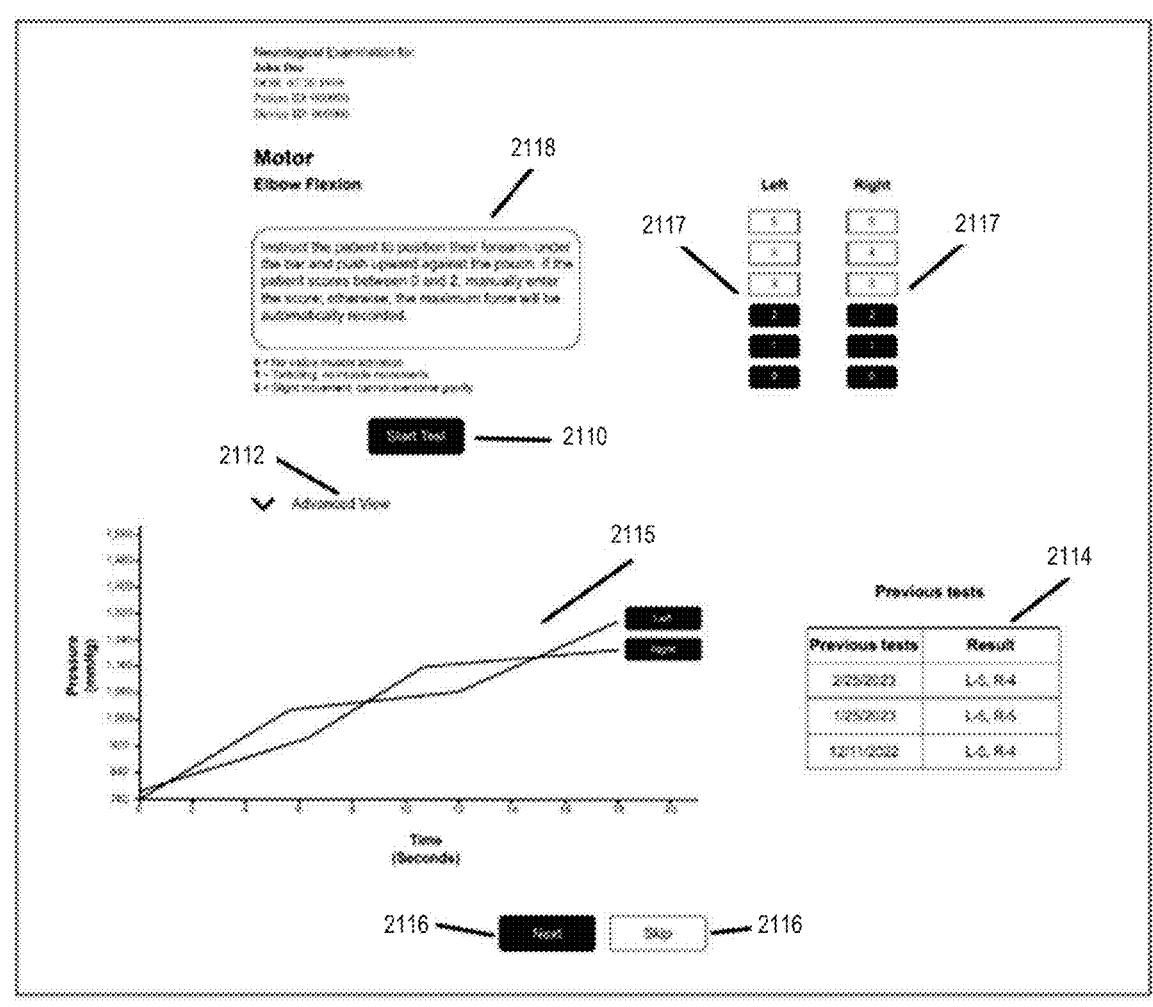
FIG. 21A

2220

2220

2320

2320

2620

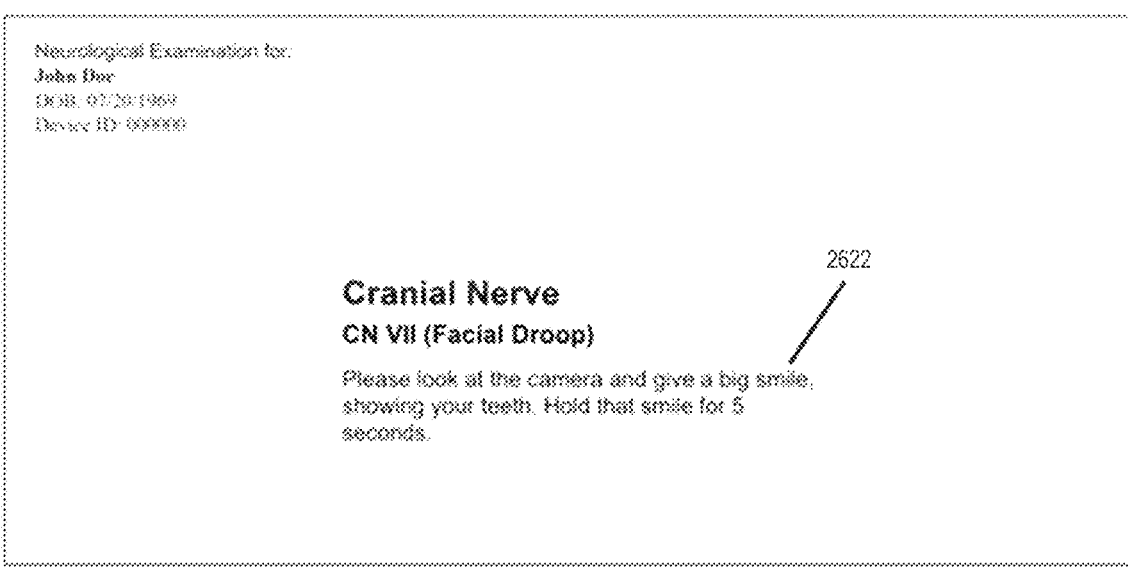

Neurological Examination for:
John Doe
DOB: 07/20/1969
Device ID: 000000

Cranial Nerve

2622

CN VII (Facial Droop)

Please look at the camera and give a big smile, showing your teeth. Hold that smile for 5 seconds.

Neurological Examination for:
John Doe
DOB: 07/20/1969
Device ID: 000000

Cranial Nerve

2622

CN VII (Facial Droop)

Please look at the camera and give a big smile, showing your teeth. Hold that smile for 5 seconds.

2628

Next

FIG. 26C

2720
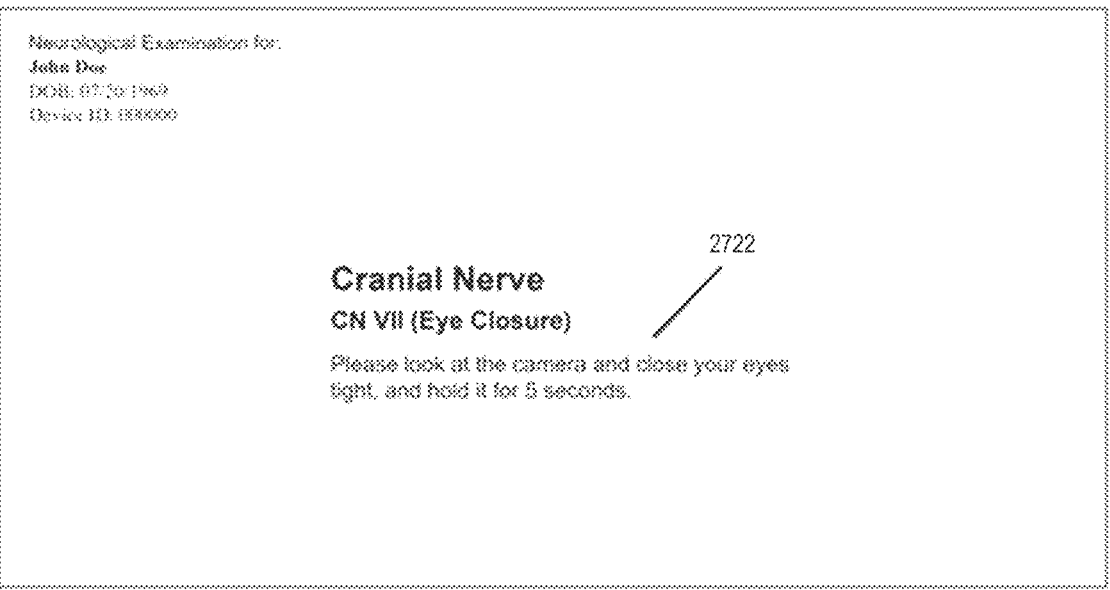
2722
Cranial Nerve
CN VII (Eye Closure)
Please look at the camera and close your eyes tight, and hold it for 5 seconds.
FIG. 27B
2720
Cranial Nerve
CN VII (Eye Closure)
Please look at the camera and close your eyes tight, and hold it for 5 seconds.
2722
2728
Next
FIG. 27C

2820

2820

2900

3020

3020

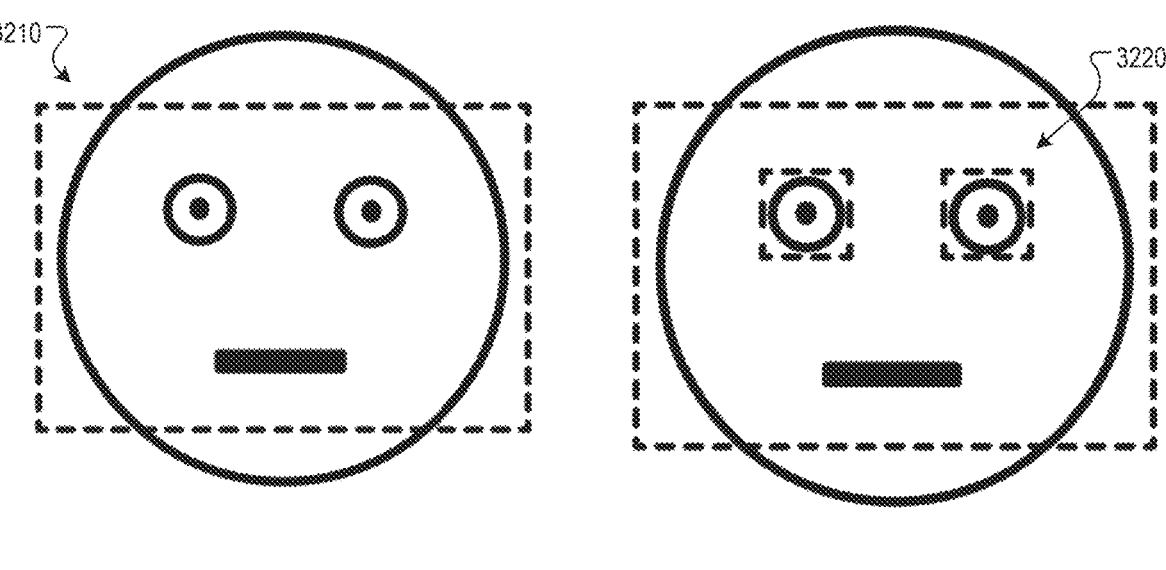
FIG. 32A                    FIG. 32B
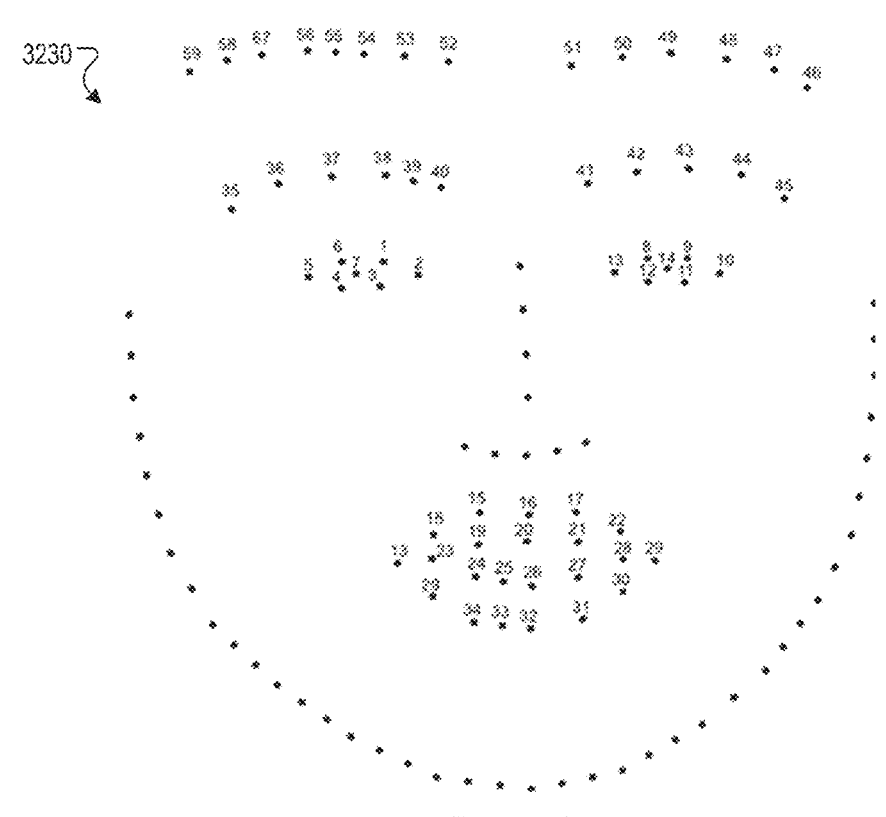
FIG. 32C

NEUROLOGICAL EXAMINATION SYSTEM

RELATED APPLICATIONS

This application claims the benefit of Provisional Application No. 63/566,227, filed Mar. 16, 2024, Provisional Application No. 63/575,624, filed Apr. 6, 2024, and Provisional Application No. 63/694,658, filed Sep. 13, 2024, the contents of which are incorporated by reference in their entirety,

TECHNICAL FIELD

Embodiments of the present disclosure relate to examination systems, and in particular to neurological examination systems.

BACKGROUND

A medical examination is an assessment of a person's health that is performed by a healthcare professional (e.g., a physician). Medical examinations may help evaluate a person's physical and/or mental conditions.

BRIEF DESCRIPTION OF THE DRAWINGS

The present disclosure is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

FIGS. 2A-B illustrate stereognosis assessment module devices, according to certain embodiments.

FIG. 10 illustrates a perspective view of the neurological examination system, including a videoconferencing device alignment device, according to certain embodiments.

FIGS. 16A-C illustrate GUIs associated with conducting a stereognosis examination, according to certain embodiments.

FIGS. 17A-C illustrate GUIs associated with conducting a temperature sensation portion of a sensory examination, according to certain embodiments.

FIGS. 18A-C illustrate GUIs associated with conducting a vibratory sensation portion of a sensory examination, according to certain embodiments.

FIGS. 20A-C illustrate GUIs associated with conducting an olfaction examination, according to certain embodiments.

FIGS. 21A-C illustrate GUIs associated with conducting a strength examination, according to certain embodiments.

FIGS. 26A-C illustrate GUIs associated with conducting a facial droop examination, according to certain embodiments.

FIGS. 27A-C illustrate GUIs associated with conducting an eye closure examination, according to certain embodiments.

FIGS. 32A-C illustrate computer vision techniques implemented by a processing device of the neurological examination system, according to certain embodiments.

DETAILED DESCRIPTION

Figure 1:
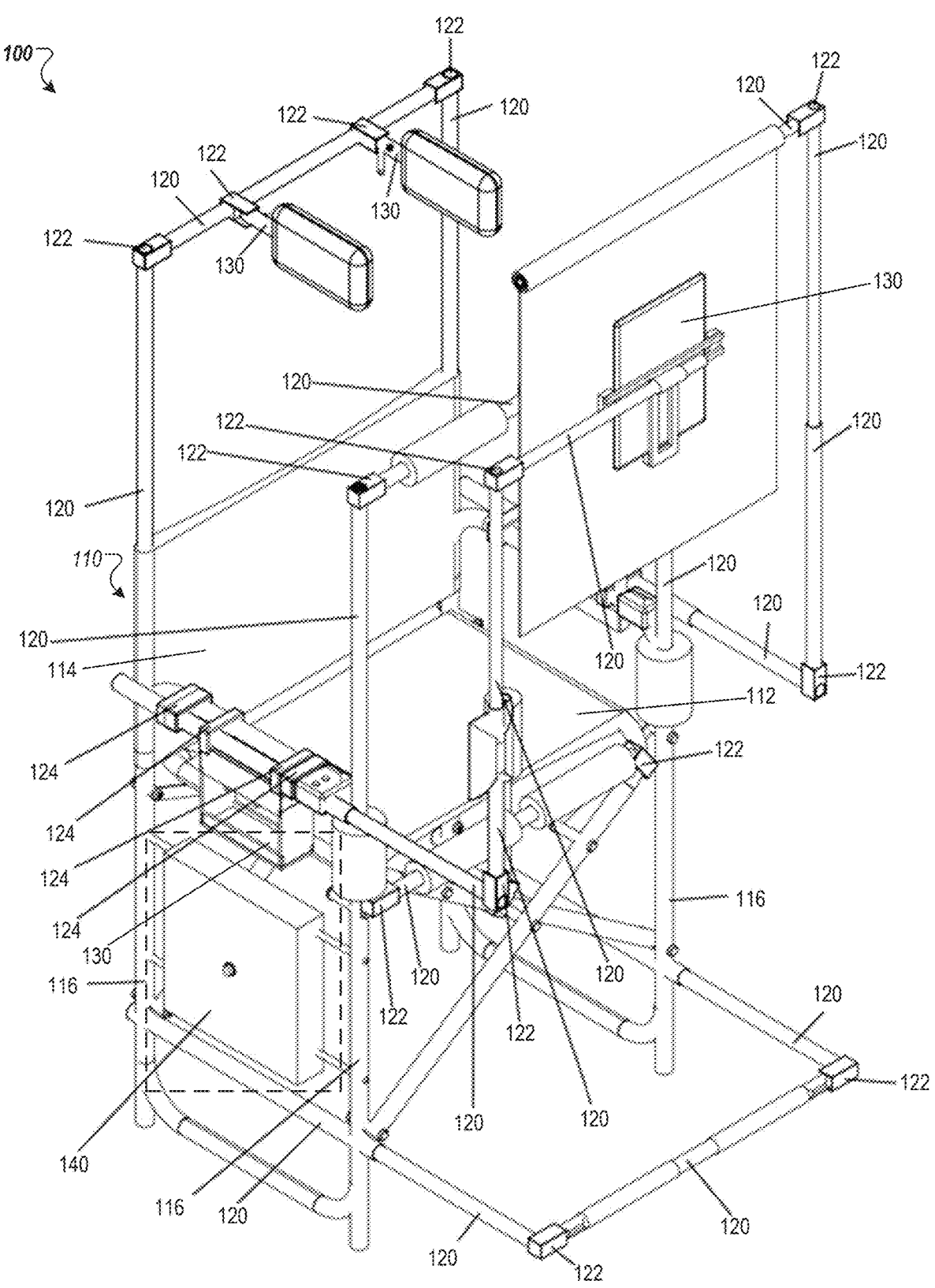
FIG. 1 illustrates a perspective view of a neurological examination system, according to certain embodiments.

Embodiments described herein are related to neurological examination systems.

As the population globally and in the United States ages, the demand for specialized medical care, particularly neurological medical care, rises. Neurological medical care relies on neurological examinations conducted as part of a neurological evaluation, during which a neurologist can create a list of differential diagnoses for a patient, often from the data collected during examination alone. However, the quality of the examination depends on a neurologist's subjective interpretation of a patient's performance on the examination and varies from clinician to clinician. The subjective nature of conventional neurological examinations makes it difficult to gather consistent, objective data, which leads to inaccuracies in neurological examinations over time and negatively impacts the patient's continuity of care. Furthermore, neurological examinations may be conducted by physicians with other specializations, such as emergency physicians, primary care physicians, neurosurgeons, physical medicine physicians, and/or rehabilitation physicians. While these physicians face the same challenge of inconsistent or subjective data, the challenge is often exacerbated because these physicians conduct neurological examinations less frequently, which could lead to diagnostic inconsistencies when subjective interpretation is required.

There is also a significant shortage of neurologists or other physicians able to conduct neurological examinations, causing patients to either travel to see an available neurologist or use a telehealth option. Telehealth (e.g., health services provided remotely) utilizes communication technologies to provide healthcare remotely to patients and has many advantages. For instance, the remote nature of telehealth minimizes exposure to communicable diseases without sacrificing visit frequency for the epidemiologically vulnerable. Telehealth also reduces costs, minimizes the instances of missed appointments, and streamlines service delivery. Telehealth also benefits patients who value the convenience and flexibility of virtual appointments, especially in the post-COVID-19 world. However, current telehealth options have limitations, such as the use of common video conferencing technology which possess conventional video and audio capabilities. Because most devices in a patient's possession are not designed with telehealth in mind and patients may have difficulty in using devices, technical limitations of these devices and the users prevent the full potential of telehealth from being realized. Telehealth cannot and should not be limited to the capabilities of these devices and users.

Teleneurology (e.g., telehealth neurology, telehealth neurological examinations) is a fast-growing field that has led to tertiary medical centers (e.g., smaller hospitals that do not have in-house neurologists) offering remote consultations to patients in inpatient, emergency department, and primary clinic settings. A neurological exam is usually performed by a physician trained in a different specialty under the guidance of a neurologist. Thus, a neurological exam is often limited, and findings are often misleading, leading to a demand for a way to obtain objective neurological data.

Due to the complexity of neurological examination, its quality during a telehealth visit is decreased compared to an in-person neurological examination.

Aspects and embodiments of the present disclosure address these and other limitations of the existing technology by providing a neurological examination system. A neurological examination system of the present disclosure may alleviate the aforementioned issues and improve neurological care by automating neurological examinations for utilization in telehealth and/or other uses. The neurological examination system of the present disclosure may collect accurate and objective data, standardize examination results, precisely track changes in neurological examinations over time, shift parts of the neurological examination to more readily available (e.g., lower cost) clinicians, save time, and improve telehealth examinations.

In some embodiments, a system (e.g., a neurological examination system) includes a patient placement module (e.g., a chair, a bed, a stool, a wheelchair, a gurney, etc.) situated to receive a patient, one or more arms connected to the chair, and two or more assessment module devices. Each of the two or more assessment module devices may be connected to a respective arm of the one or more arms. Each of the one or more assessment module devices may be configured to provide a respective set of assessment data associated with a neurological examination of the patient. In some embodiments, the respective set of assessment data is provided to a processing device (e.g., executing an application). The processing device may receive the respective set of assessment data from the assessment module devices, determine assessment outcome data, and provide the assessment outcome data to a user device.

The devices, systems, and methods disclosed herein provide a neurological examination system configured to provide more objective data, enabling more accurate examination, more precise tracking of neurological examination changes, and improving continuity of care compared to conventional solutions. The present disclosure may be used for telehealth and may surpass the limitations of conventional household technology and extending telehealth's applications to neurological health care. Because neurological care cannot be fully delivered through common video conferencing technology, the systems, devices, and methods of the present disclosure may be used for remote neurological care to enhance the capabilities of neurological care delivered via telehealth compared to conventional solutions.

The present disclosure may mitigate misdiagnosis compared to conventional solutions by equipping physicians with objective and standardized data to make a more correct diagnosis. More accurate quantitative data provided by the present disclosure may help neurologists and other clinicians notice subtle abnormalities such as decreased muscle strength (e.g., demyelinating conditions) or peripheral vision loss (e.g., optic chiasm compression by tumor) at earlier stages than conventional solutions.

Integration of the present disclosure into vital sign check-in processes may allow readily available medical staff such as nurses and physician assistants to conduct parts of a neurological examination. This allows neurologists to focus on conducting more complex tests and more thorough neurological examinations to facilitate the diagnostic process better than conventional solutions.

In some embodiments, the neurological examination system can be controlled by the processing device (e.g., executing an application), which can be operated by various operators and/or users (e.g., via a user device, via an input/output module device of the neurological examination system, etc.) including, but not limited to, a medical provider, a researcher, a patient, and/or an assistant to the patient. Depending on the operator and/or user, the range of available tests may vary. The term "operator" as used herein may refer to a person or program controlling the one or more assessment module devices through the processing device (e.g., the application).

Test data (including assessment data) can be stored in various places including, but not limited to, internal memory of a computation module (e.g., of the neurological examination system) and/or transmitted and stored by the processing device controlling the neurological examination system. With the present disclosure, neurological examination can be performed in various conditions including, but not limited to, clinic check-in, inpatient services, a telehealth visit, a teleneurology visit, research lab, space crafts, or even by the patient at his/her own convenience (e.g., at the patient's residence).

The neurological examination system may include at least two of the following assessment module devices and/or systems: a stereognosis assessment module device, an auditory assessment module device, an olfactory assessment module device, a strength assessment module device, a sensory assessment module device, ocular assessment module device, a facial nerve assessment module device, a hypoglossal nerve assessment module device, and/or a coordination assessment module device. These various assessment module devices may allow for more accurate, more objective, and/or more quantitative assessments of mental status, cranial nerves and brainstem reflexes, muscle strength, coordination, and/or sensory functions than conventional solutions. Assessment module devices are described in greater detail in the present disclosure.

The processing device (e.g., executing an application) may execute one or more types of software, which include but are not limited to a front-end software, a server-side software, and/or embedded software. The processing device supports and enables the functionality of the various assessment module devices. The processing device enables functionality such as, but not limited to, controlling the various assessment module devices, inputting and/or selecting data for assessment purposes, analyzing data such as current and historical results and trends, storing data, transmitting data, and/or processing data.

The terms "such as, but not limited," "comprises" or any other variation thereof, are intended to cover a non-exclusive inclusion, such that a process, method, article, or apparatus that comprises a list of elements does not include only those elements but may include other elements not expressly listed or inherent to such process, method, article, or apparatus.

The terms "a," "an," and "the" and similar referents used herein are to be construed to cover both the singular and the plural unless their usage in context indicates otherwise. The word "embodiment" is used herein to mean "serving as an example, instance, or illustration." Implementations or embodiments described herein are not necessarily to be construed as preferred or advantageous over other embodiments or implementations. Likewise, "embodiments" does not require that all embodiments include the discussed feature, advantage, or mode of operation.

The term "computational electronic device" and variations thereof, as used herein, are used interchangeably and include, but are not limited to, a processing device, a processor, a general purpose computer, a general purpose processor, a digital signal processor (DSP), an application-specific integrated circuit (ASIC), a field programmable gate array (FPGA) or other programmable logic component, discrete gate or transistor logic, discrete hardware components, or any combination thereof designed to perform the functions described herein. A general-purpose computer may include a microprocessor, as well as any conventional processor, controller, microcontroller, or state machine. The processor may also be implemented as a combination of computing components, such as a combination of a DSP and a microprocessor, a number of microprocessors, one or more microprocessors in conjunction with a DSP core, an ASIC and a microprocessor, or any other number of varying configurations. These examples of the processors and computers are for illustration and other suitable configurations within the scope of the disclosure are also contemplated. Furthermore, the processor or a computer may be implemented as one or more processors, one or more controllers, in any combination with supporting hardware, and/or other structure configured to execute executable programming.

The term "module" and/or "module device" as used herein may refer to, include, and/or execute one or more of hardware, software, firmware, artificial intelligence, fuzzy logic, and/or combination of hardware and software that is capable of performing the functionality associated with that element.

FIG. 1 illustrates a perspective view of a neurological examination system 100, according to certain embodiments. The neurological examination system 100 may include a patient placement module 110, one or more arms 120 (e.g., rail system), and one or more assessment module devices 130. In some embodiments, the patient placement module 110 is a chair including a chair seat 112, a chair back 114, and/or one or more chair legs 116.

The patient placement module 110 may include a chair with a seated portion and one or more legs to support the seated portion. In some embodiments, the patient placement module 110 is configured to put a patient into a predictable position such as, but not limited to, a sitting position, a supine position (e.g., laying face upward), and/or a standing position. This may be used for other assessment module devices and/or systems of the present disclosure to function properly, as the other assessment module devices and/or systems are to be used with certain body parts in certain areas in relation to the assessment module devices and/or systems original positions and/or to the positions of other body parts.

In some embodiments, the one or more arms (e.g., the arms) 120 are configured to position the one or more assessment module devices 130, described further herein, into areas around the patient placement module 110 (e.g., around a user's body, around a patient's body) so the assessment module devices 130 can perform their functions. The arms 120 may be used as a substitute for a neurological examiner (e.g., a doctor, a nurse, a health practitioner, etc.) moving around the user during conventional neurological examination where the neurological examiner may perform tests using hands or tools.

The arms 120 may be part of a rail system including a set of rails (e.g., bodies, tubes) that telescope in and out of each other to respectively increase and decrease the overall length of the arms 120. These rails may have hinges 122 attached to them to allow the combination of several groups of rails in a non-linear structure to allow for 3-dimensional positioning (e.g., complex 3-dimensional positioning). These rails may be embedded into (e.g., integral to) the structure of the patient placement module 110 and/or attached to the patient placement module 110 using mounting hardware (e.g., nuts, bolts, screws, anchors, clips, brackets, adhesives, hook-and-loop attachments, etc.).

The arms 120 may be made of a sturdy, non-bending material, such as plastic (e.g., polyvinyl chloride (PVC), polyethylene (PE), acrylonitrile butadiene styrene (ABS), etc.), metal (e.g., copper, galvanized steel, stainless steel, aluminum, etc.), and wood. Each of the arms 120 may be a contiguous arm (e.g., an arm made of on piece of material) or made of multiple parts (e.g., rails). In some embodiments, the rails may form a telescoping arm (e.g., nesting arm) that collapses the rails into a retracted position (e.g., when not in use in the neurological examination system) and locks the rails into an extended position (e.g., for use in the neurological examination system). In other embodiments, each rail is connected to other parts of the arm 120 by hinges 122 and/or clamps 124.

The arms 120 may also be attached to the patient placement module 110 via hinges 122 and/or clamps 124. The hinges 122 may be a set of 90° hinges (e.g., right angle hinges) that allow the relative angle of the arms 120 to the chair 110 to change and/or the relative angle of individual rails to change with respect to other rails. In some embodiments, the clamps 124 are used to connect the rails to each other and/or to the chair 110. In some embodiments, the arms 120 are attached to the patient placement module 110 via other connectors, such as brackets, joints, couplings, latches, bolts, flanges, cam locks, hangers, etc.

In some embodiments, the arms 120 are moveable between a first position and a second position. The first position may be an operational position (e.g., for use in a neurological examination) that is adjustable to the patient and is associated with providing assessment data. For example, the arms 120 may be adjustable to accommodate patients of various heights and/or appendage lengths. The second position may be a stowed position (e.g., for storage when not in use). In some embodiments, the second position is not associated with providing assessment data.

In some embodiments, the one or more assessment module devices 130 may include a stereognosis assessment module device, an auditory assessment module device, an olfactory assessment module device, a strength assessment module device, a sensory assessment module device, an ocular assessment module device, a facial nerve assessment module device, a hypoglossal nerve assessment module device, and/or a coordination assessment module device. Each assessment module device will be discussed in greater detail in the present disclosure.

The neurological examination system 100 may further include a processing device 140. The processing device 140 may receive assessment data to determine assessment outcome data (e.g., a diagnosis, readings of the assessment data, etc.). The processing device 140 may be connected to the patient placement module 110, part of an assessment module device, and/or an application used to operate the neurological examination system 100. The processing device 140 may further include a computational module. In some embodiments, the computation module includes a computational electronic device or collection of devices with local connectivity, such as, but not limited to, Bluetooth® Classic, Bluetooth® LE, Wi-Fi® Direct, Wi-Fi® HaLow, Ultra-wideband, and Internet connectivity utilizing Wi-Fi®, Ethernet and/or Cellular communication. In addition, the computation module can include, but not limited to, power supply(s) and/or motor(s) and/or sensors and/or buttons and/or fans. The computational module may receive commands from the server and/or application controlling the neurological examination system 100. The computational module can control and transmit data (e.g., assessment data) to and/or from all the assessment module devices and transmit/relay it to the server and/or application controlling the device, for the purposes of conducting a neurological examination.

FIGS. 2A-B illustrate stereognosis assessment module devices 200, according to certain embodiments. FIG. 2A illustrates a close-up view of an example stereognosis assessment module device 200 according to one embodiment. FIG. 2B illustrates an isometric perspective view of a patient using the neurological examination system 100, including the example stereognosis assessment module device 200, according to one embodiment. FIG. 2B shows substantially similar components as those illustrated in FIG. 2A.

A neurological examination system (e.g., the neurological examination system 100 of FIG. 1) may include the stereognosis assessment module device 200. In some embodiments, the stereognosis assessment module device 200 may be used to assess the patient's ability to identify an object via a three-dimensional (e.g., 3D) shape and form of the object. During conventional neurological examination, a neurological examiner places a familiar object in the patient's hand and asks the patient to identify the object. The stereognosis assessment module device 200 may act as a substitute for a neurological examiner manually placing an object into patient's hand.

The stereognosis assessment module device 200 may automate the process of dispensing a familiar object to a patient. In some embodiments, the stereognosis assessment module device 200 includes one or more structures (e.g., volumes, spaces) 210 holding physical objects 220, an input funnel 230, and/or an output funnel 240. An operator may choose one of the physical objects 220 to deliver to the patient's hand 250. The patient may receive the physical object 220 from the output funnel 240, identify the physical object 220, and then put the physical object 220 back into the input funnel 230.

In some embodiments, the stereognosis assessment module device 200 includes a container that forms two structures 210A and 210B for storing the physical objects 220A and 220B, respectively. Structure 210A (e.g., a first volume, a first structure) may have an input door 232A (e.g., a first input door) and an output door 242A (e.g., a second output door). The input door 232A (e.g., a controllable door) may connect the structure 210A to the input funnel 230, and the output door 242A (e.g., a controllable door) may connect the structure 210A to an output funnel 240 and a pickup area 246. Structure 210B (e.g., a second volume, a second structure) may also have an input door 232B (e.g., a second input door) that connects it to the input funnel 230 and an output door 242B (e.g., a second output door) that connects it to the output funnel 240 and pickup area 246.

The physical object 220A (e.g., a first physical object) and the physical object 220B (e.g., a second physical object) may be delivered via the output funnel 240 to the patient's hand 250 (e.g., to be recognized by the patient, providing user input) in the pickup area 246 responsive to actuation (e.g., pushing a button, making a selection) of the stereognosis assessment module device 200 by the patient and/or a user corresponding to either physical object 220A or 220B. For example, if the stereognosis assessment module device 200 receives an input corresponding to the physical object 220A (e.g., the physical object 220A is selected via an input device), the input door 232A and the output door 242A may open (e.g., move from a closed position to an open position) to release the physical object 220A. The physical object 220A may then fall through the output funnel 240 and land in the patient's hand 250 resting in the pickup area 246. In some embodiments, the output door 242A closes (e.g., move from the open position to the closed position) after the physical object 220A enters the output funnel 240. In this example, because the output door 242A opens while the output door 242B remains closed, the physical object 220A falls into the output funnel 240 while the physical object 220B stays in the volume 210B.

Delivering the physical object 220A or 220B to the patient's hand 250 may begin the stereognosis assessment. The patient may feel and/or hold the physical object 220A or 220B with their eyes closed and try to identify the physical object 220A or 220B by only using tactile information. The stereognosis assessment may be completed once the patient identifies the physical object 220A or 220B.

Once the stereognosis assessment is complete (e.g., the patient has recognized the physical object 220A or 220B), the physical object 220A or 220B may be placed back in the corresponding structure 210A or 210B. For example, the physical object 220A may be placed in the input funnel 230 and fall into the structure 210A via the input door 232A. In this example, because the input door 232A is in an open position while the input door 232B is in a closed position, the physical object 220A may travel to the correct structure 210A without entering the structure 210B.

Although FIG. 2B shows the stereognosis assessment module device 200 connected to the patient placement module (e.g., the chair) 110 in a particular location, the stereognosis assessment module device 200 may be attached to different parts of the chair 110. In some embodiments, the stereognosis assessment module device 200 is located below or above a left arm (e.g., a left armrest) and/or a right arm (e.g., a right armrest) connected to the chair 110.

Figures 3A, 3B:
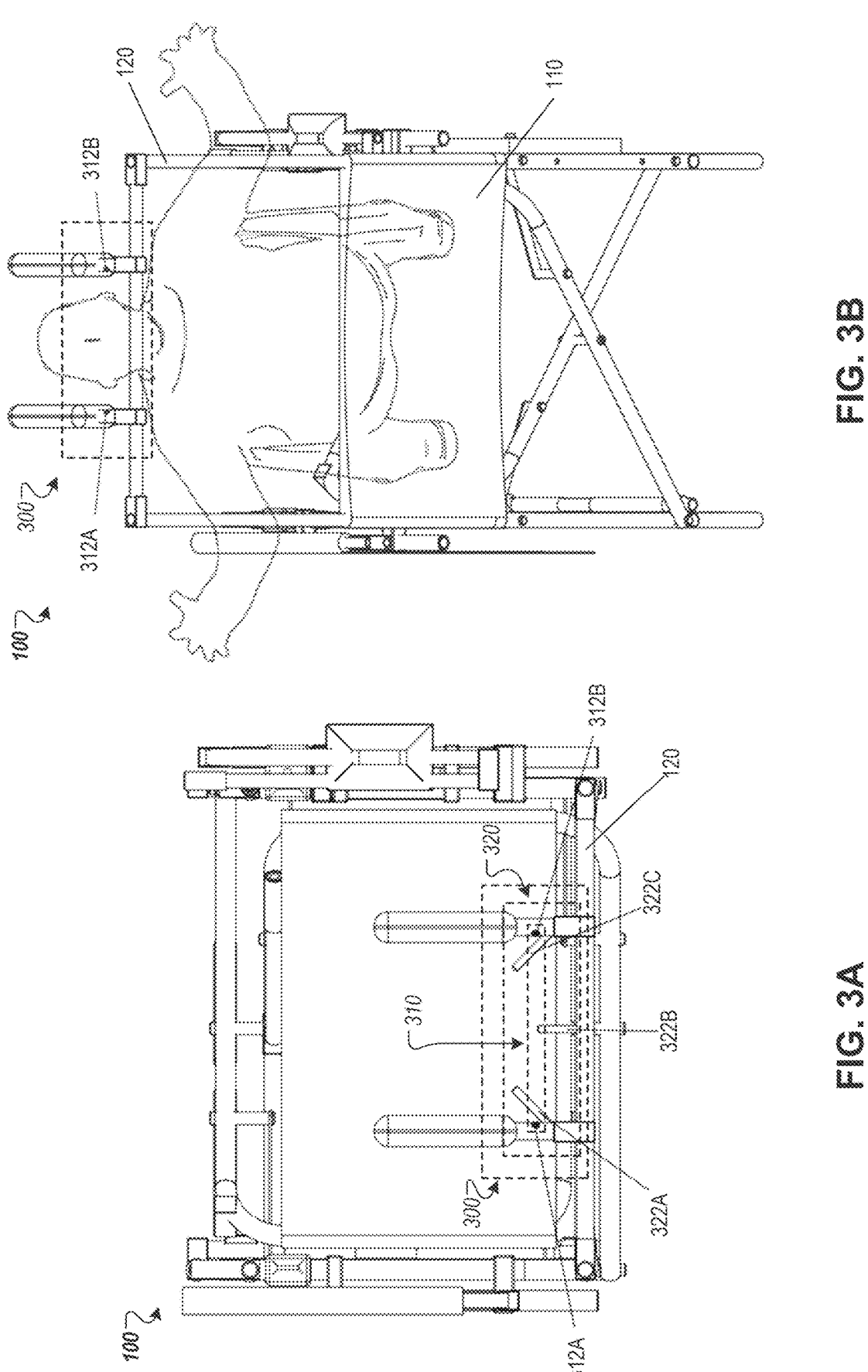
FIGS. 3A-D illustrate auditory assessment module devices, according to certain embodiments.
Figures 3C, 3D:
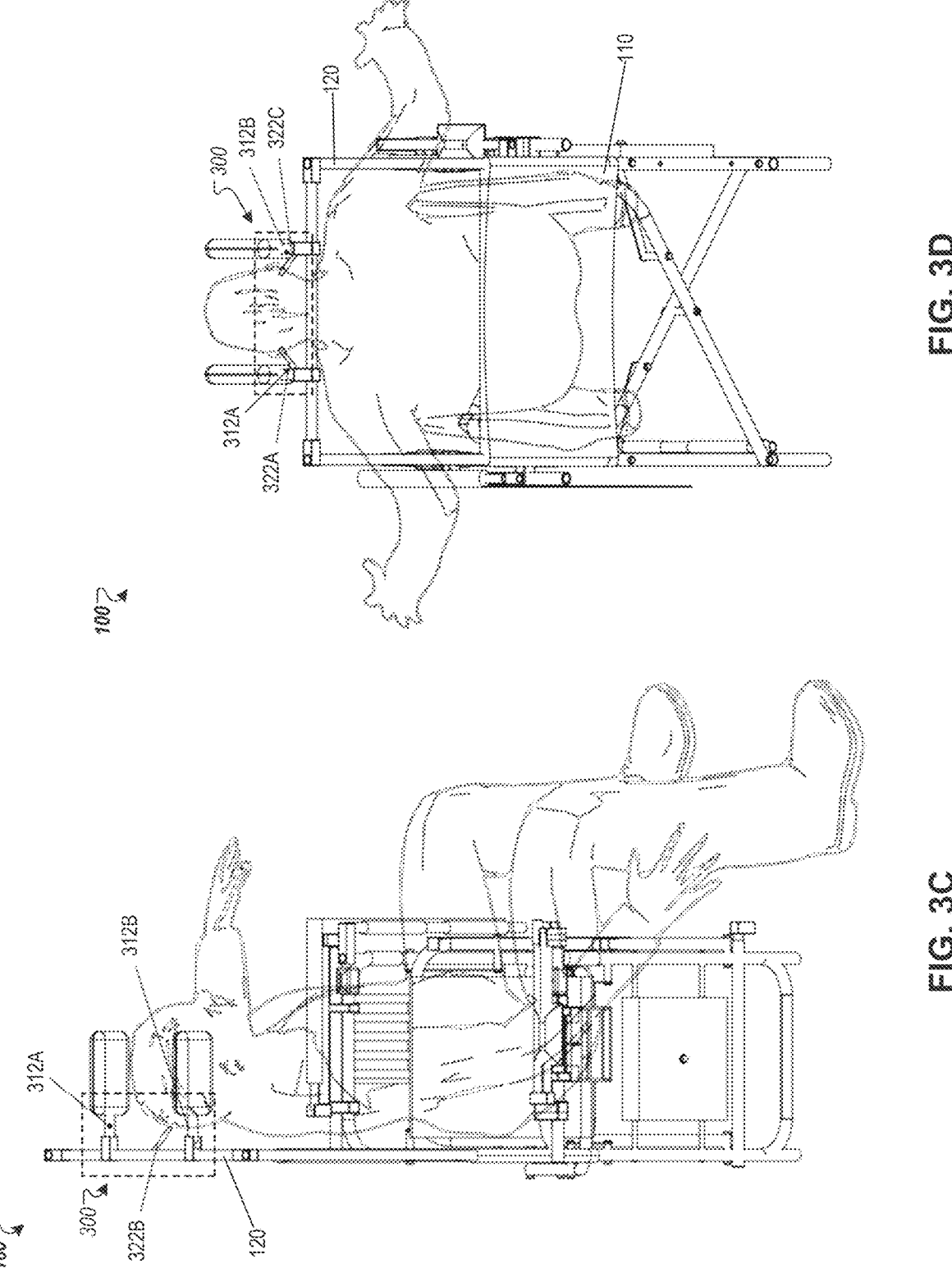

FIGS. 3A-D illustrate auditory assessment module devices 300, according to certain embodiments. FIG. 3A illustrates a perspective view of an auditory assessment module device 300 connected to the arms 120 of the patient placement module (e.g., chair) 110, according to one embodiment. FIGS. 3B-D illustrate perspective views of a patient using the neurological examination system 100, including the auditory assessment module device 300, according to some embodiments. FIG. 3B illustrates a hearing test performed by the auditory assessment module device 300, according to one embodiment. FIG. 3C illustrates a Weber test performed by the auditory assessment module device 300, according to one embodiment. FIG. 3D illustrates a Rinne test performed by the auditory assessment module device 300, according to one embodiment. FIGS. 3B-D show substantially similar components as those illustrated in FIG. 3A.

In some embodiments, the neurological examination system 100 includes an auditory assessment module device 300. In some embodiments, the auditory assessment module device 300 may be used to assess the functioning of the vestibulocochlear nerve (i.e., cranial nerve (CN) VIII, auditory nerve, acoustic nerve, statoacoustic nerve). The vestibulocochlear nerve is responsible for hearing and balance and is composed of the cochlear nerve and the vestibular nerve. Hearing loss is divided into two components: conductive and sensorineural. Conductive hearing loss is caused by the disruption of sound transfer from the external environment to the vestibulocochlear nerve, encompassing the passage of sound waves through the external ear canal and the middle ear. Sensorineural hearing loss pertains to the disruption of sound transmission from the vestibulocochlear nerve to the brain.

The auditory assessment module device 300 may be focused on evaluating the vestibulocochlear nerve for conductive and/or sensorineural types of hearing loss via tests such as hearing tests, Weber tests, and/or Rinne tests. The auditory assessment module device 300 may replace those tests, which are conducted manually by a neurological examiner during a conventional neurological examination.

In some embodiments the auditory assessment module device 300 includes a speaker component 310 and/or a vibration component 320. The speaker component 310 may function as a substitute for human speech or a finger rub and may include one or more speakers 312A-B placed near each ear. The vibration component 320 may function as a substitute for a medical tuning fork used during conventional neurological examinations. The vibration component 320 may include a vibration generator with vibration frequency equaling that of a tuning fork and one or more vibration stems 322A-C that transmits that vibration to a patient's head.

In some embodiments, the speaker component is positioned on inner surfaces of the arms 120 of the neurological examination system 100. The vibration component 320 may be positioned near the speaker component 310 and in the middle of the arms (e.g., equidistant from where a patient's ears may be). The vibration generator (e.g., a motor) may be located inside the arm 120 and the vibration stems 322A-C may extend from the arm 120 to reach the mastoid bone and/or the center of the skull of a patient or retract to prevent harming a patient.

Figures 4A, 4B:
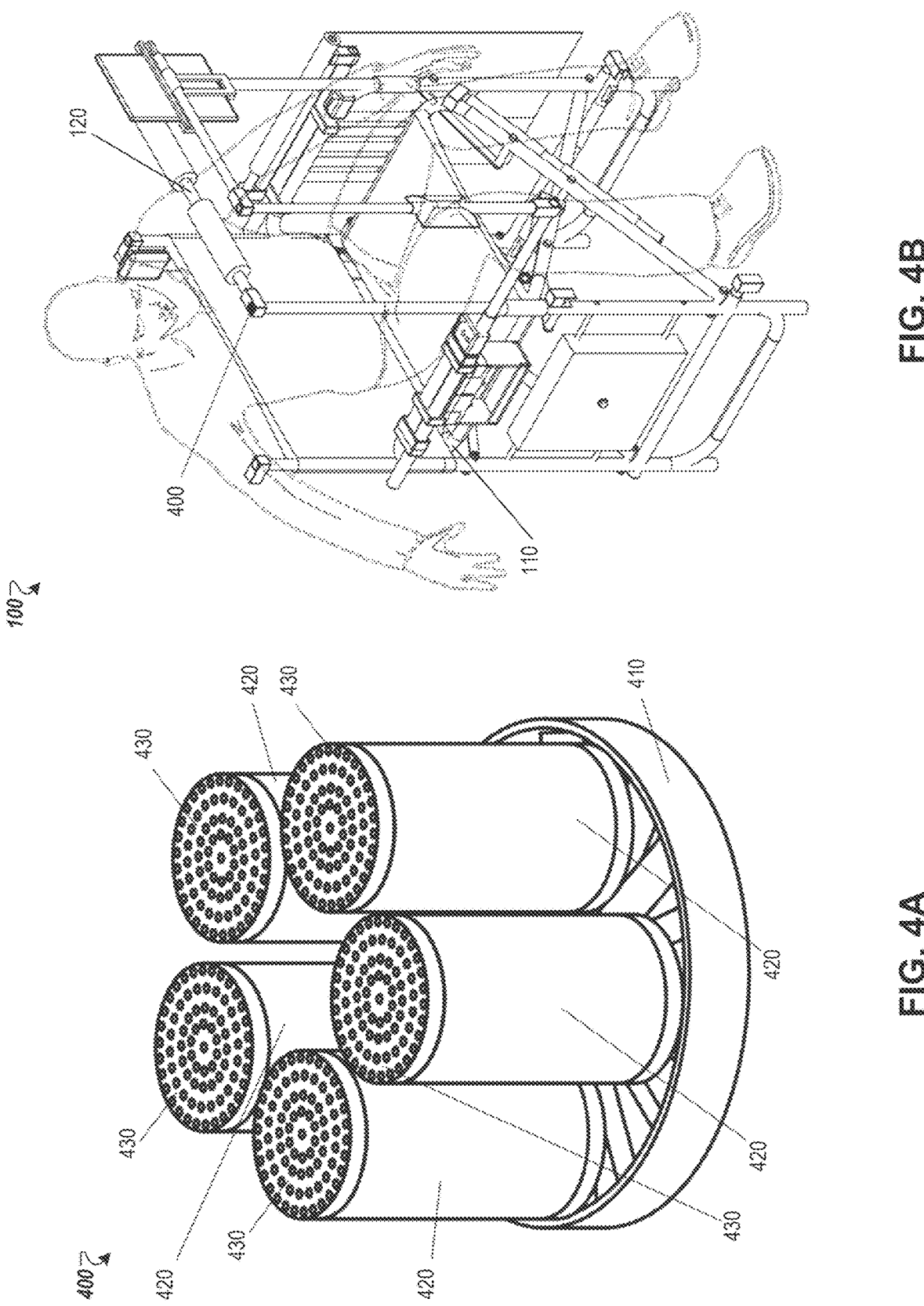
FIGS. 4A-B illustrate olfactory assessment module devices, according to certain embodiments.

FIGS. 4A-B illustrate olfactory assessment module devices 400, according to certain embodiments. FIG. 4A illustrates an olfactory assessment module device 400, according to one embodiment. FIG. 4B illustrates a perspective view of a patient using the neurological examination system 100, including the olfactory assessment module device 400, according to one embodiment. FIG. 4B shows substantially similar components as those illustrated in FIG. 4B.

In some embodiments, the neurological examination system 100 may include the olfactory assessment module devices 400. In some embodiments, the olfactory assessment module devices 400 is to assess a patient's sense of smell (e.g., olfaction). The olfactory assessment module devices 400 may be used to evaluate the olfactory nerve (i.e., CN I, first cranial nerve). The olfactory assessment module devices 400 may replace manual presentation of a distinct common odor, which is the conventional method of olfactory assessment.

The olfactory assessment module devices 400 may include a fan 410 and/or a set of tubes 420 with or without controllable gates 430 filled with common smells such as coffee, lemon, and peanut butter. When gates of a particular tube 420 are opened, the air blown by the fan 410 passes through it carrying the smell to the patient.

The olfactory assessment module device 400 may be attached to diverse parts of the patient placement module 110 and/or the arms 120. In some embodiments, the olfactory assessment module device 400 is positioned at a corner of an arm 120. The olfactory assessment module device 400 may be integral to the arms 120 of the neurological examination system 100 or connected to the patient placement module 110 via screws, clips, and/or other types of connectors. In some embodiments, the olfactory assessment module device 400 is positioned next to a strength assessment module device.

Figure 5A:
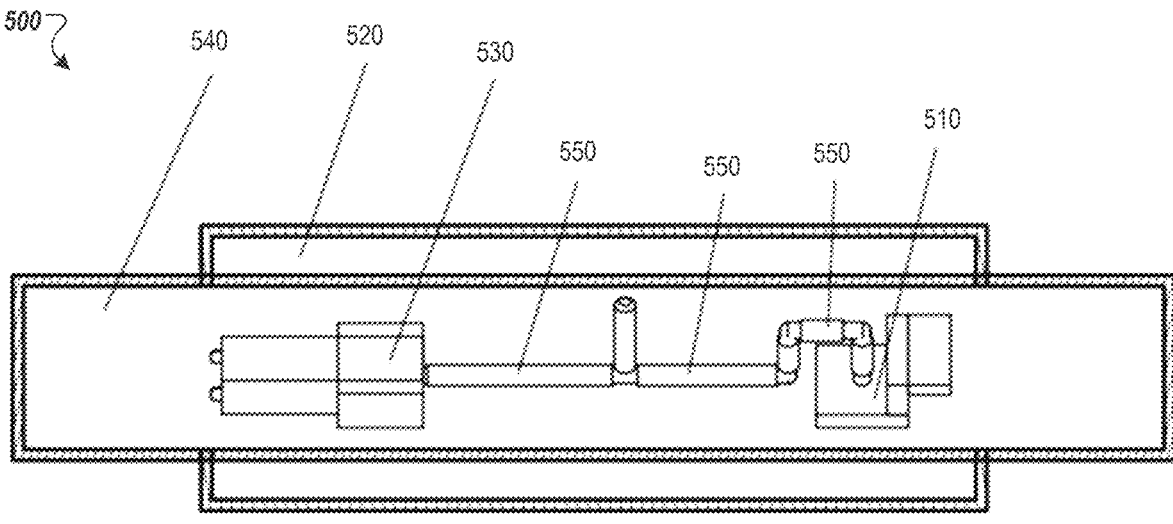
FIGS. 5A-T illustrate strength assessment module devices, according to certain embodiments.
Figure 5B:
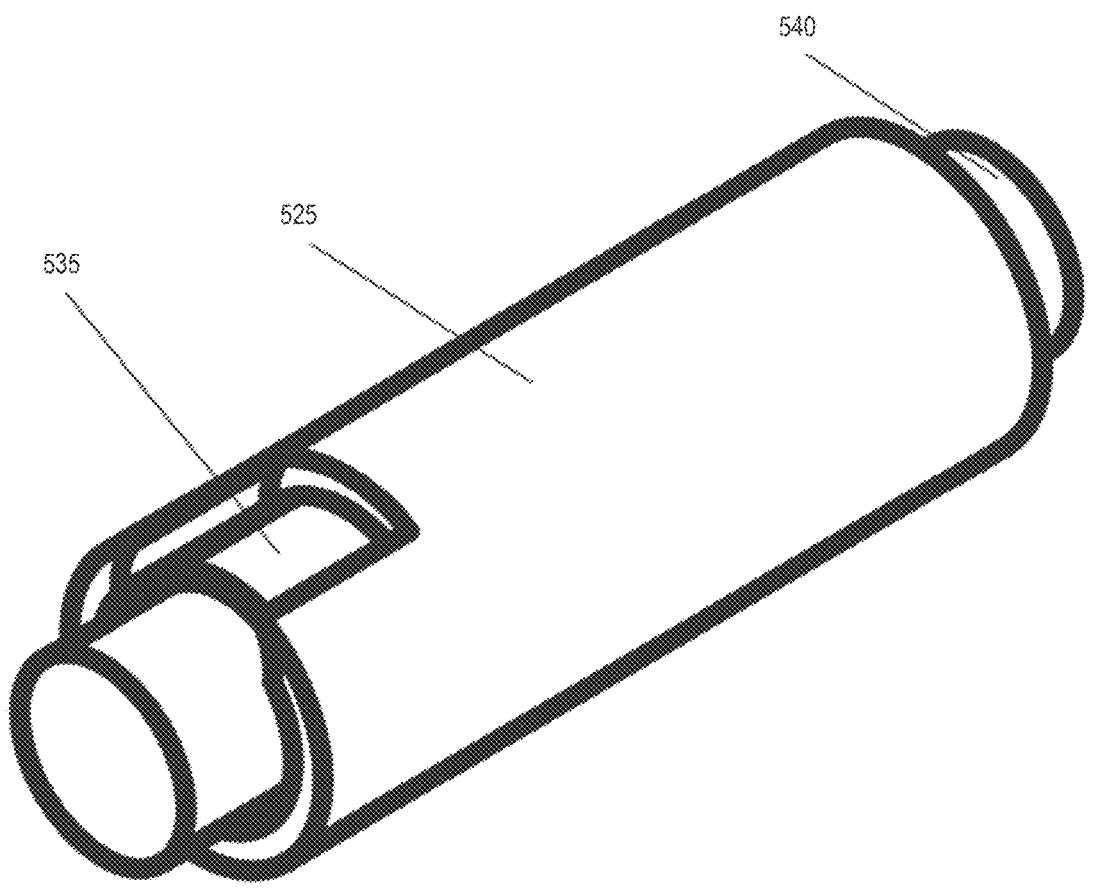
Figure 5D:
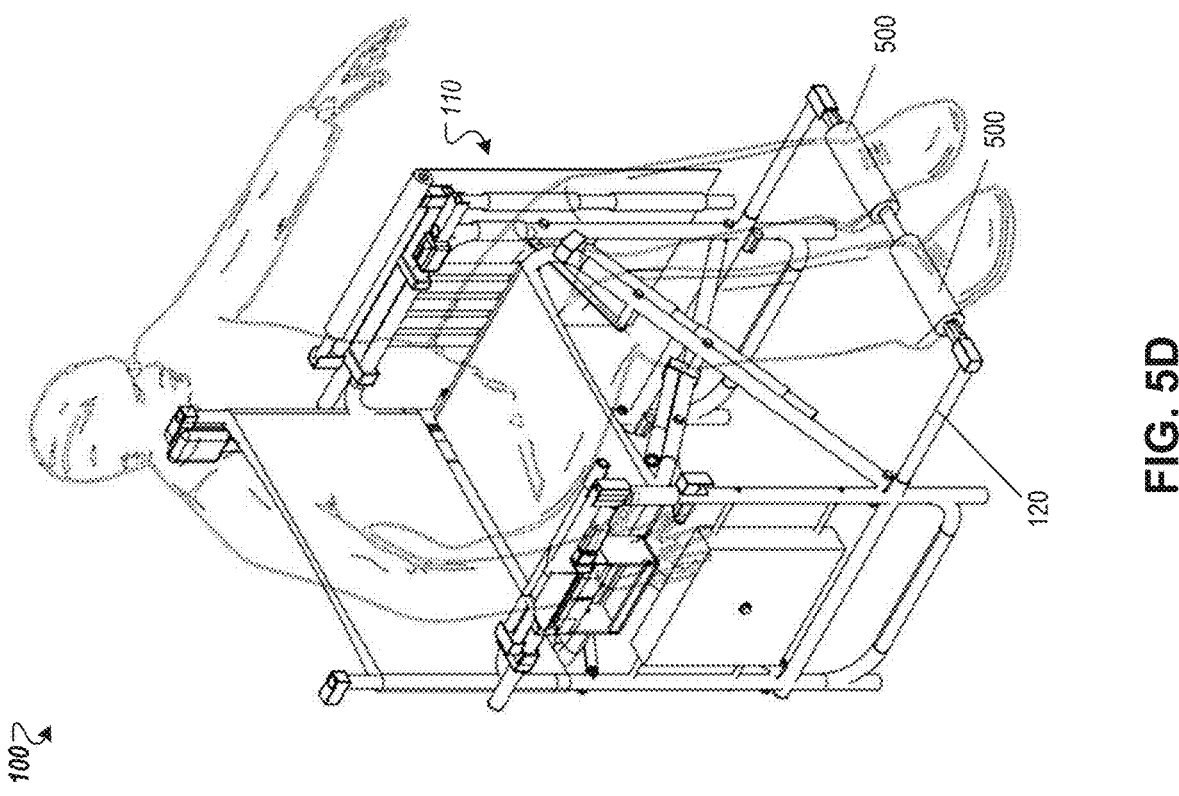
Figure 5C:
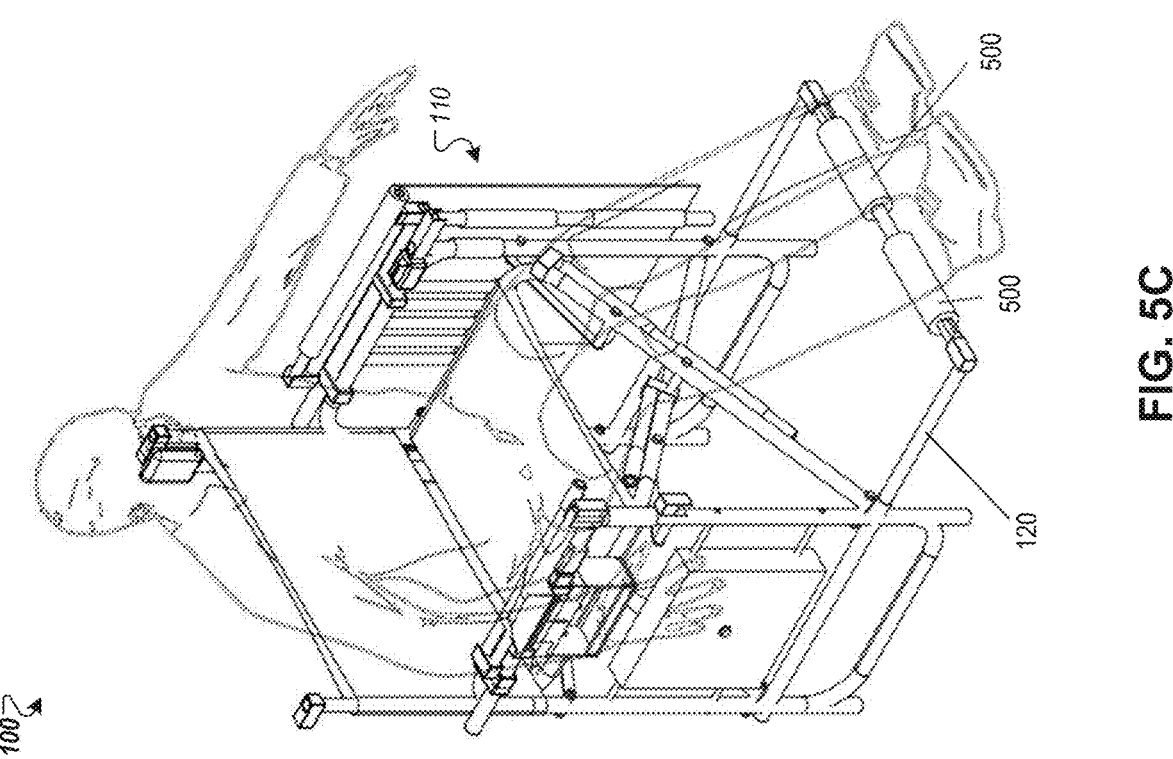
Figure 5F:
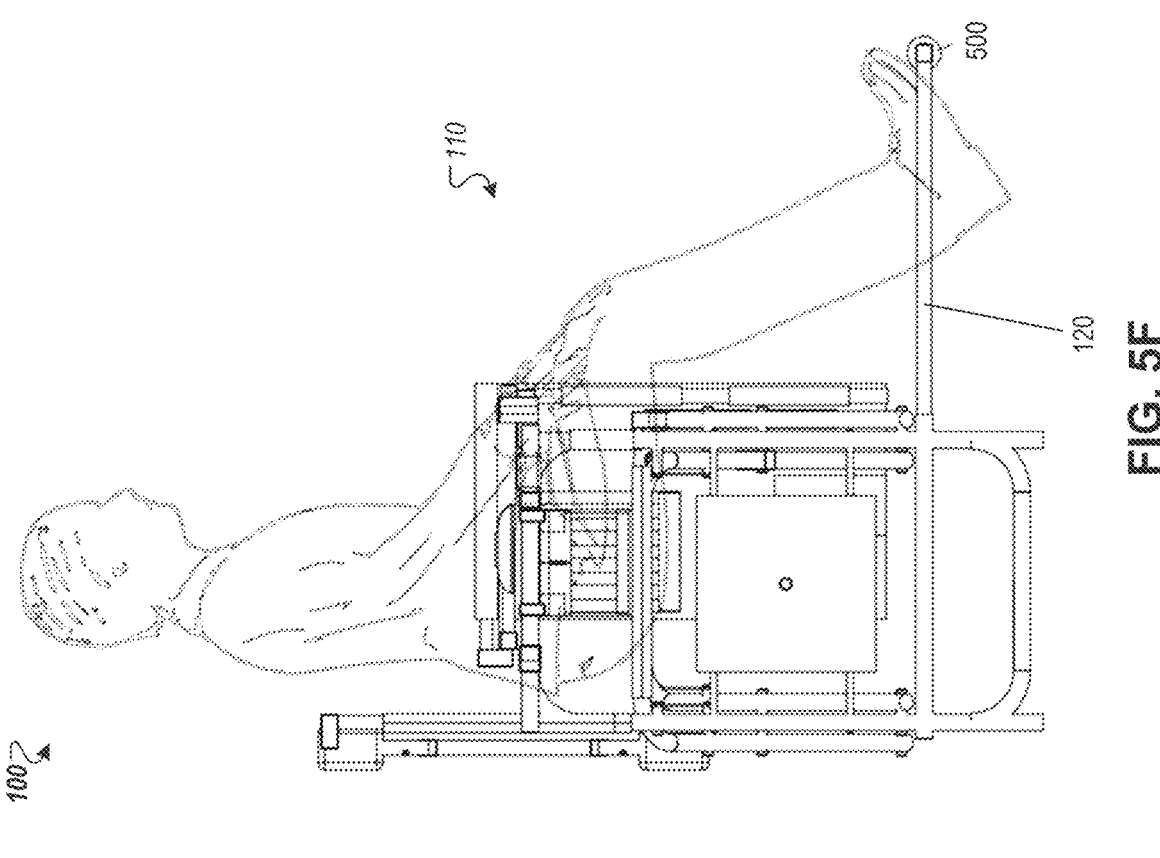
Figure 5E:
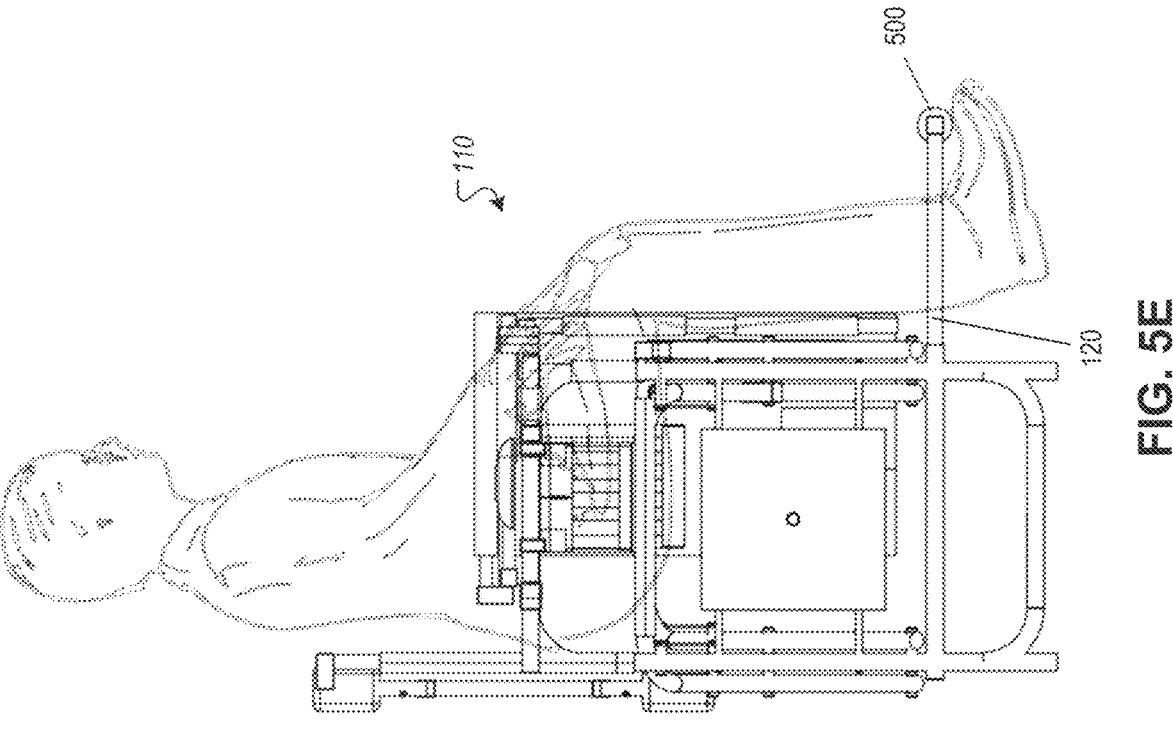
Figures 5G, 5H:
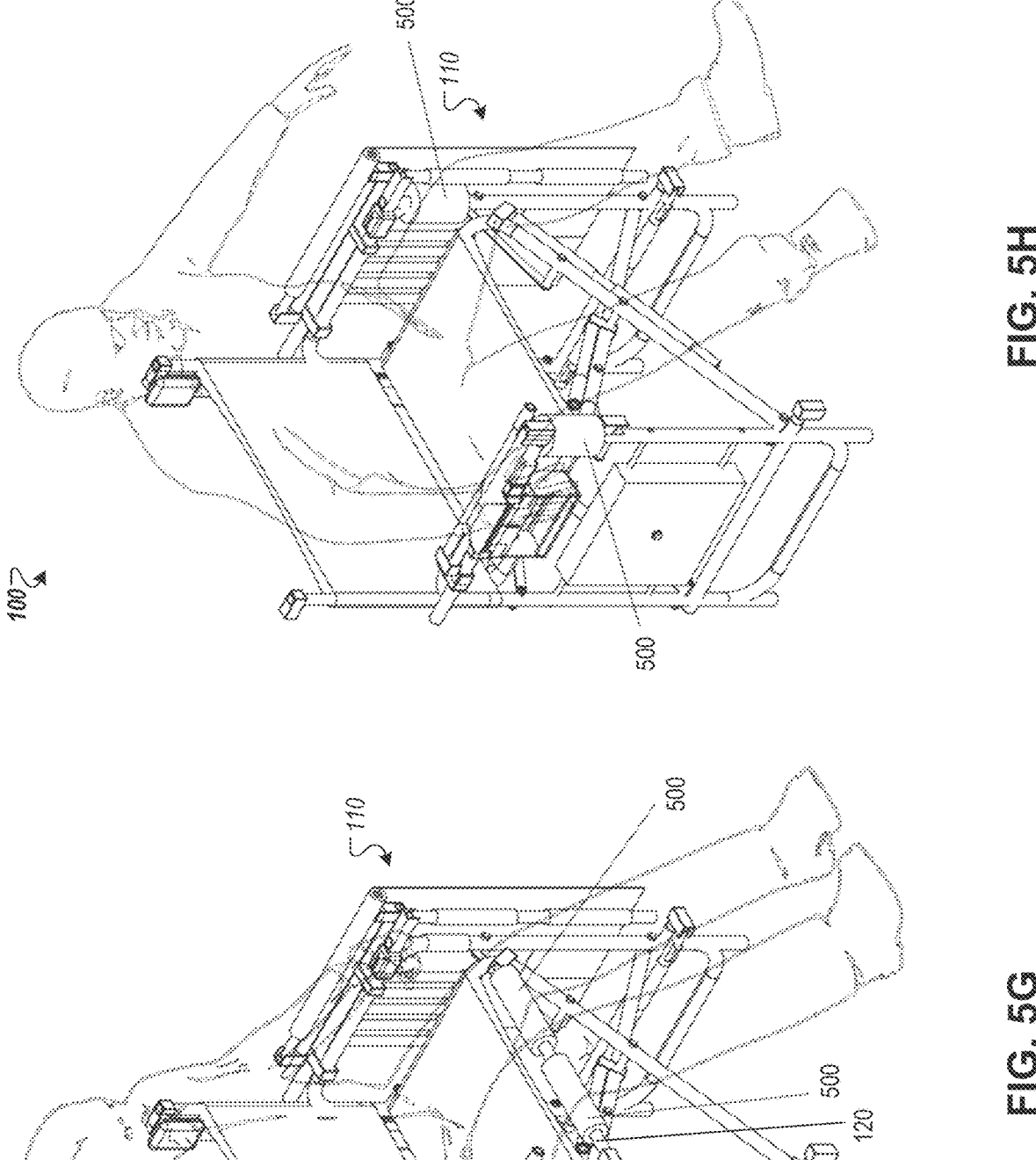
Figures 5I, 5J:
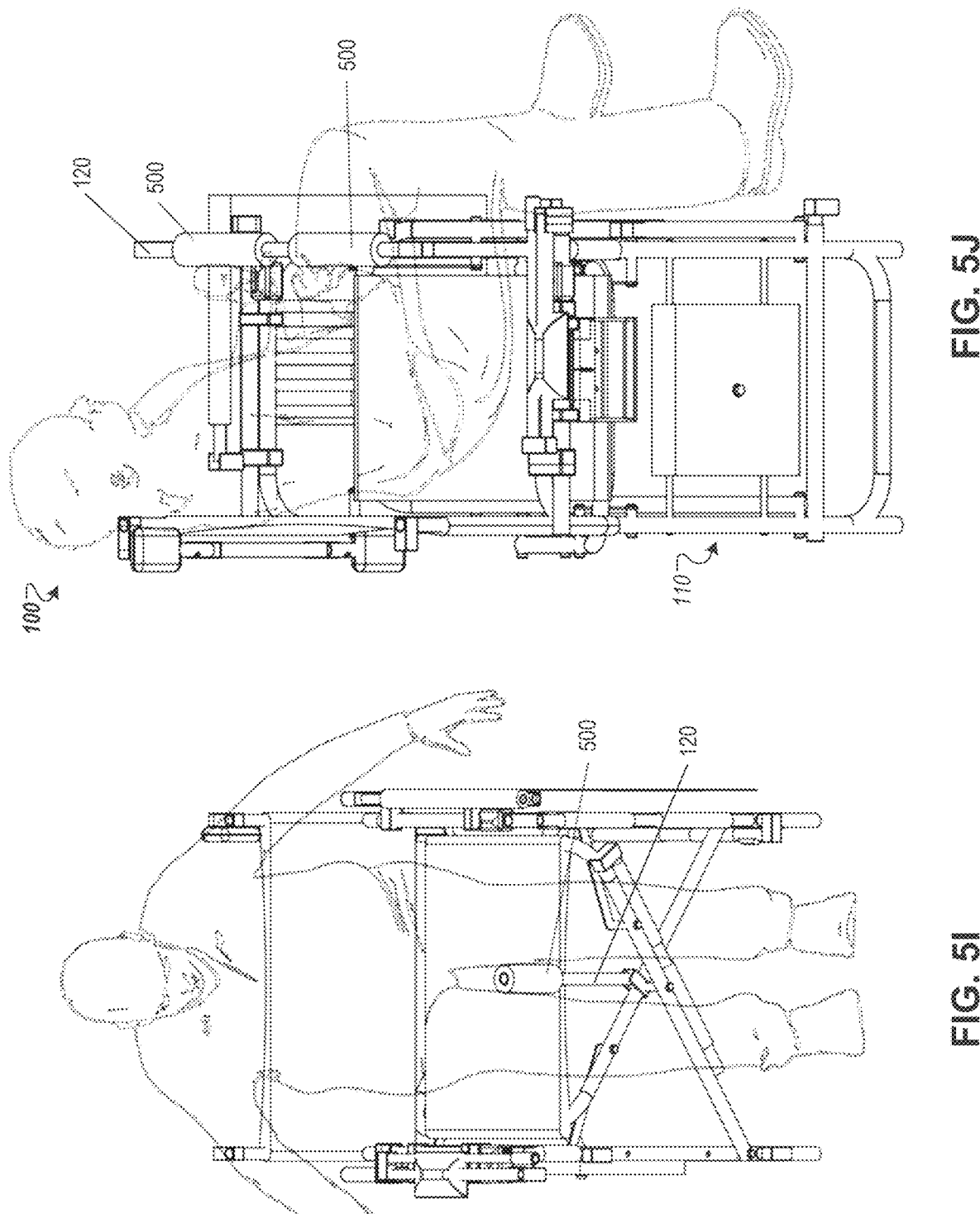
Figure 5L:
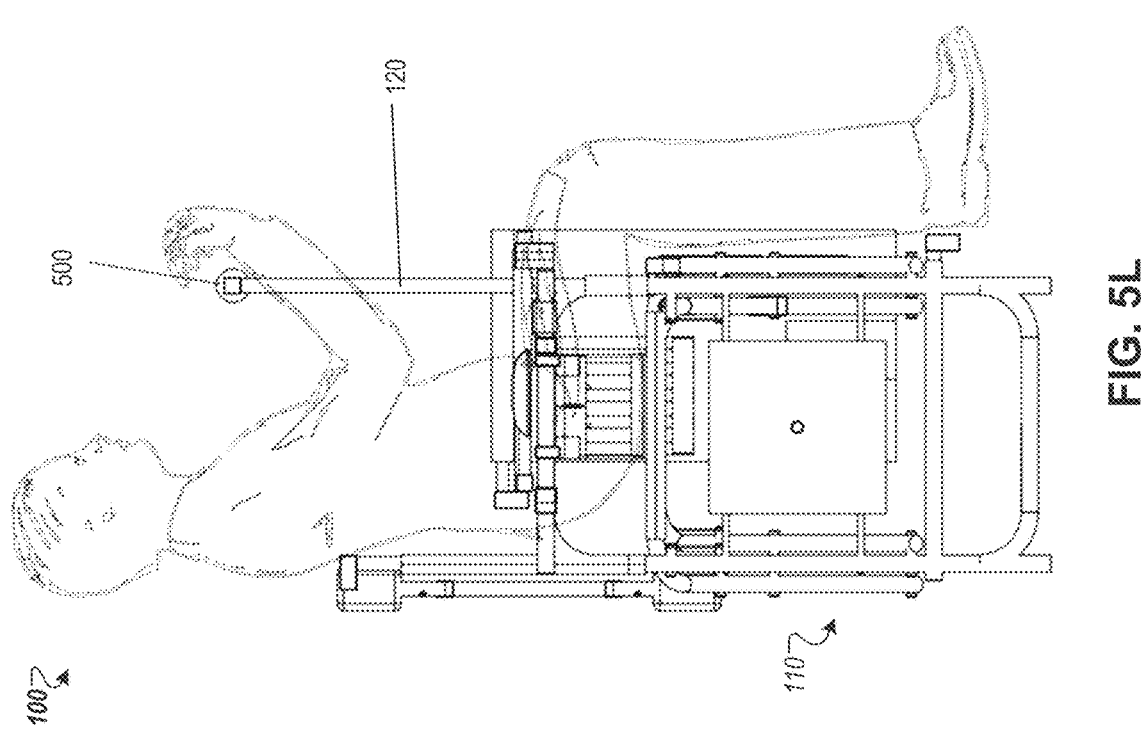
Figure 5K:
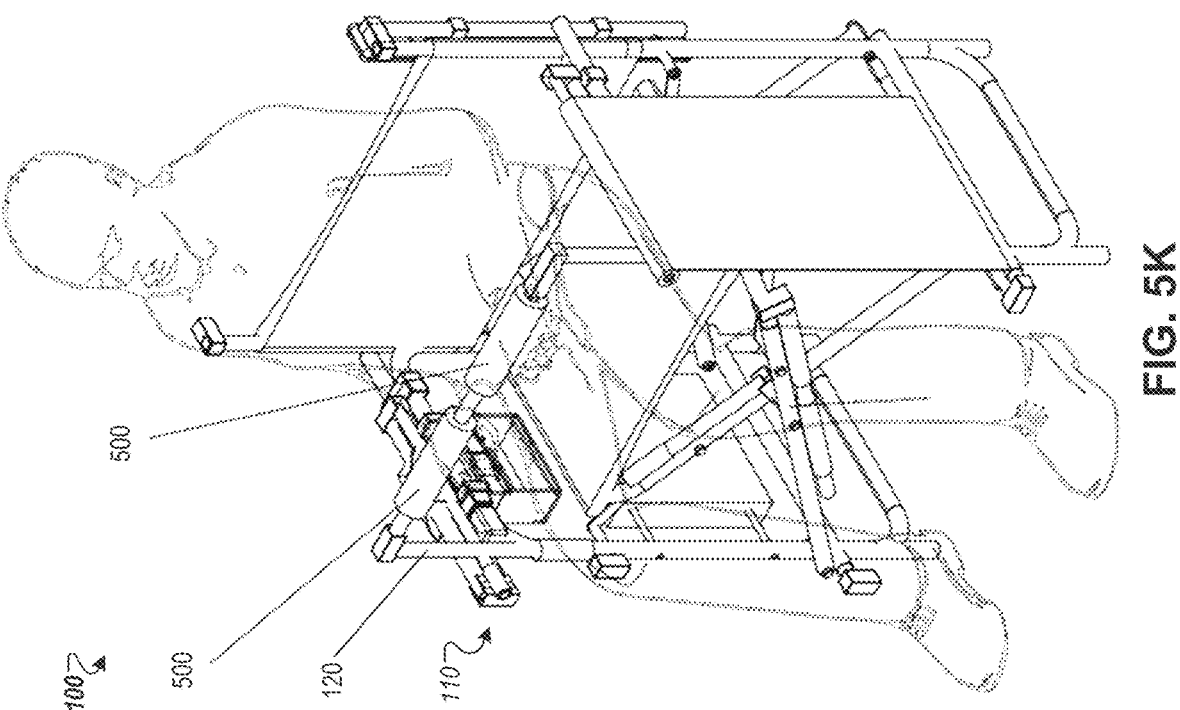
Figure 5N:
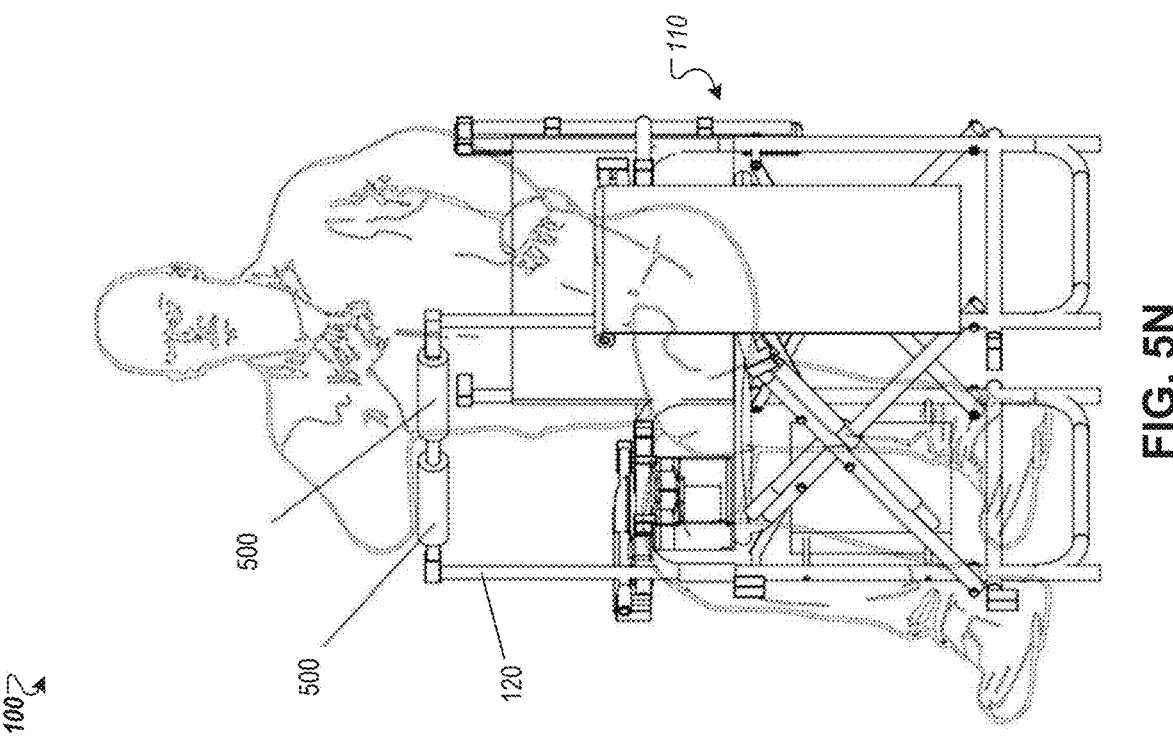
Figure 5M:
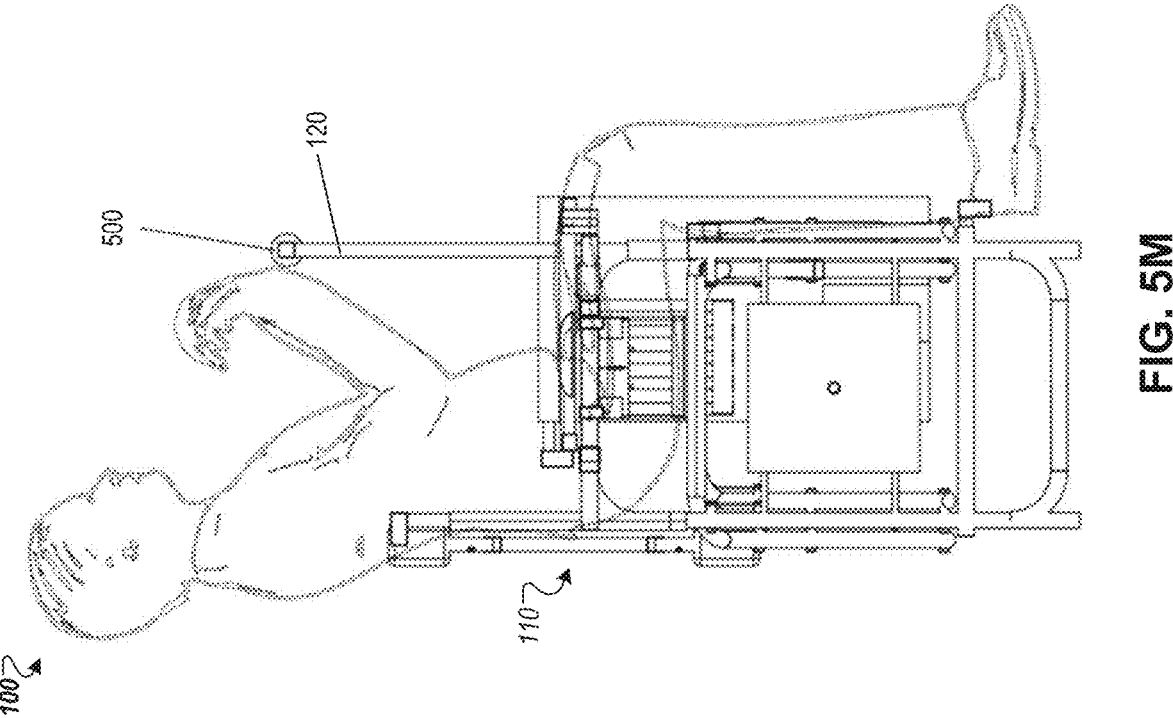
Figure 5P:
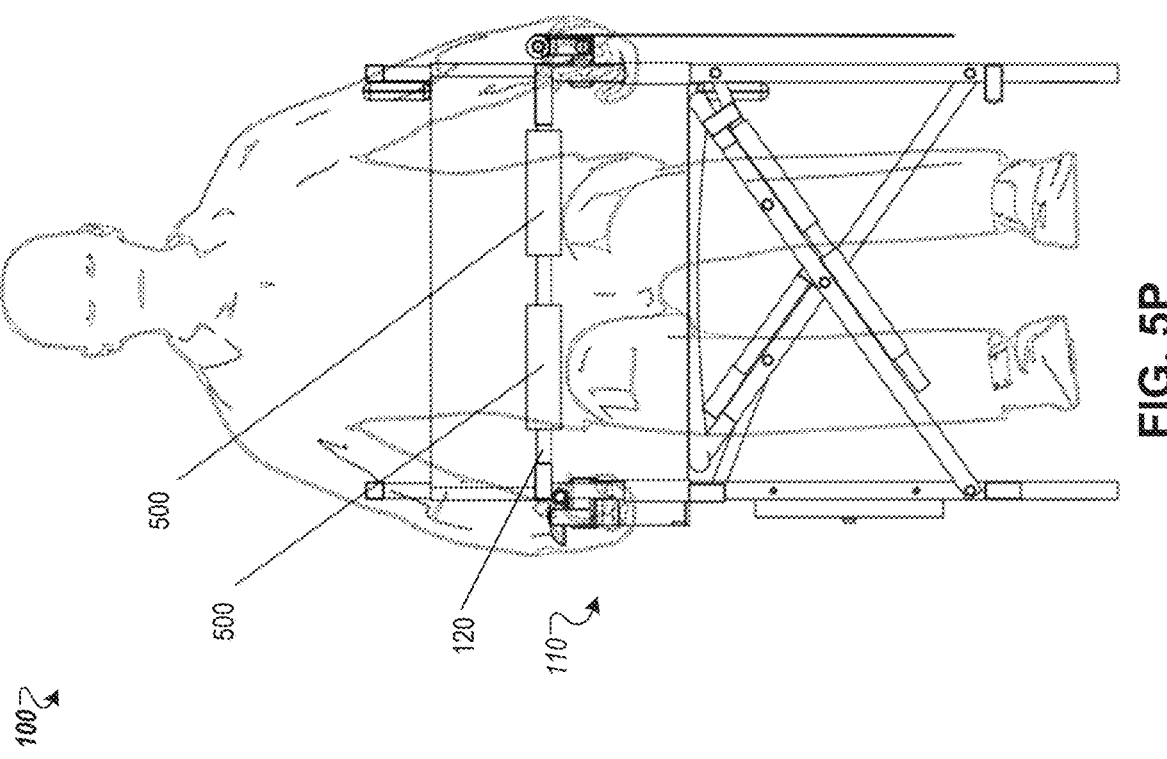
Figure 5O:
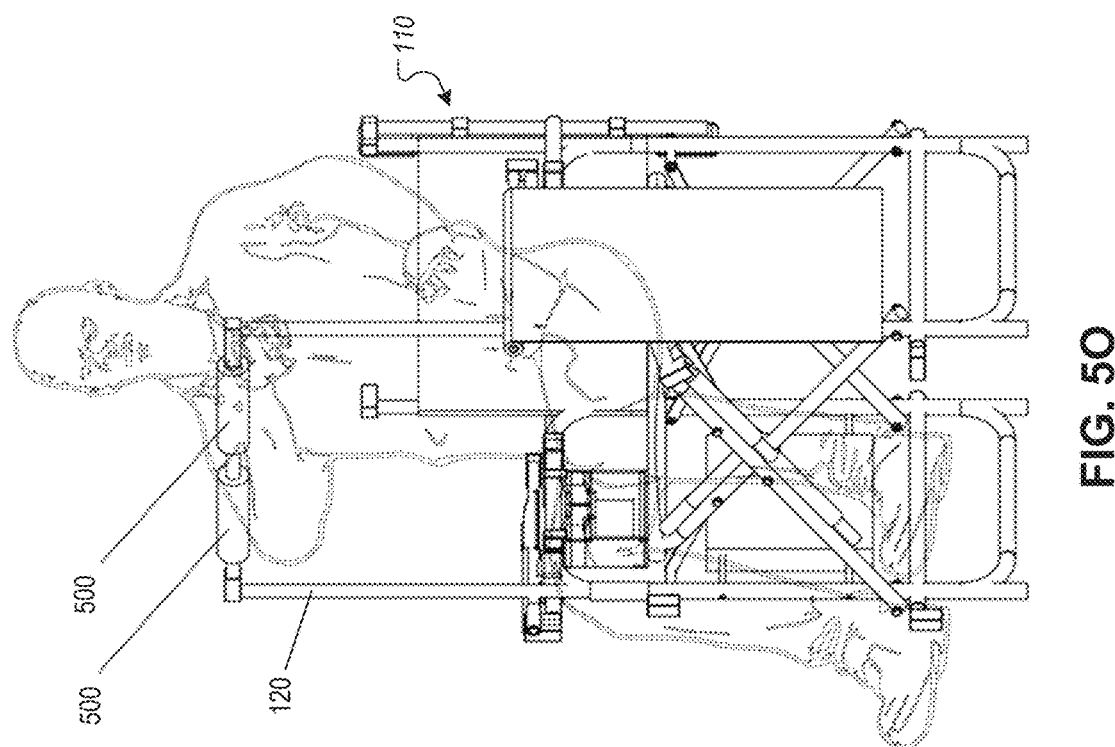
Figures 5Q, 5R:
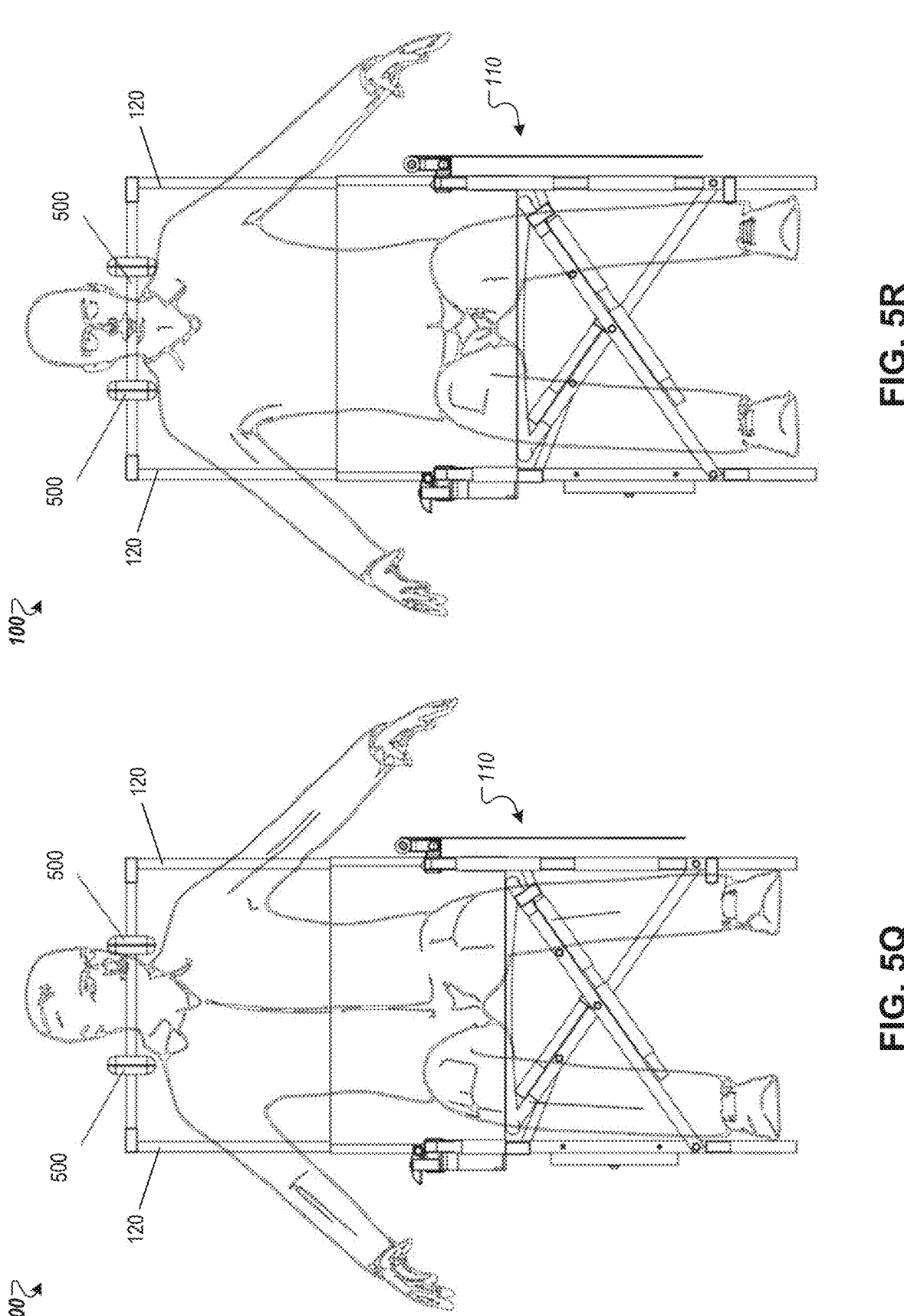
Figures 5S, 5T:
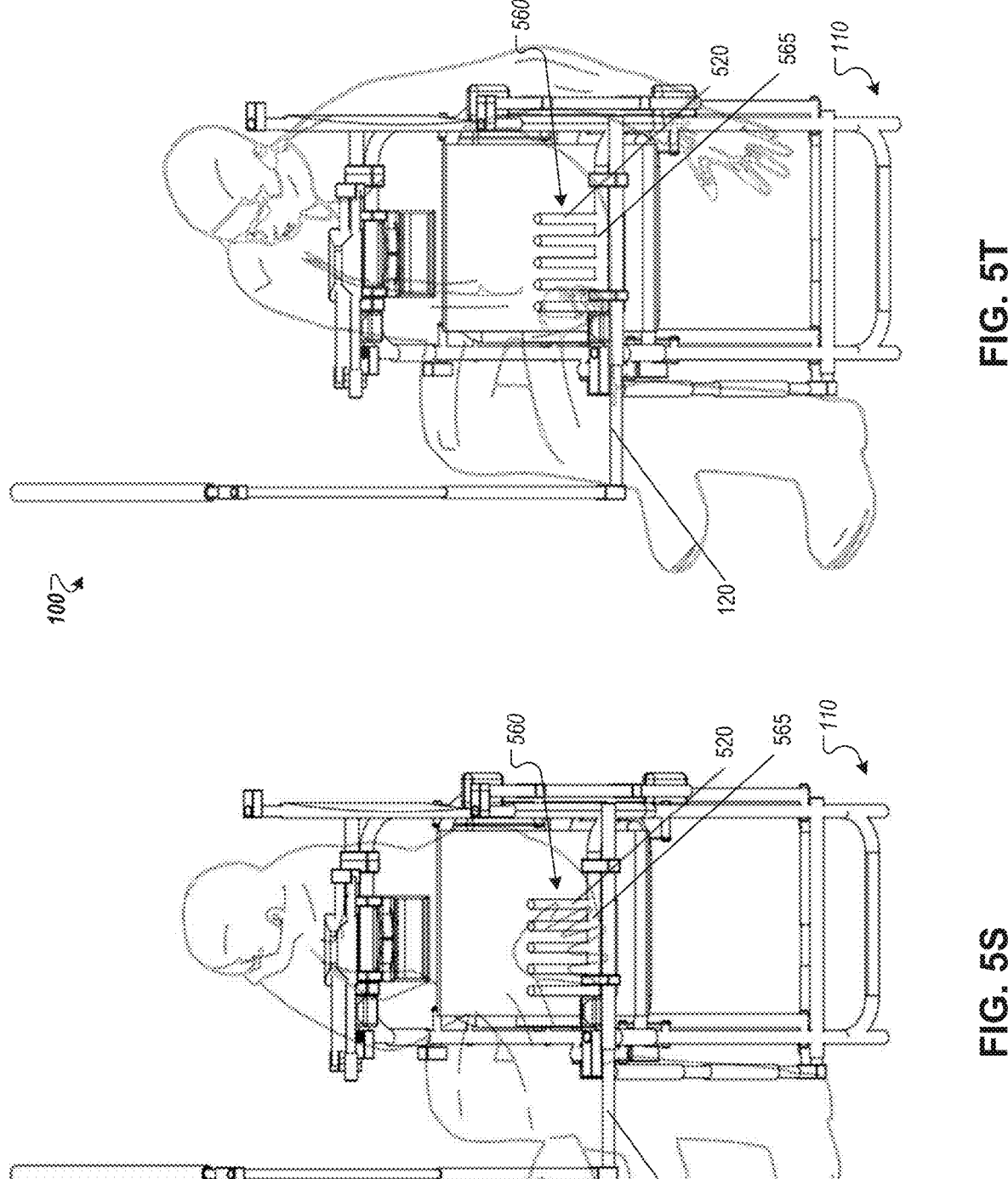

FIGS. 5A-T illustrate strength assessment module devices 500, according to certain embodiments. FIG. 5A-B illustrate perspective views of the strength assessment module device 500, according to some embodiments. FIGS. 5C-F illustrate perspective views of a patient using the neurological examination system 100, including the strength assessment module device 500 positioned at the bottom of the patient placement module 110, according to some embodiments. FIGS. 5G-I illustrate perspective views of a patient using the neurological examination system 100, including the strength assessment module device 500 positioned near the middle and sides of the patient placement module 110, according to some embodiments. FIGS. 5I-P illustrate perspective views of a patient using the neurological examination system 100, including the strength assessment module device 500 positioned near the middle of the patient placement module 110, according to some embodiments. FIGS. 5Q-R illustrate perspective views of a patient using the neurological examination system 100, including the strength assessment module device 500 positioned on two arms of the patient placement module 110, according to some embodiments. FIGS. 5S-T illustrate perspective views of a patient using the neurological examination system 100, including the strength assessment module device 500 and one or more inflatable bags 520, according to some embodiments. FIGS. 5C-T show substantially similar components as those illustrated in FIGS. 5A-B.

In some embodiments, a neurological examination system 100 includes the strength assessment module device 500. The strength assessment module device 500 may be used to measure muscle strength of a patient and may act as a substitute for a motor examination (e.g., assessment of a patient's motor system, including muscle strength, tone, coordination, and/or reflexes). The strength assessment module device 500 may be used to replace pressure sensitivity of a neurological examiner's hand or finger while retaining a natural level of resistance exhibited by a human hand or finger due to its tissue structure and muscle strength. An added benefit of the strength assessment module device 500 is the ability to accurately and consistently provide numerical equivalents of the amount of force applied compared to the neurological examiner's subjective assessment of the amount of force applied.

The strength assessment module device 500 may include a pressure sensor 510, an inflatable bag 520, and/or a pump 530. The inflatable bag 520 may have a solid core 540 in the middle of the inflatable bag 520 to provide a structure similar to a bone. In some embodiments, the solid core 540 may be a rail of the arms 120 of the neurological examination system 100. In other embodiments, the solid core 540 may be separate from the arms 120 and may be attached to the arms 120 by one or more connectors.

The pressure sensor 510, the inflatable bag 520, and the pump 530 may be connected via one or more tubes 550 to create a shared pressure system. The pump 530 may inflate the inflatable bag 520 to a pressure level that, when pushed against, provides a level of resistance similar to that provided by a neurological examiner's hand or finger. When pressure is applied to the inflatable bag 520 (e.g., a patient pushes against the inflatable air bag as directed by an operator), the internal pressure of the shared pressure system increases. The internal pressure of the shared pressure system may be continuously measured by the pressure sensor 510. The internal pressure of the shared pressure system can be used as a proxy to assess the amount of force applied by the patient.

In some embodiments, the strength assessment module device 500 includes a force sensor 535 to measure the amount of pressure and/or force exerted on the strength assessment module device 500. In such embodiments, the force sensor 535 replaces the shared pressure system, and a flexible material 525 replaces the inflatable bag 520. The flexible material 525 may be silicone, rubber, or other similar materials that wrap around the force sensor 535.

The strength assessment module device 500 may include a set of one or more strength assessment module devices 500 that may be distributed into different areas around the patient situated in the patient placement module 110. In some embodiments, two strength assessment module devices 500 are located near the bottom of the patient placement module 110, as illustrated in FIGS. 5C-E. In such embodiments, the two strength assessment module devices 500 are attached to an arm 120 configured to extend from a base portion of the patient placement module 110 toward a patient's feet and/or ankles. When arranged this way, the strength assessment module device 500 is at a base level (e.g., Level 0).

Strength assessment module devices 500 in a Level 0 configuration may be used to assess knee flexion (e.g., patient places their legs in front of the strength assessment module devices 500 and pushes their legs back against resistance, as seen in FIG. 5C), knee extension (e.g., patient places their legs behind the strength assessment module devices 500 and pushes their legs forward against resistance, as seen in FIG. 5D), dorsiflexion (e.g., patient places dorsal aspects of their feet (e.g., toes) behind the strength assessment module devices 500 and pushes up against resistance, as seen in FIG. 5E), and plantar flexion (e.g., patient places plantar aspects of their feet (e.g., the ball of the foot) on the strength assessment module devices 500 and pushes down against resistance, as seen in FIG. 5F).

In some embodiments, five strength assessment module devices 500 are located near the middle and sides of the patient placement module 110, as illustrated in FIGS. 5G-I. In such embodiments, the five strength assessment module devices 500 are attached to an arm 120 positioned below a patient's thighs and/or knees and/or to a portion of the patient placement module 110 itself. When arranged this way, the strength assessment module device 500 is at a first level (e.g., Level 1).

Strength assessment module devices 500 in a Level 1 configuration may be used to assess hip flexion (e.g., patient places their thighs on the strength assessment module devices 500 and pushes down against resistance, as seen in FIG. 5G), hip abduction (e.g., patient places their thighs on the strength assessment module devices 500 and pushes toward both sides against resistance, as seen in FIG. 5H), and hip adduction (e.g., patient places their inner thighs on the strength assessment module device 500 and squeezes inward against resistance, as seen in FIG. 5I).

In some embodiments, two strength assessment module devices 500 are located near the middle of the patient placement module 110, as illustrated in FIGS. 5J-P. In such embodiments, the two strength assessment module devices 500 are attached to an arm 120 that is positioned near a patient's midsection and extends horizontally across the patient placement module 110. When arranged this way, the strength assessment module device 500 is at a second level (e.g., Level 2).

Strength assessment module devices 500 in a Level 2 configuration may be used to assess wrist flexion (e.g., patient places the palmar aspects of their hands on the strength assessment module devices 500 and flexes their wrist against resistance, as seen in FIG. 5J), wrist extension (e.g., patient places the dorsal aspects of their hands on the strength assessment module devices 500 and extends their wrist against resistance, as seen in FIG. 5K), elbow flexion (e.g., patient bends their elbows to a ninety-degree angle while keeping their palms directed upwards, places their forearms under the strength assessment module devices 500, and flexes their forearms against resistance, as seen in FIG. 5L), elbow extension (e.g., patient bends their elbows to a ninety-degree angle while keeping their palms directed upwards, places their forearms above the strength assessment module devices 500, and flexes their forearms against resistance, as seen in FIG. 5M), shoulder adduction (e.g., patient flexes their arm at the elbow while the arm is held out from the body, places the middle of their upper arm on the strength assessment module devices 500, and adducts their shoulder against resistance, as seen in FIG. 5N), shoulder abduction (e.g., patient flexes their arm at the elbow while the arm is held out from the body, places the middle of their upper arm under the strength assessment module devices 500, and abducts their shoulder against resistance, as seen in FIG. 5O), and hip flexion (e.g., patient places their thigh under the strength assessment module device 500 and lifts their thighs upward against resistance, as seen in FIG. 5P).

In some embodiments, two strength assessment module devices 500 are located on two separate arms 120 near the top of the patient placement module 110, as illustrated in FIGS. 5Q-R. In such embodiments, the two strength assessment module devices 500 are attached to two arms 120 that are positioned near a patient's head and extends horizontally across the patient placement module 110. When arranged this way, the strength assessment module device 500 is at a third level (e.g., Level 3).

Strength assessment module devices 500 in a Level 3 configuration may be used to assess the accessory nerve (i.e., CN XI, cranial nerve 11, spinal accessory nerve). The accessory nerve is a motor nerve that controls the movement of the sternocleidomastoideopezius muscles, which are responsible for head rotation, shoulder elevation, and certain neck movements. The sternocleidomastoideole assists with head rotation and tilting, and the trapezius muscle assist in shoulder elevation (e.g., shrugging) and scapular movement. In some embodiments, the accessory nerve is assessed by a patient placing one of their cheeks on the strength assessment module 500 and turning their head to the side against resistance, as seen in FIG. 5Q. In other embodiments, the accessory nerve is assessed by a patient placing their shoulders under the strength assessment module 500 and shrugging their shoulders against resistance, as seen in FIG. 5R.

In addition to the previously discussed levels of the strength assessment module devices 500, there may be a framed strength assessment module device 560 located under and/or over the armrest area. Compared to the four levels of the strength assessment module devices 500, the following strength assessment module device 500 contains several inflatable bags 520 with solid core cylinders 540 in the middle to simulate human fingers, and a frame 565 used to hold them. In some embodiments, the strength assessment module device 500 held by the frame 565 contains force sensors (e.g., the force sensor 535 of FIG. 5B) wrapped around solid core cylinders 540 and covered by flexible material (e.g., the flexible material 525 of FIG. 5B). In some embodiments, the framed strength assessment module device 560 is used to evaluate the intrinsic muscles of the hand when a patient puts their hand in the framed strength assessment module device 560 and spreading their fingers against resistance, then squeezing their fingers together, as seen in FIG. 5S. In some embodiments, the framed strength assessment module device 560 is used to evaluate the flexors of the fingers when a patient makes a first and squeezes one of the inflatable bags 520 within the framed strength assessment module device 560 with their whole hand, as seen in FIG. 5T.

Figure 6:
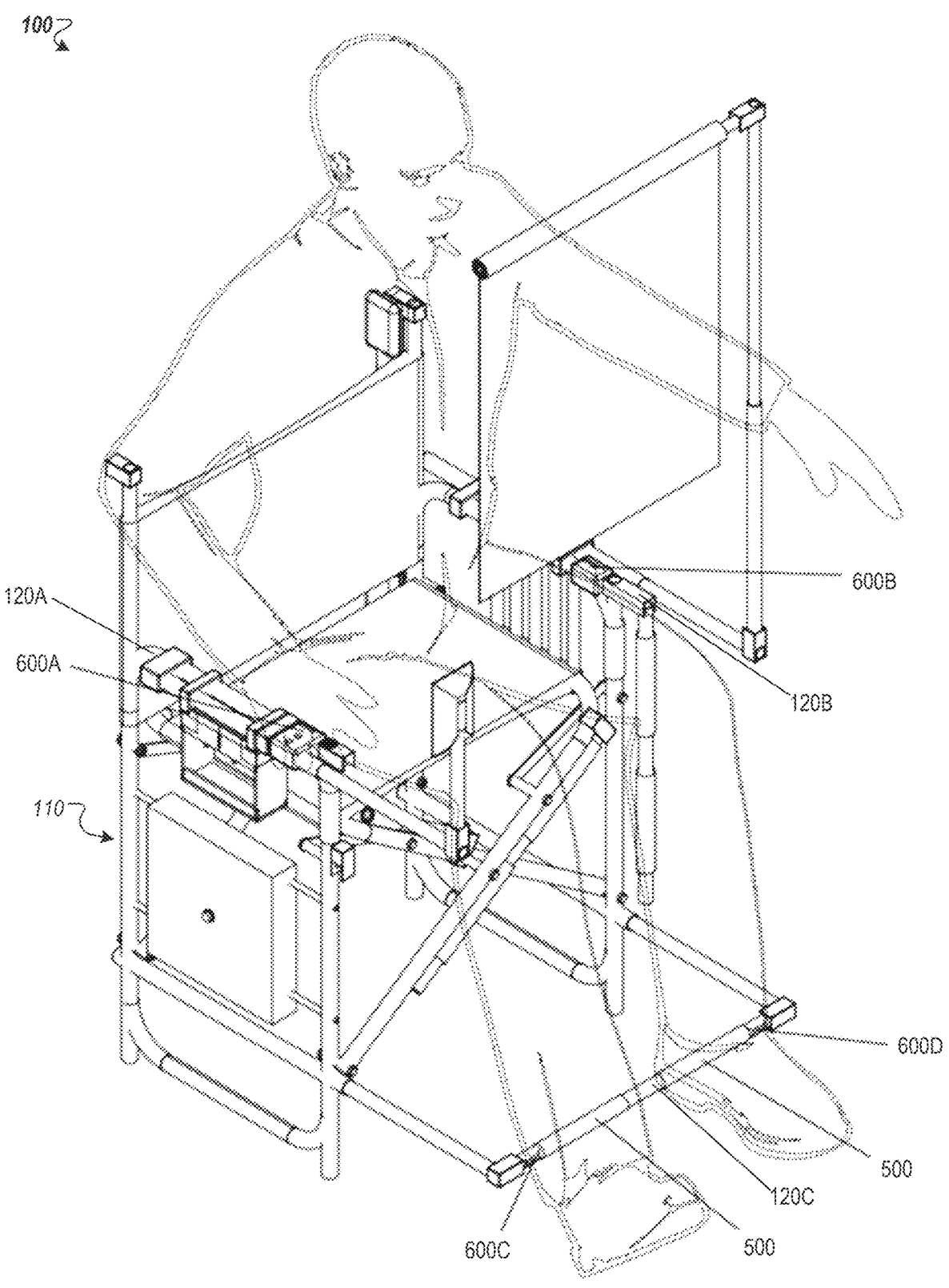
FIG. 6 illustrates sensory assessment module devices, according to certain embodiments.

FIG. 6 illustrates sensory assessment module devices 600. according to certain embodiments. In some embodiments, the neurological examination system 100 includes the sensory assessment module device 600 used to assess pain, temperature, and/or vibratory sensation. During conventional neurological examination, the neurological examiner uses a pin and a tuning fork, which is usually perceived as cold to the touch, to assess pain and temperature sensation, respectively. A vibrating tuning fork is used to assess vibratory sensation.

The sensory assessment module device 600 replaces a tuning fork with a vibrating component including a vibration motor with a vibration frequency equaling that of a tuning fork and a plate that transmits vibration to a patient. Heating and/or cooling component contains heating and/or cooling element that transmits heat/cold to a plate and replaces cold to the touch tuning fork and allows for assessing the temperature sensation.

In some embodiments, four sensory assessment module devices 600A-D are positioned around a patient, with two sensory assessment module devices 600A-B positioned at the ends of the arms 120A-B positioned on either side of the patient placement module 110, and another two sensory assessment module devices 600C-D positioned at the ends of the arm 120C positioned near the bottom of the patient placement module 110. In FIG. 6, a patient is shown positioning their right palm and big toe of their right foot on the sensory assessment module devices 600A and 600C, respectively.

Figures 7A, 7B:
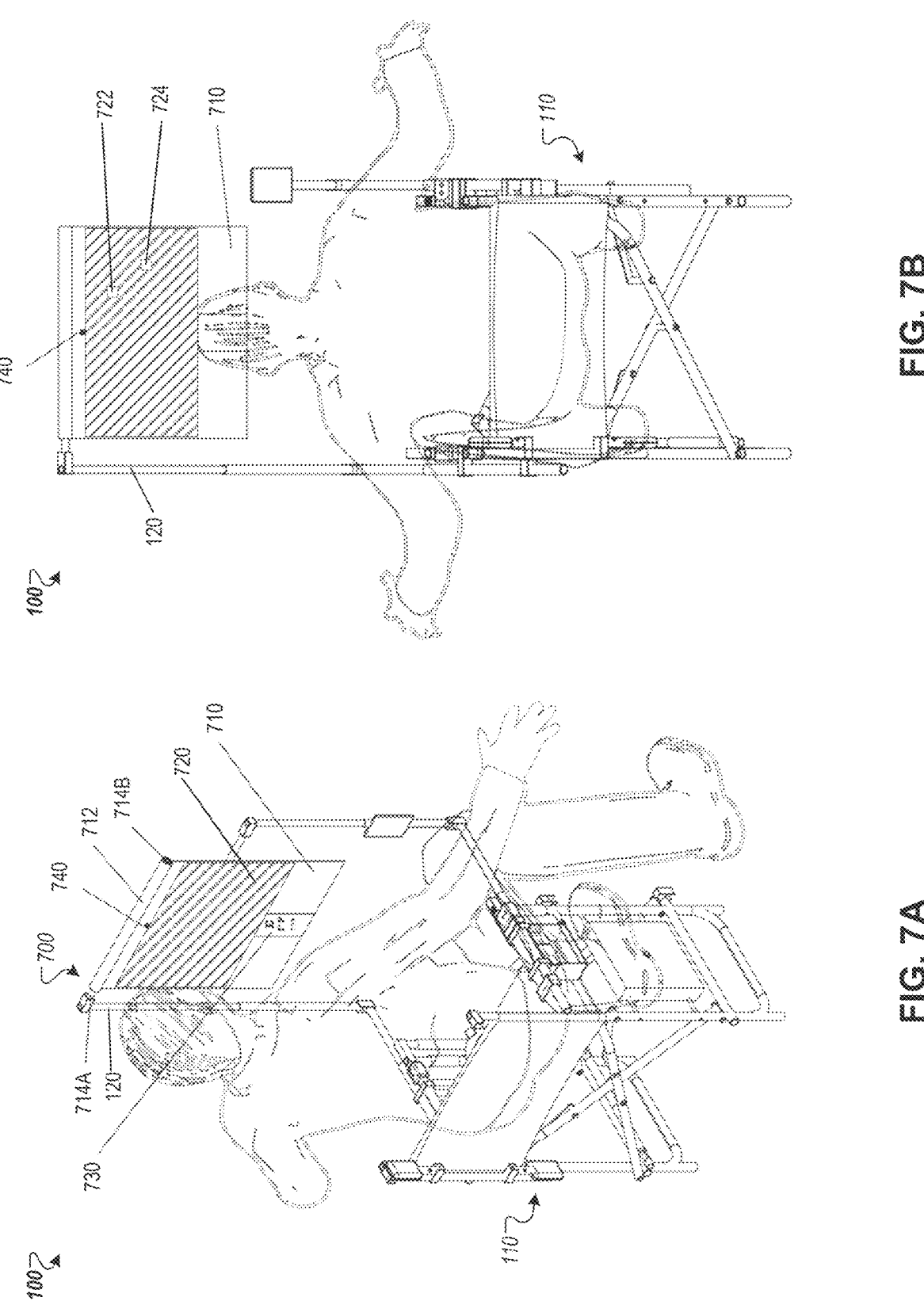
FIGS. 7A-C illustrate views of ocular assessment module systems, according to certain embodiments.
Figure 7C:
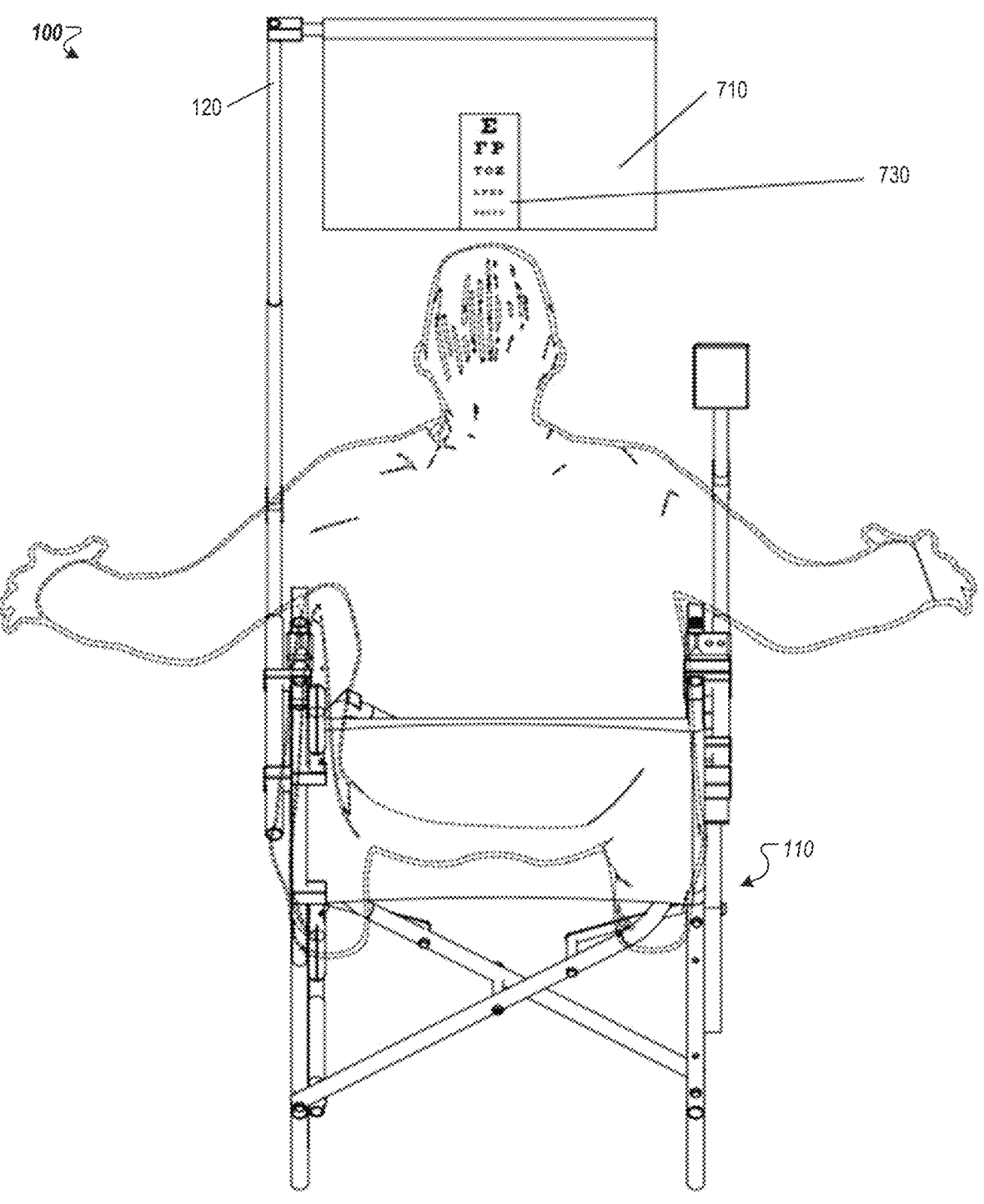

FIGS. 7A-C illustrate views of ocular assessment module systems 700, according to certain embodiments. FIG. 7A illustrates a perspective view of the neurological examination system 100 with the ocular assessment module system 700, including a flexible screen 710 and a scaled Snellen chart 730, according to one embodiment. FIG. 7B illustrates a front view of the flexible screen 710, including a focus point 722, according to one embodiment. FIG. 7C illustrates a front view of the Snellen chart 730, according to one embodiment. FIGS. 7B-C show substantially similar components as those illustrated in FIG. 7A.

In some embodiments, the ocular assessment module system 700 is used to assess the functioning of the optic nerve (i.e., CN II, second cranial nerve, visual nerve). The optic nerve carries visual impulses from the eye to the optical cortex of the brain; the oculomotor nerve (i.e., CN III, third cranial nerve), which controls most eye movements, pupil constriction, and eyelid elevation; the trochlear nerve (i.e., CN IV, fourth cranial nerve), which controls the superior oblique muscle, allowing the eye to move downward and inward; and the abducens nerve (i.e., CN VI, sixth cranial nerve), which controls the lateral rectus muscle, responsible for abducting the eye (e.g., moving it outward/laterally). Extraocular muscles and pupillary reflex are mediated by CN II and CN III.

During conventional neurological examination, the neurological examiner has the patient track his finger/pen to assess eye movement, ocular pursuit, primary gaze, and fields of vision. The neurological examiner uses a pen light to shine the light into patient's eyes and assesses pupillary reflex. The neurological examiner also uses a Snellen chart (e.g., a standardized eye chart used to measure visual acuity) to assess the clarity or sharpness of vision.

The ocular assessment module system 700 may perform tests such as mentioned above using a matrix of individual dots and/or Snellen chart lines and/or symbols that are controlled by an operator. This allows an operator to simulate both a finger as a focus point using a dot with a particular color and pen light with a bright white dot. Brightness of the dots can be controlled by an operator to adjust brightness as needed for different environmental conditions and to achieve the desired effect on the patient's eye. In addition to an option to manually control dots, a set of predefined patterns may be provided by an application, such as an automatic "H-pattern" and/or a "plus" pattern. Operators have an option to create and save their own patterns for future use.

A matrix of individual dots and/or Snellen chart lines/symbols can be flat or curved, soft or rigid. It may be represented by a matrix of light emitting diode ("LEDs") and a scaled version of a Snellen chart or a computer screen. The matrix may be positioned at a precise distance away from the patient placement module 110 with or without the help of the arms 120. In addition, the ocular assessment module system 700 may include a camera 740 to allow for recording, interpretation, and/or transmission of the examination. If the camera 740 is used to interpret the examination and/or parts of the examination, the processing device may process the image received from camera 740 and provide a quantitative assessment of the tests such as ocular pursuit, fields of vision, pupillary reflex, primary gaze, and/or ocular movements.

In some embodiments, the ocular assessment module system 700 includes a flexible screen 710 with LEDs 720 in the top portion of the flexible screen 710 and a scaled Snellen chart 730 in the bottom portion of the flexible screen 710. The LEDs 720 may be configured to emulate a focus point 722 and/or a pen light 724. The flexible screen 710 may be attached to a screen tube 712 attached to an arm 120 via a two sets of bearings 714A-B. In some embodiments, the flexible screen 710 is configured to roll into a compact roll via the bearings 714A-B. The ocular assessment module system 700 may further include a camera 740.

In some embodiments, the ocular assessment module system 700 also functions as a facial nerve assessment module device. The facial nerve assessment module device may replace a facial symmetry assessment (fascial droop and/or smile symmetry, eye closure, eyebrow raise and/or forehead wrinkles) performed by a neurological examiner. The facial nerve assessment module device may use a camera (e.g., camera 740 of FIG. 7A) to scan and evaluate facial symmetry. The processing device may process an image received from the camera 740 and provide a quantitative assessment of the facial symmetry of the patient.

In some embodiments, the ocular assessment module system 700 also functions as a hypoglossal nerve assessment module device, which may replace a tongue deviation assessment performed by a neurological examiner. The hypoglossal nerve assessment module device may use the camera 740 to scan and evaluate tongue deviation. The processing device may process the image received from the camera 740 and provide a quantitative assessment of the tongue deviation of the patient.

Figure 8:
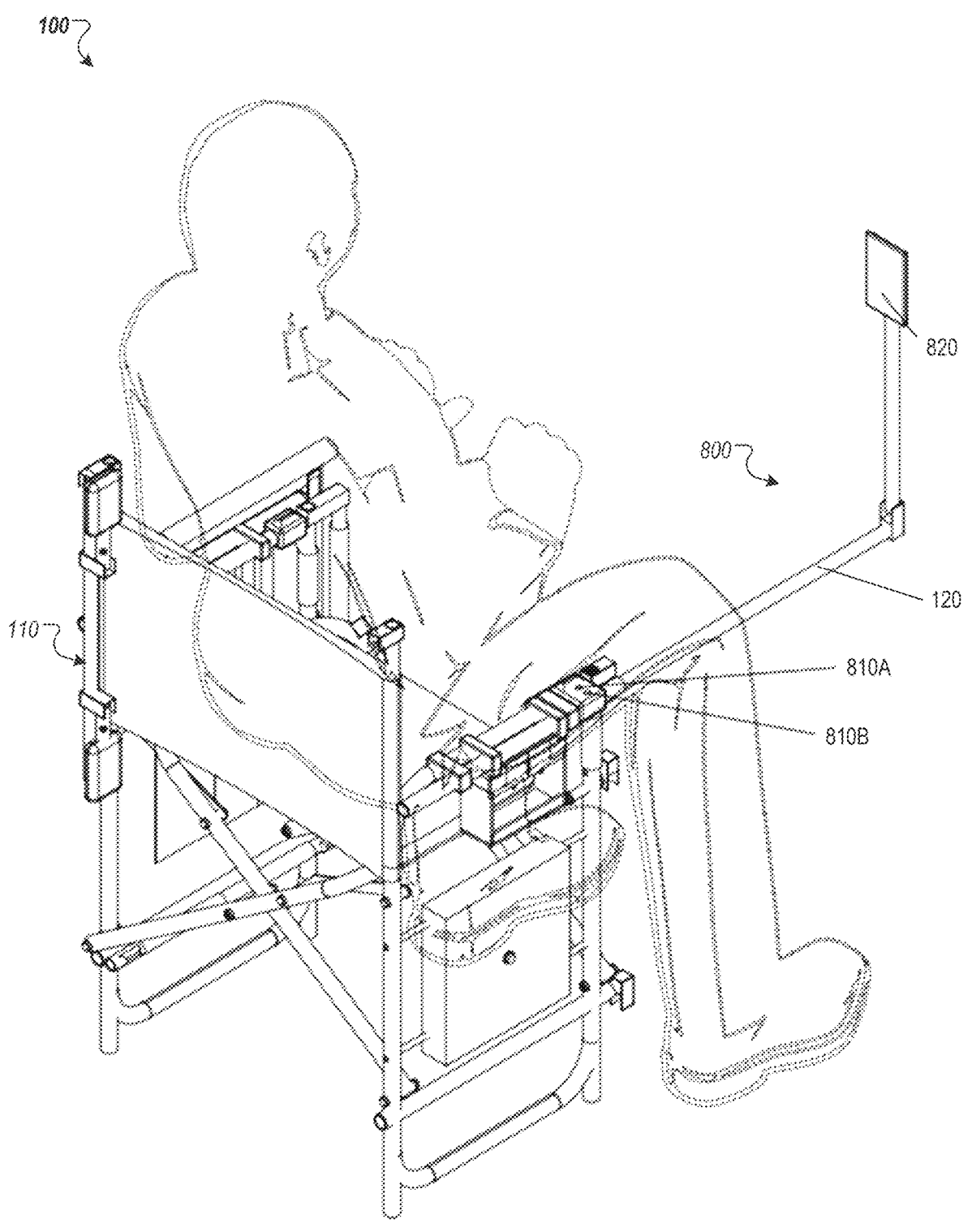
FIG. 8 illustrates a perspective view of the neurological examination system, including an input/output module, according to certain embodiments.

FIG. 8 illustrates a perspective view of a neurological examination system 100, including an input/output (IO) module 800, according to certain embodiments. In some embodiments, the IO module 800 provides additional input and/or output capabilities beyond those provided by video-conferencing devices such as buttons 810A-B and/or a screen 820. In some embodiments, the screen 820 is touch enabled (e.g., responsive to physical touch). Such capabilities, for example, may facilitate the function of the ocular assessment module system (e.g., the ocular assessment module system 700 of FIG. 7) by displaying lines from the Snellen chart 730 and/or use instructions for a patient on a screen of the IO module 800. In some embodiments, the buttons 810A-B and/or the screen 820 is integral to the patient placement module 110 and/or attached to the arms 120.

Figure 9B:
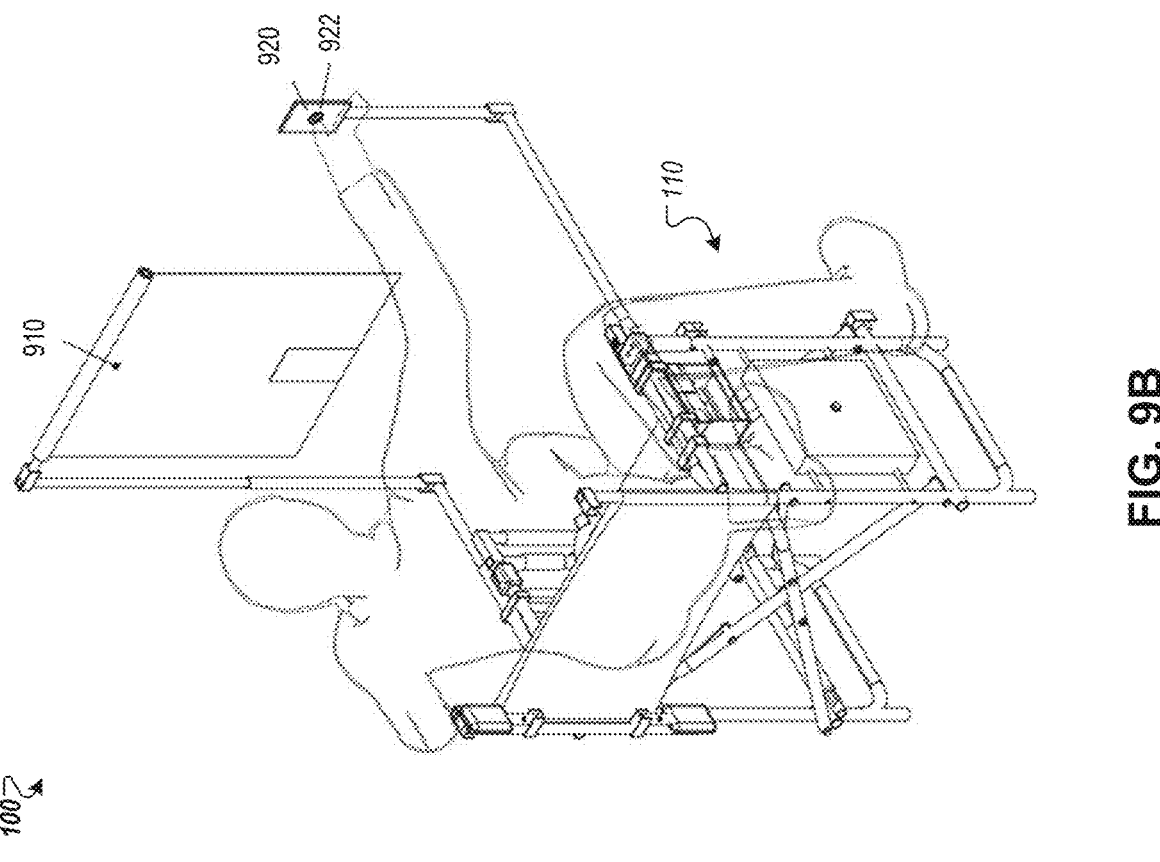
FIGS. 9A-B illustrate perspective views of the neurological examination system, including a coordination assessment module system, according to certain embodiments.
Figure 9A:
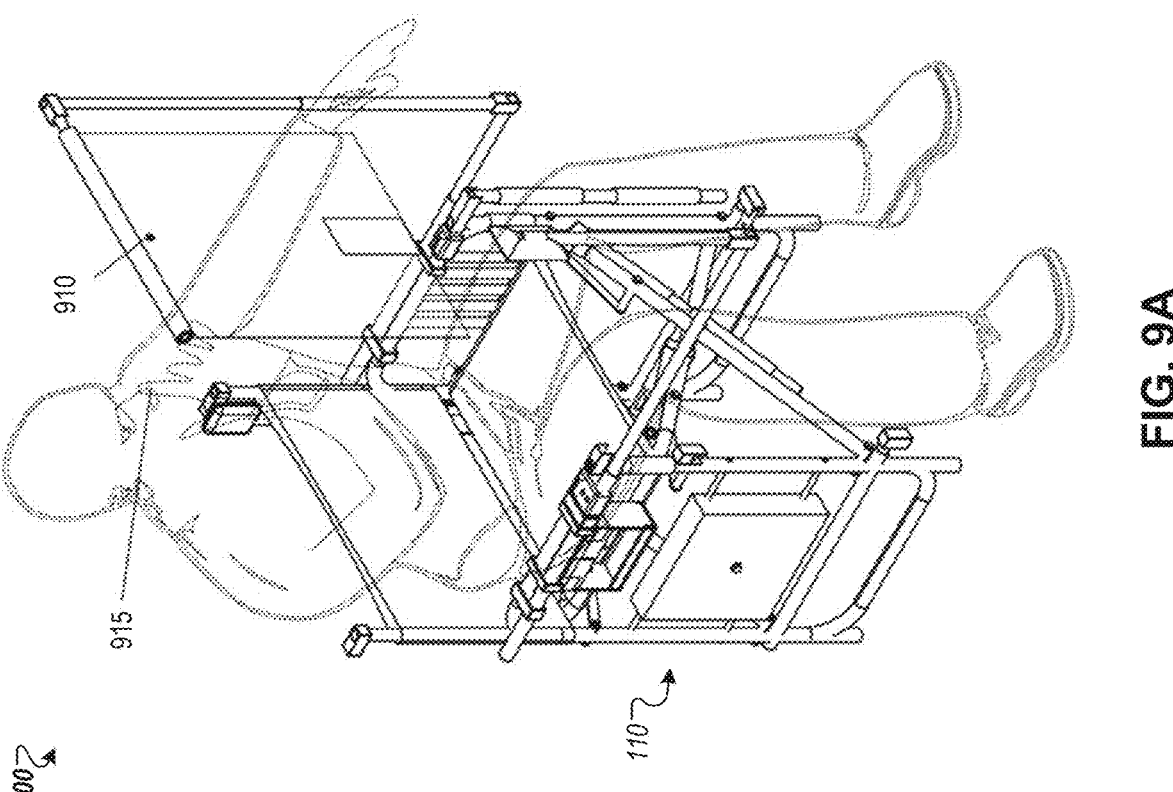

FIGS. 9A-B illustrate perspective views of the neurological examination system 100, including a coordination assessment module system 900, according to certain embodiments. The coordination assessment module system 900 may replace a finger-to-nose and/or a finger-to-finger assessment performed by a neurological examiner. The coordination assessment module system 900 may include a camera 910 and/or a screen 920 used to assess a patient's precision in reaching their nose (e.g., in the finger-to-nose assessment) and/or a virtual target (e.g., in the finger-to-finger assessment). The camera 910 may be the same camera from the ocular assessment module system 700 of FIGS. 7A-B or a separate camera, as seen in FIG. 9A. In some embodiments, the coordination assessment module system 900 may facilitate the finger-to-nose assessment by capturing, by the camera 910 an image of a patient touching their nose 915 with their finger. The screen 920 may be the same screen from the IO module 800 of FIG. 8 or a separate screen, as seen in FIG. 9B. In some embodiments, the coordination assessment module system 900 may facilitate the finger-to-finger assessment by capturing, by one or more sensors of the screen 920, a patient touching a target 922 displayed on the screen 920. In some embodiments, the processing device processes the image received from the camera 910 and/or sensor input from the screen 920 and provides a quantitative assessment of the finger-to-nose motion precision and/or finger-to-finger precision of the patient.

FIG. 10 illustrates a perspective view of the neurological examination system 100, including a videoconferencing device alignment device 1000, according to certain embodiments. In some embodiments, the videoconferencing device alignment device 1000 is used to align and/or secure a camera of a videoconferencing device (e.g., a phone, a tablet, etc.). The camera may be used to conduct a video-conference with an operator of the neurological examination system 100. The alignment device 1000 is configured to align the videoconferencing device's camera in such a way that an operator may communicate and/or see a patient in a manner similar to an in-person neurological examination. Distorted perspective resulting from improper alignment may result in an incorrect interpretation of the subjective assessments performed by the operator. Such assessments include, but are not limited to, the assessments of the oculomotor nerve (i.e., CN III), the trochlear nerve (i.e., CN IV), the abducens nerve (i.e., CN VI), the facial nerve (i.e., CN VII), and/or the hypoglossal nerve (i.e., CN XII).

In some embodiments, the videoconferencing device alignment device 1000 includes a device holder 1010 attached to an arm 120 of the neurological examination system 100.

Figure 11A:
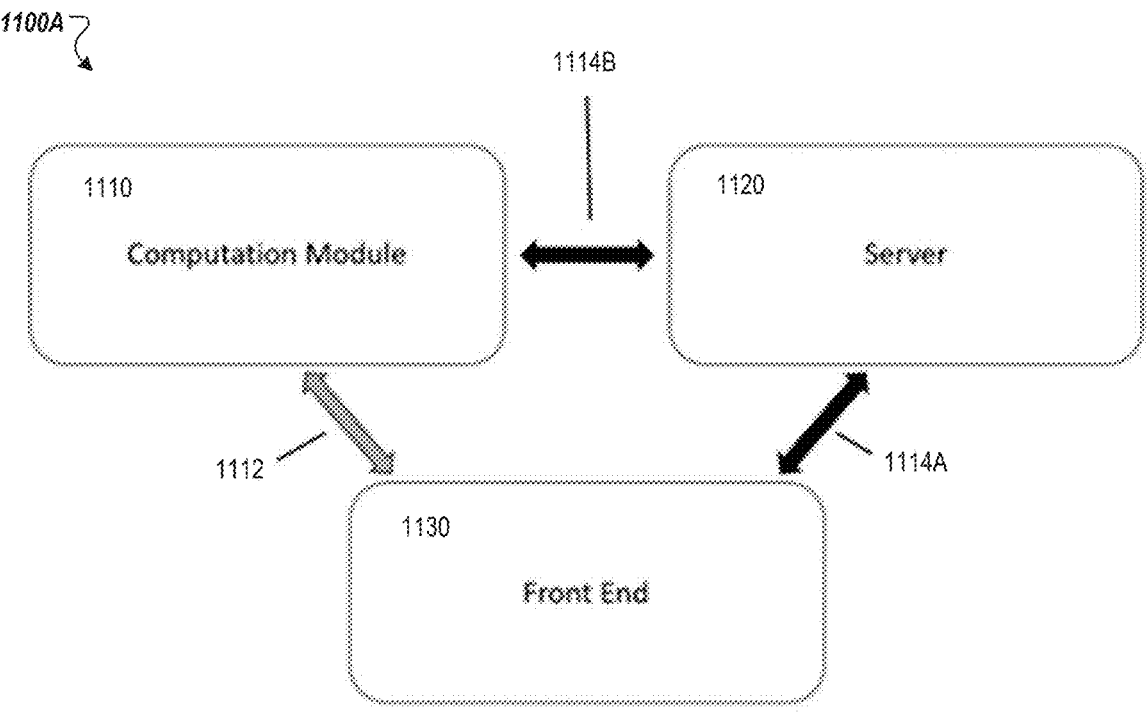
FIGS. 11A-B are flow charts of example methods associated with processing assessment data, according to certain embodiments.
Figure 11B:
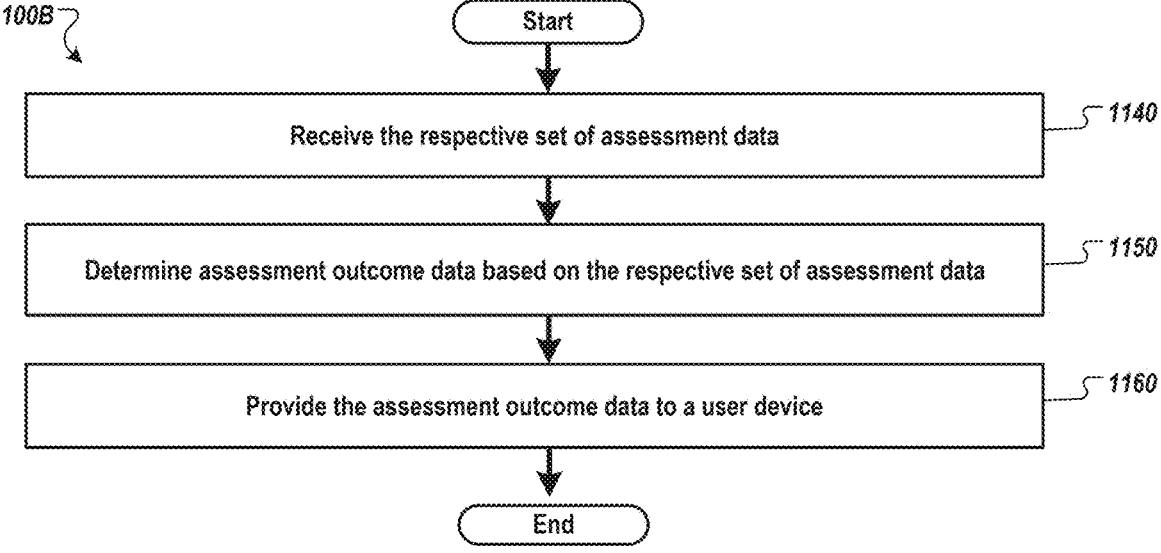

FIGS. 11A-B are flow charts of example methods asso-ciated with processing assessment data, according to certain embodiments. FIG. 11A is a flow chart of an example method 1100A illustrating the computational module 1110 (e.g., processing device, application) sending and receiving data, including commands and assessment data (e.g., exami-nation data). The computational module 1110 may send and/or receive data to and/or from a server 1120 and/or a front end (e.g., GUI, user device) 1130. In some embodi-ments, the front end 1130 sends and/or receives data (e.g., commands, examination data, etc.) either directly to the computational module 1110, as seen in data flow 1112, or through an intermediary server (e.g., the server 1120), as seen in data flows 1114A-B. The server 1120 and/or front end 1130 may store assessment data from the computational module 1110 for future evaluation.

FIG. 11B is a flow chart of an example method 1100B for processing the assessment data provided by the various assessment module devices of the neurological examination system. At block 1140, the computational module (e.g., processing device) receives the respective set of assessment data from at least one of the two or more assessment module devices. At block 1150, the computational module deter-mines assessment outcome data based on the respective set of assessment data. In some embodiments the assessment outcome data is objective data (e.g., the respective sets of assessment data with no or minimal processing) obtained from the assessment module devices (e.g., force readings in pounds per square inch (PSI) from a strength assessment module device). In other embodiments, the assessment out-come is a medical diagnosis based on the objective data. At block 1160, the computational module provides the assessment outcome data to a user device (e.g., a phone, tablet, the IO module, the application, the GUI, etc.).

FIGS. 12A-31 illustrate graphical user interfaces (GUIs), according to certain embodiments. In some embodiments, the GUI may allow for a user to interface with an application (e.g., the processing device, the computational module). The application may include software components, such as, but not limited to, front-end interfaces, such as graphical user interfaces, and back-end infrastructure, such as server-side software which facilitates the operation of the assessment module devices and/or systems. The purpose of the application is to enable its operator to control the neurological examination system, receive assessment data from it, and/or input or select data for assessment purposes. Additionally, the application allows the operator to evaluate data including, but not limited to, results, result history, trendlines, and/or graphs. Depending on the type of operator interface, available tests, available data, and educational prompts may differ.

As demonstrated in the embodiments shown in FIGS. 12A-31, the application enables the automated and/or manual operation of the neurological examination system by sending and receiving data to and/or from the computation module. The functions of the front-end application include, but are not limited to, allowing an operator to review a patient list of upcoming evaluations, enabling an operator to review previous evaluation results, provision of automated neurological evaluation tasks, and starting a manually controlled neurological evaluation.

Figure 12A:
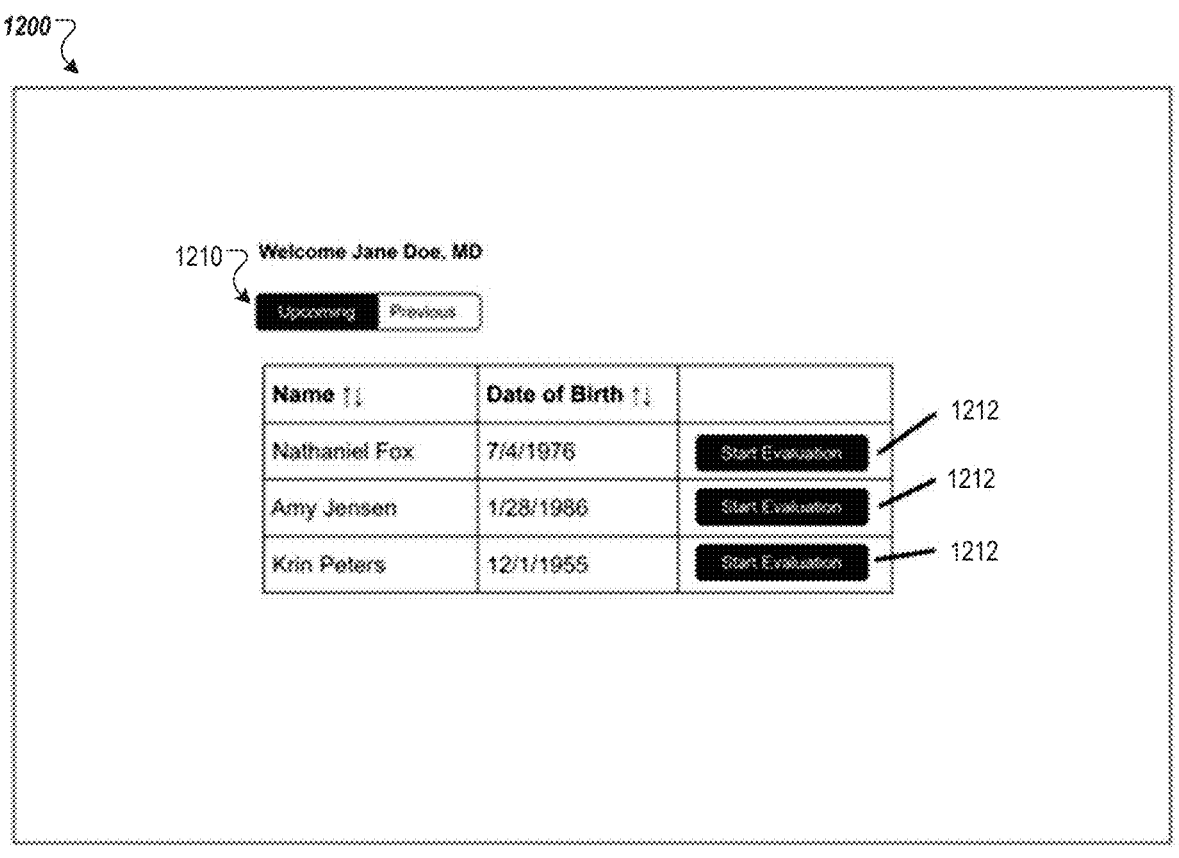
FIGS. 12A-B illustrate graphical user interfaces (GUIs) including patient lists, according to certain embodiments.
Figure 12B:
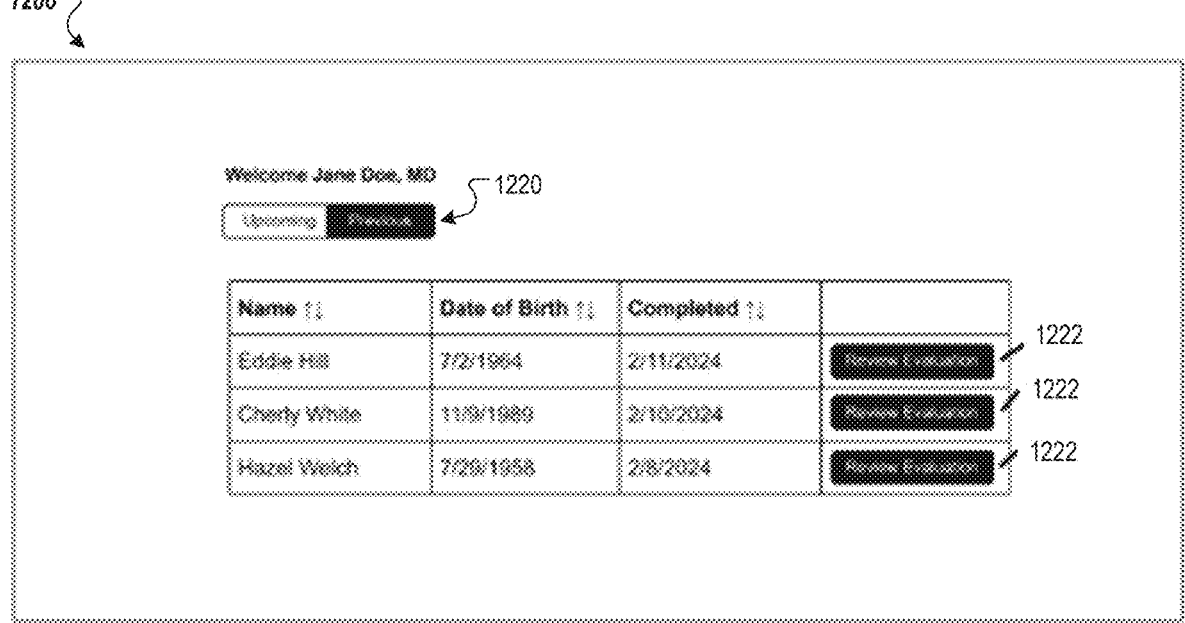

FIGS. 12A-B illustrate graphical user interfaces (GUIs), including patient lists 1200, according to certain embodiments. FIG. 12A illustrates the GUI displaying the patient list 1200 of patients in a list of upcoming evaluations 1210, according to one embodiment. FIG. 12B illustrates the GUI displaying the patient list 1200 of patients in a list of previous evaluations 1220, according to one embodiment. The GUI may include a button 1212 to start an evaluation and/or a button 1222 to review results from a previous evaluation.

Figure 13A:
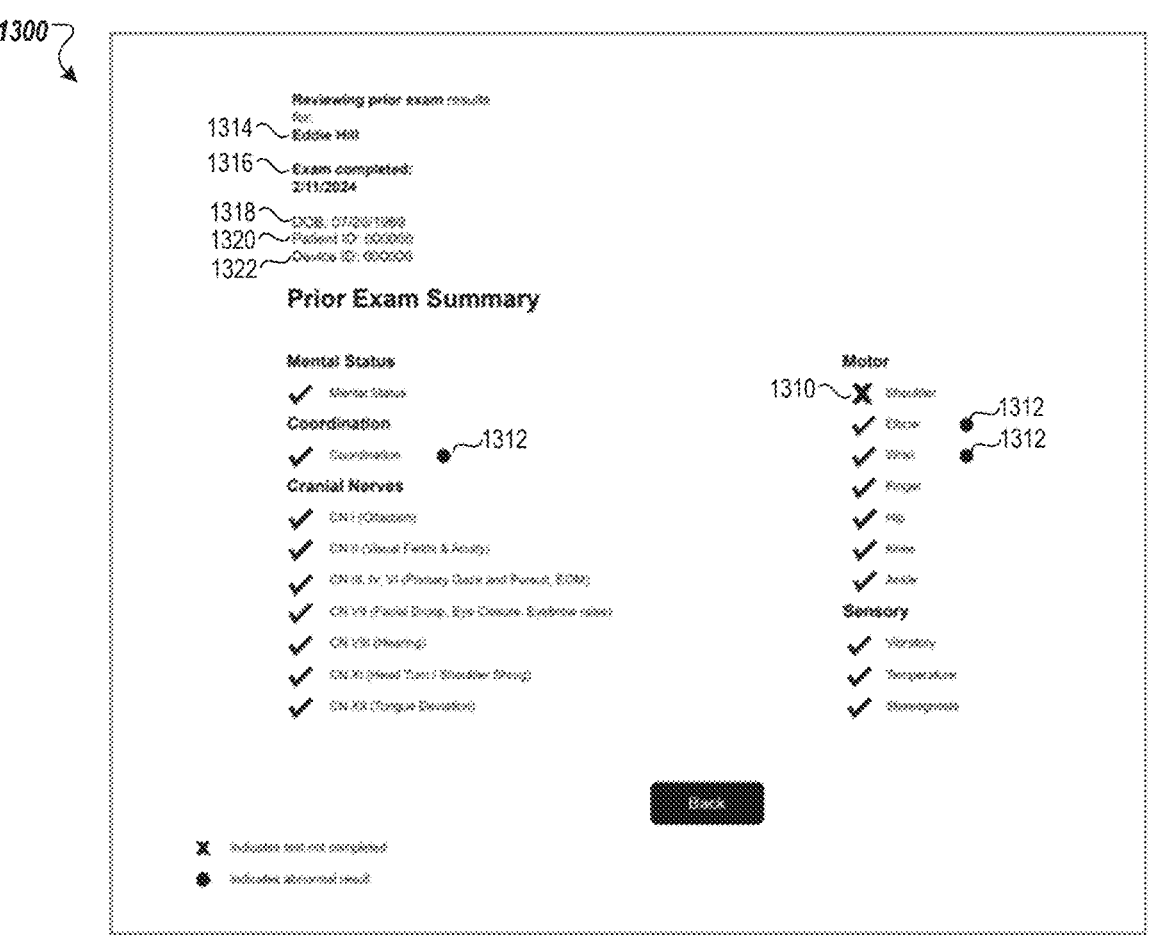
FIGS. 13A-B illustrate GUIs including prior exam summaries, according to certain embodiments.
Figure 13B:
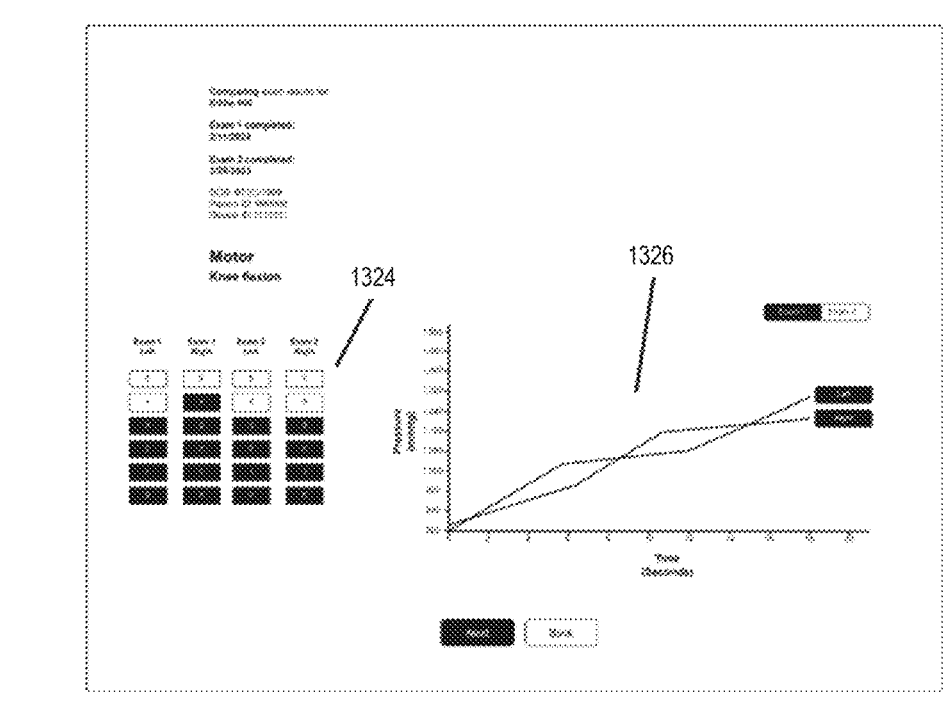

FIGS. 13A-B illustrate GUIs including prior exam summaries 1300, according to certain embodiments. The prior exam summary 1300 may allow an operator to investigate the various details of each test received from the neurological examination system. The prior exam summary 1300 may display tests that were not completed during prior examination 1310, tests that had abnormal results 1312, the patient's name 1314, the exam date 1316, the patient's date of birth 1318, the patient's identification number (e.g., ID) 1320, and the device ID 1322. In a detailed view of a prior test, there are various view options including a view displaying several prior examination results 1324 at once and/or graphs 1326 for the respective prior examination results.

Figure 14:
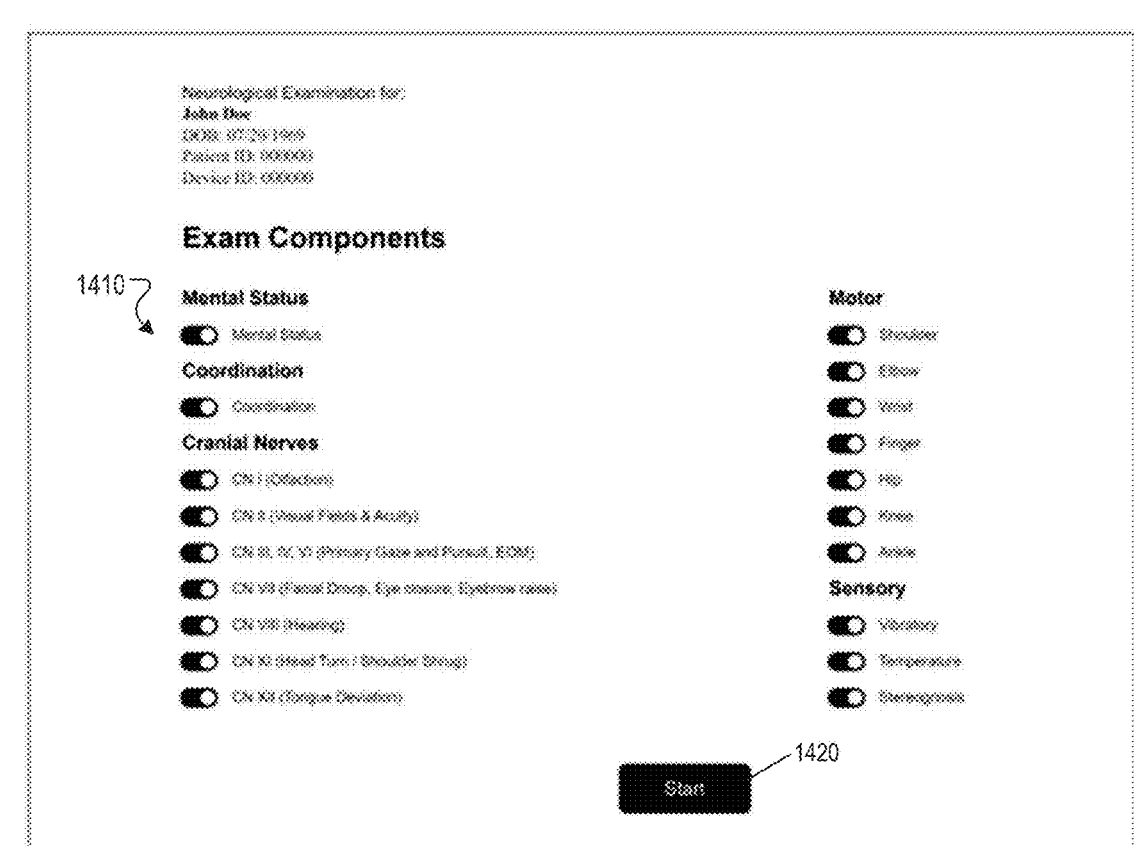
FIG. 14 illustrates a GUI including a test selection, according to certain embodiments.

FIG. 14 illustrates a GUI including a test selection 1400, according to certain embodiments. The test selection 1400 may display a variety of tests 1410 to be performed by the neurological examination system (e.g., allow the operator to choose tests that are going to be performed during an examination) and a button 1420 to start (e.g., begin) the selected test(s).

Figure 15A:
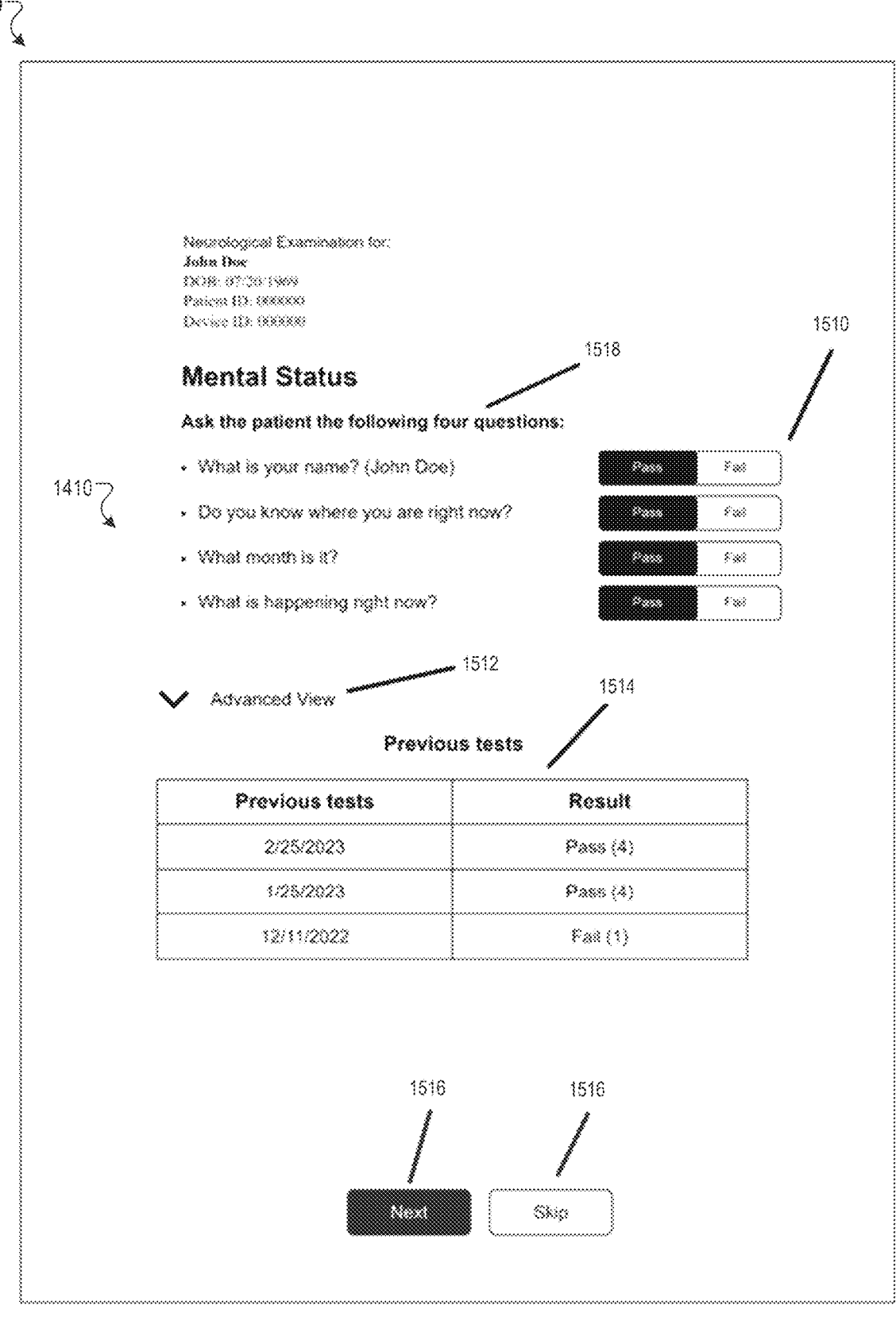
FIGS. 15A-C illustrate GUIs associated with conducting mental status examinations, according to certain embodiments.
Figure 15B:
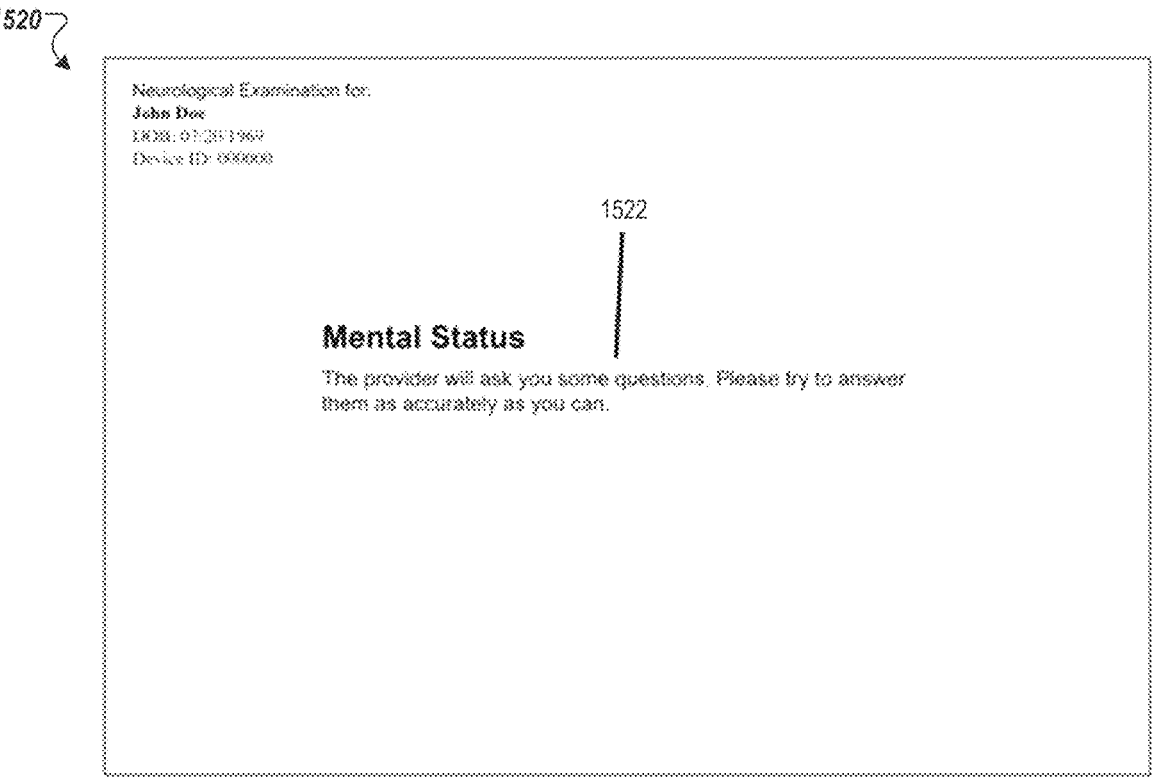
Figure 15C:
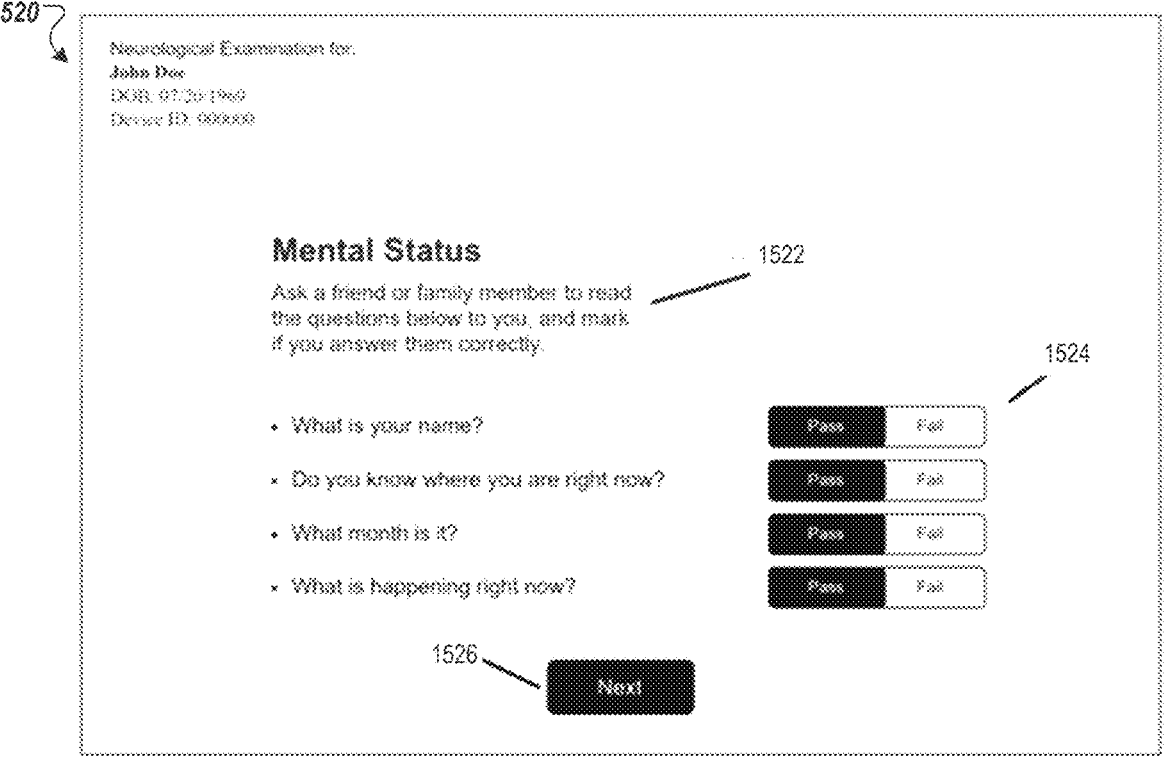

FIGS. 15A-C illustrate GUIs associated with conducting mental status examinations, according to certain embodiments. FIG. 15A shows an operator view 1500 when the mental status examination is conducted by someone other than a patient or an assistant of the patient. The operator view 1500 may include controls for each part of the test 1510, an ability to open advanced view 1512 with functions like previous test results 1514, controls to switch between tests 1516, and/or provider instructions 1518. FIG. 15B shows a patient view 1520 (e.g., displayed on the IO module) including instructions 1522 that will tell the patient what to do during the test. FIG. 15C shows the patient view 1520 when the test is conducted by the patient or the assistant of the patient, including instructions 1522, test controls 1524, and/or controls to switch to the next test 1526.

Figure 16B:
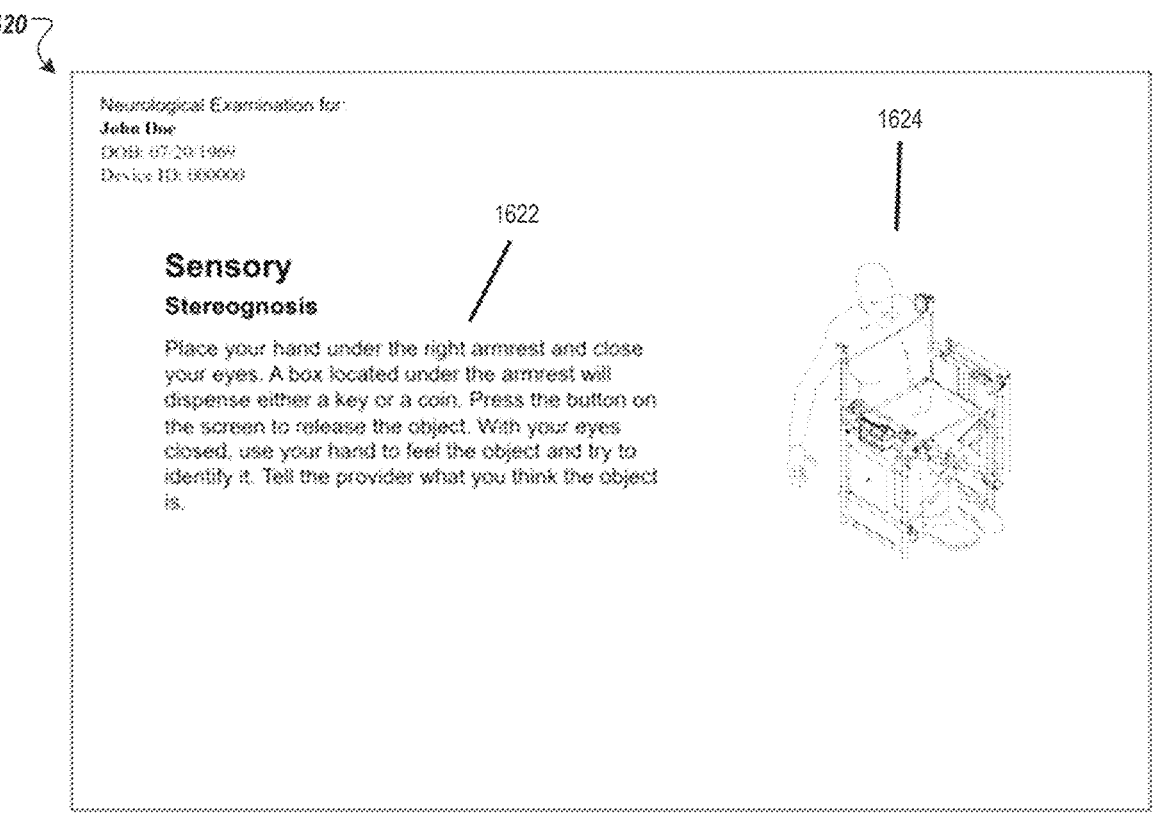
Figure 16C:
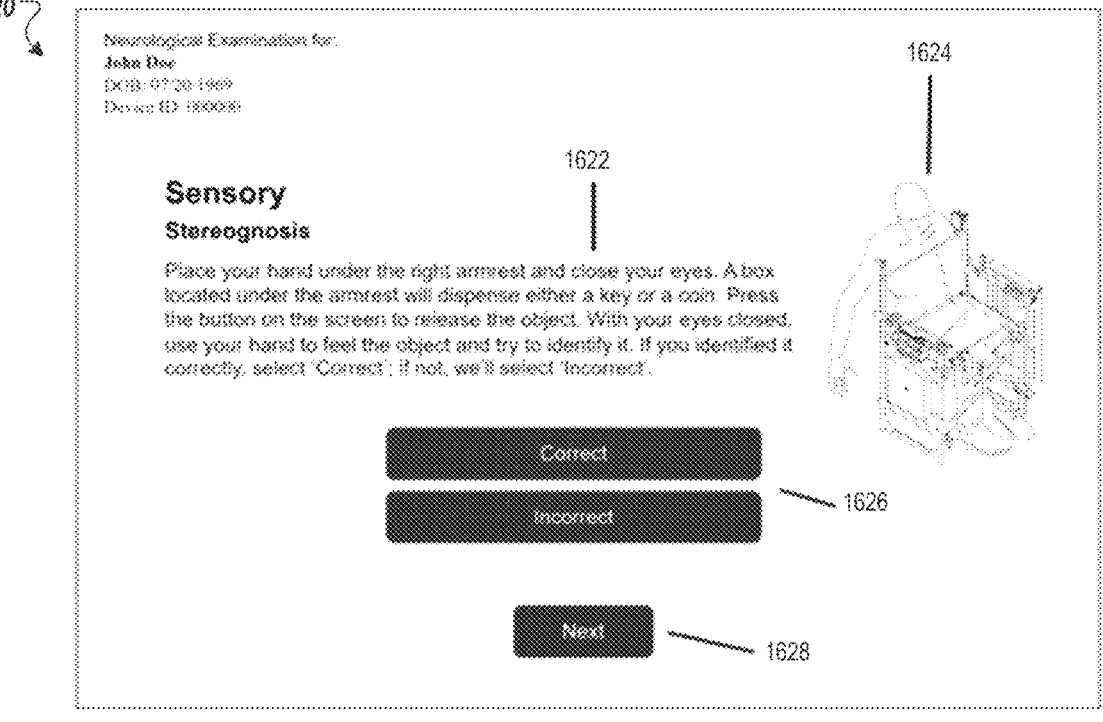

FIGS. 16A-C illustrate GUIs associated with conducting a stereognosis examination, according to certain embodiments. FIG. 16A shows an operator view 1600 when the stereognosis examination is conducted by someone other than a patient or an assistant of the patient. The operator view 1600 may include controls for each part of the test 1610, an ability to open advanced view 1612 with functions like previous test results 1614, controls to switch between tests 1616, and/or provider instructions 1618. FIG. 16B shows a patient view 1620 (e.g., displayed on the IO module) including instructions 1622 and/or visual aids 1624 (e.g., video aids, animations, still images, etc.) that will tell the patient what to do during the test. FIG. 16C shows the patient view 1620 when the test is conducted by the patient or the assistant of the patient, including instructions 1622, visual aids 1624, test controls 1626, and/or controls to switch to the next test 1628.

Figure 17B:
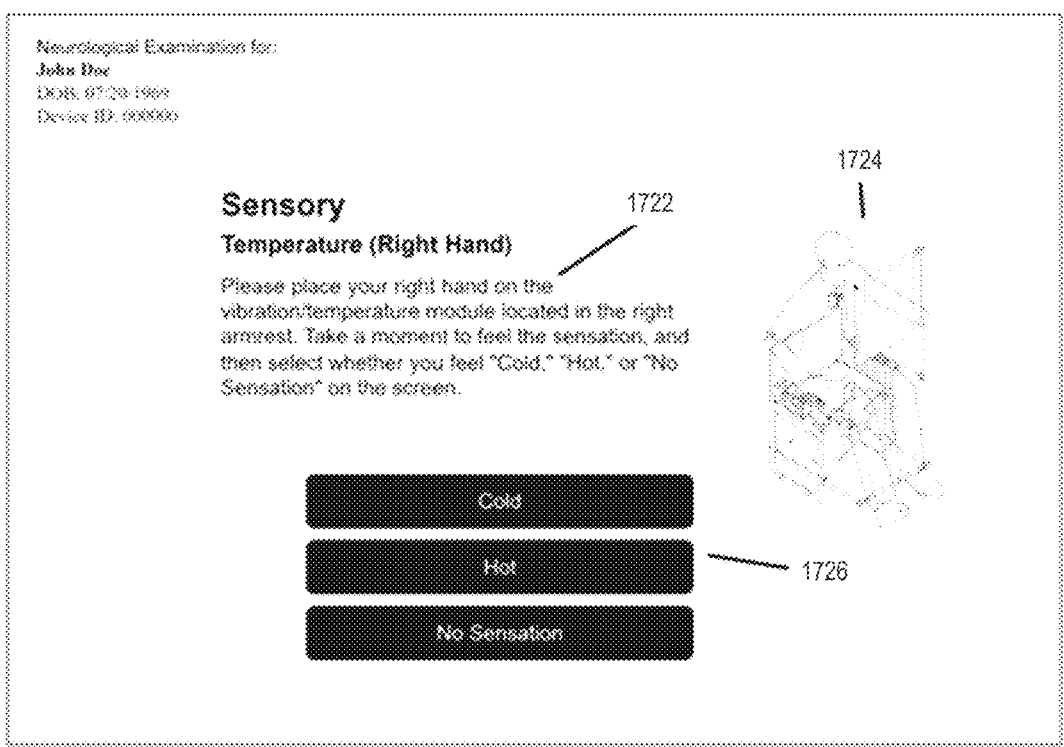
Figure 17C:
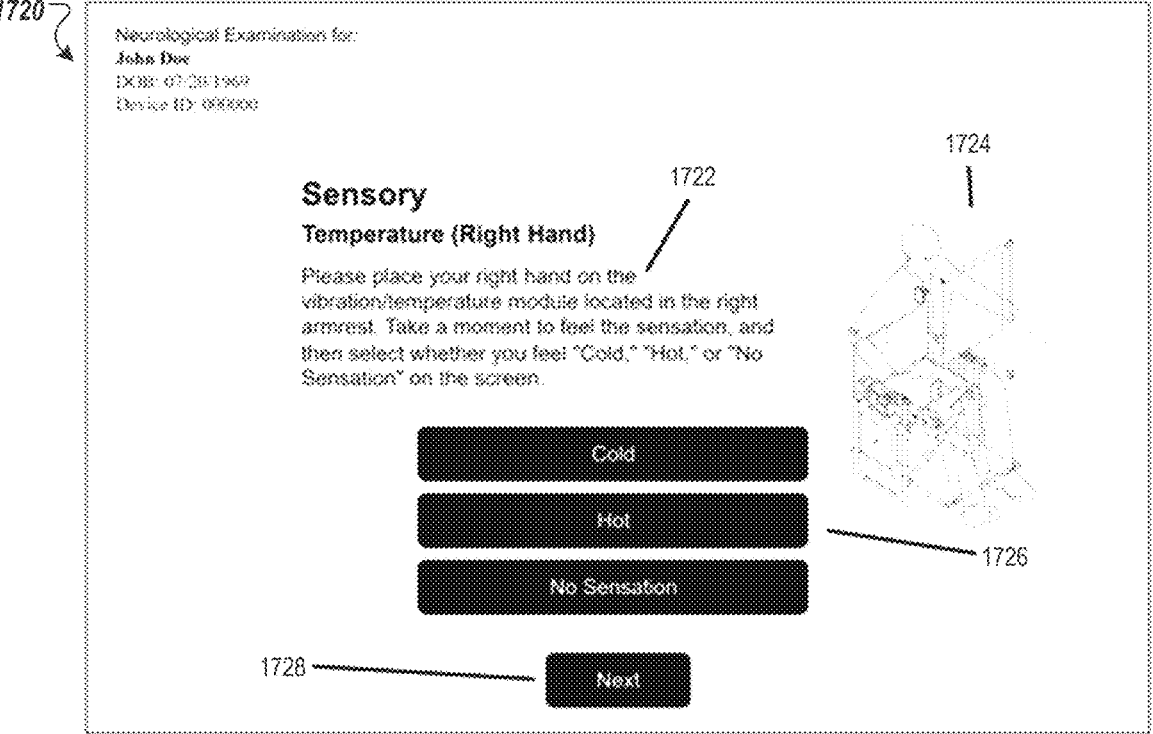

FIGS. 17A-C illustrate GUIs associated with conducting a temperature sensation portion of a sensory examination, according to certain embodiments. FIG. 17A shows an operator view 1700 when the temperature sensation portion of the sensory examination is conducted by someone other than a patient or an assistant of the patient. The operator view 1700 may include controls for each part of the test 1710, an ability to open advanced view 1712 with functions like previous test results 1714 and current temperature 1715, controls to switch between tests 1716, and/or provider instructions 1718. FIG. 17B shows a patient view 1720 (e.g., displayed on the IO module) including instructions 1722 and/or visual aids 1724 that will tell the patient what to do during the test and test controls 1726. FIG. 17C shows the patient view 1720 when the test is conducted by the patient or the assistant of the patient, including instructions 1722, visual aids 1724, test controls 1726, and/or controls to switch to the next test 1728.

FIGS. 18A-C illustrate GUIs associated with conducting a vibratory sensation portion of a sensory examination, according to certain embodiments. FIG. 18A shows an operator view 1800 when the vibratory sensation portion of the sensory examination is conducted by someone other than a patient or an assistant of the patient. The operator view 1800 may include controls for each part of the test 1810, an ability to open advanced view 1812 with functions like previous test results 1814 and current vibration strength 1815, controls to switch between tests 1816, and/or provider instructions 1818. FIG. 18B shows a patient view 1820 (e.g., displayed on the IO module) including instructions 1822 and/or visual aids 1824 that will tell the patient what to do during the test. FIG. 18C shows the patient view 1820 when the test is conducted by the patient or the assistant of the patient, including instructions 1822, visual aids 1824, and/or controls to switch to the next test 1828.

Figure 19A:
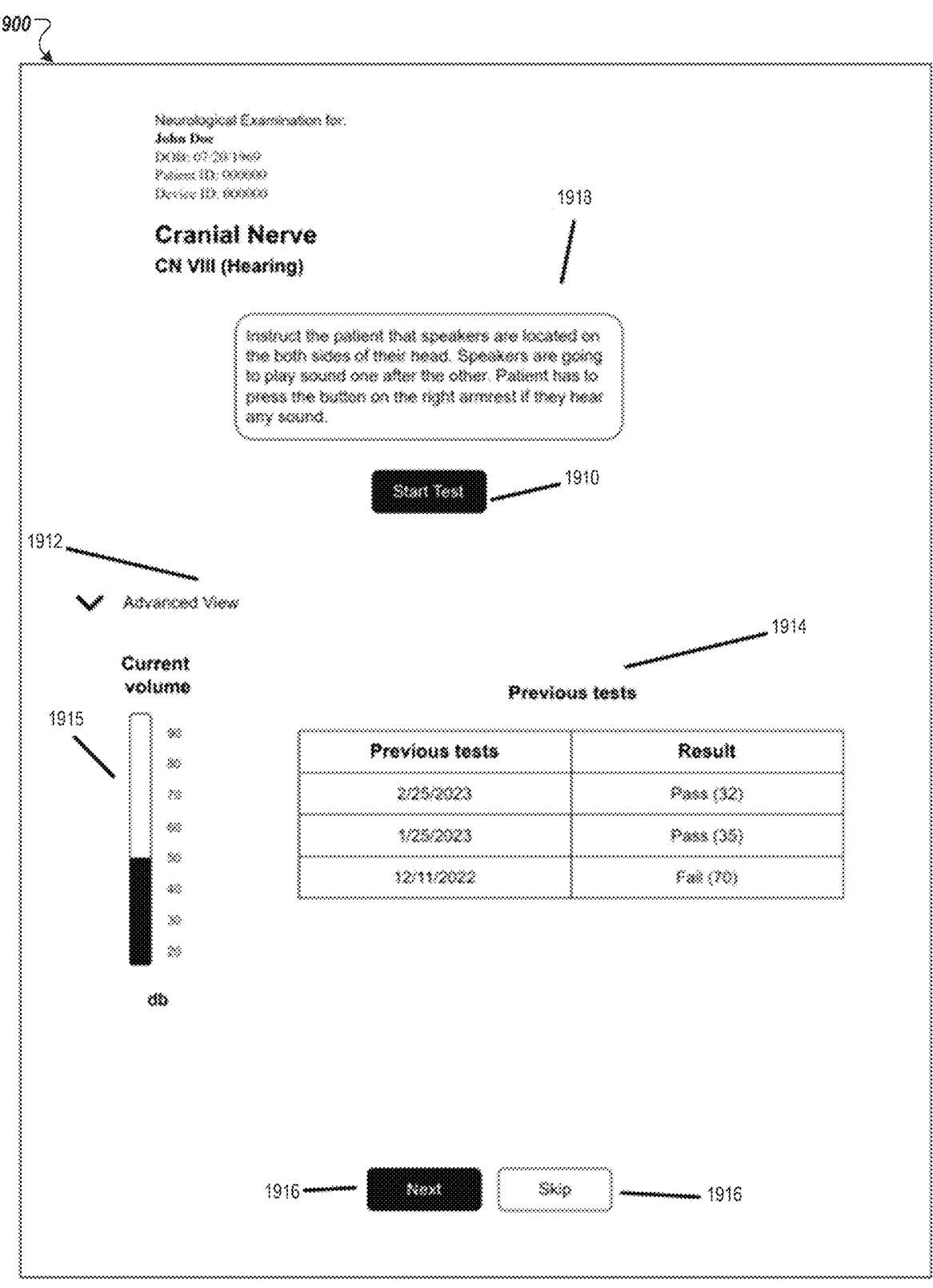
FIGS. 19A-C illustrate GUIs associated with conducting a hearing examination, according to certain embodiments.
Figure 19B:
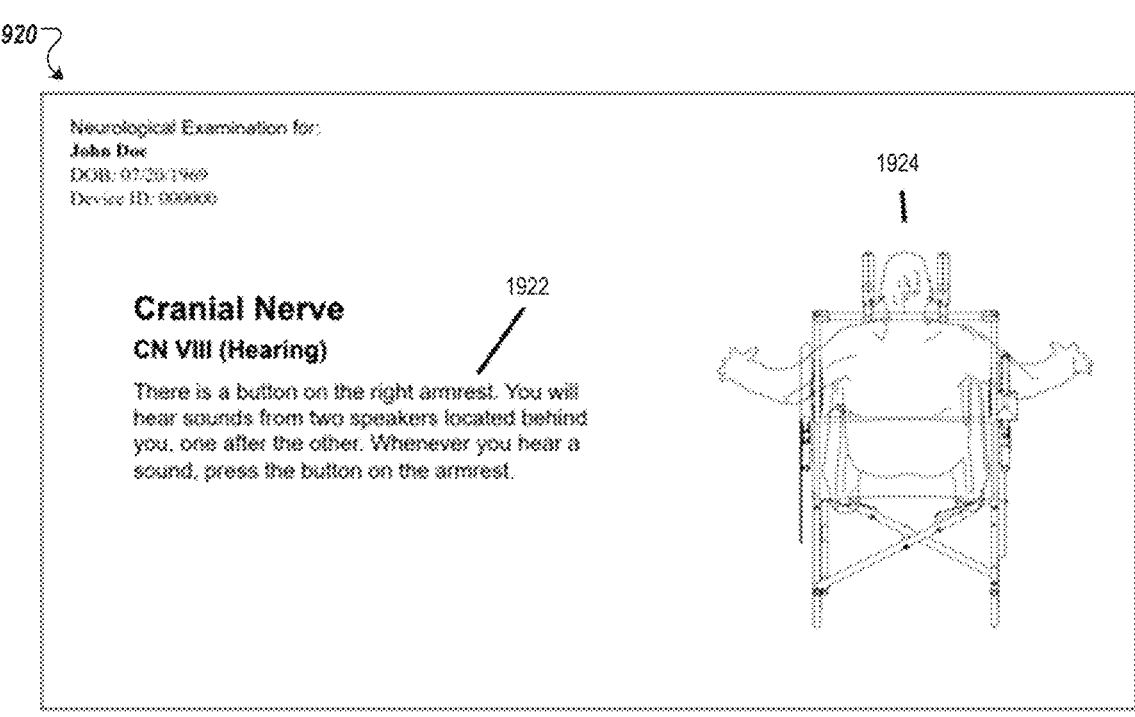
Figure 19C:
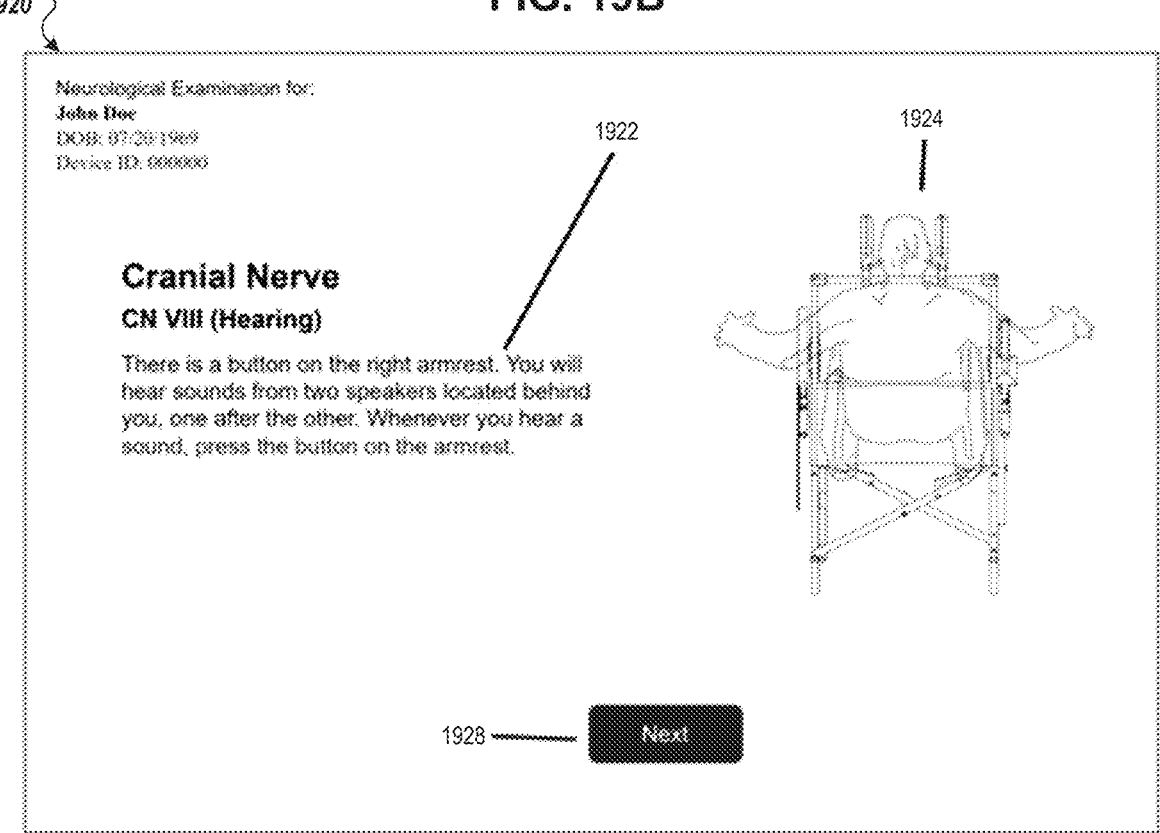

FIGS. 19A-C illustrate GUIs associated with conducting a hearing examination, according to certain embodiments. FIG. 19A shows an operator view 1900 when the hearing examination is conducted by someone other than a patient or an assistant of the patient. The operator view 1900 may include controls for each part of the test 1910, an ability to open advanced view 1912 with functions like previous test results 1914 and current volume level 1915, controls to switch between tests 1916, and/or provider instructions 1918. FIG. 19B shows a patient view 1920 (e.g., displayed on the IO module) including instructions 1922 and/or visual aids 1924 that will tell the patient what to do during the test. FIG. 19C shows the patient view 1920 when the test is conducted by the patient or the assistant of the patient, including instructions 1922, visual aids 1924, and/or controls to switch to the next test 1928.

Figure 20B:
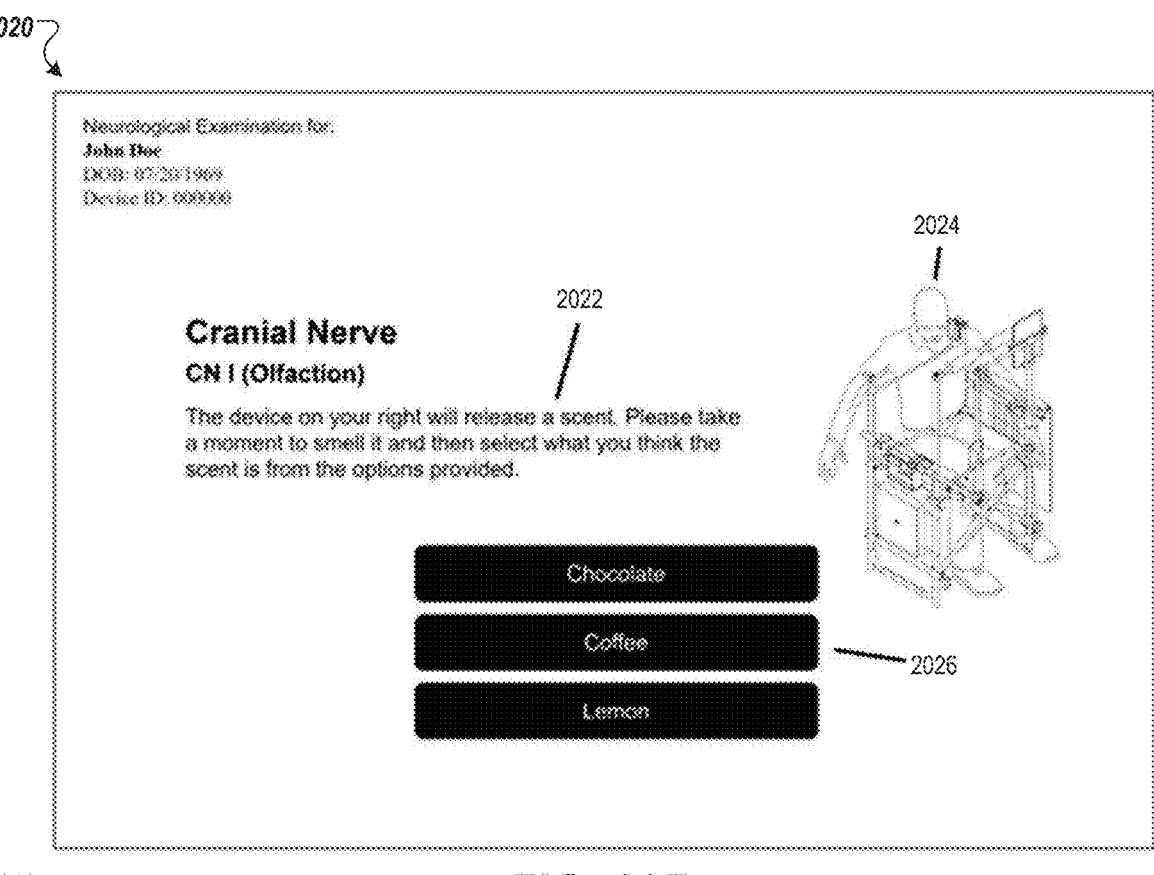
Figure 20C:
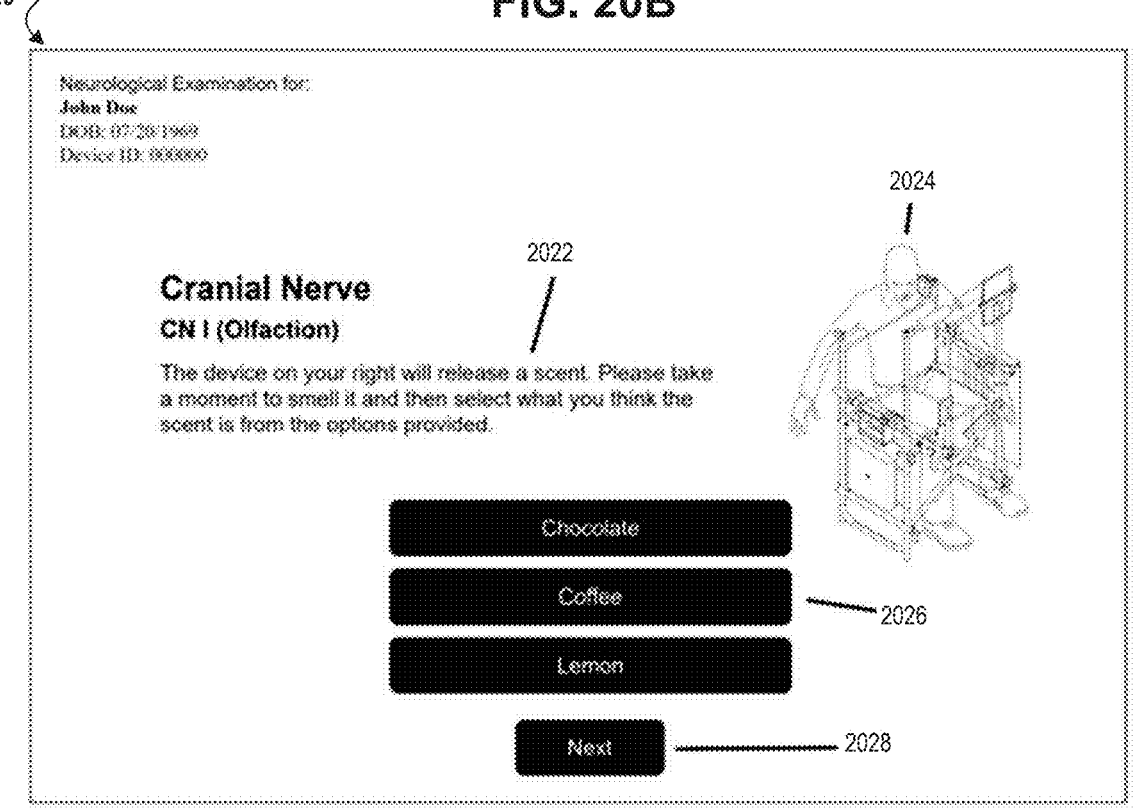

FIGS. 20A-C illustrate GUIs associated with conducting an olfaction examination, according to certain embodiments. FIG. 20A shows an operator view 2000 when the olfaction examination is conducted by someone other than a patient or an assistant of the patient. The operator view 2000 may include controls for each part of the test 2010, an ability to open advanced view 2012 with functions like previous test results 2014 and current smell being emitted 2015, controls to switch between tests 2016, and/or provider instructions 2018. FIG. 20B shows a patient view 2020 (e.g., displayed on the IO module) including instructions 2022 and/or visual aids 2024 that will tell the patient what to do during the test and test controls 2026. FIG. 20C shows the patient view 2020 when the test is conducted by the patient or the assistant of the patient, including instructions 2022, visual aids 2024, test controls 2026, and/or controls to switch to the next test 2028.

Figure 21B:
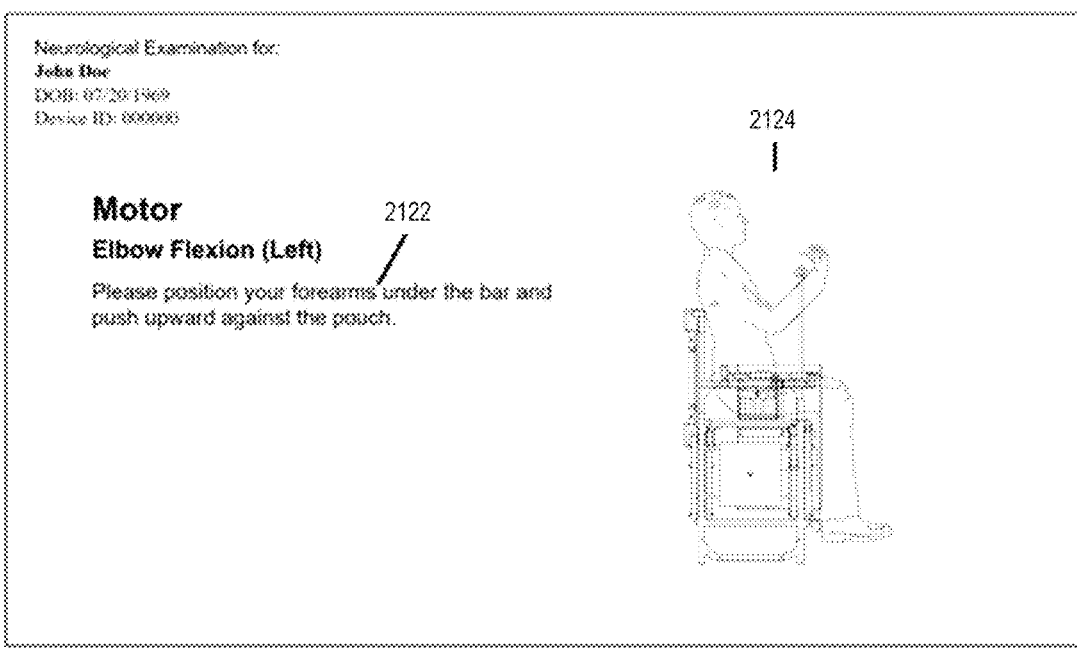
Figure 21C:
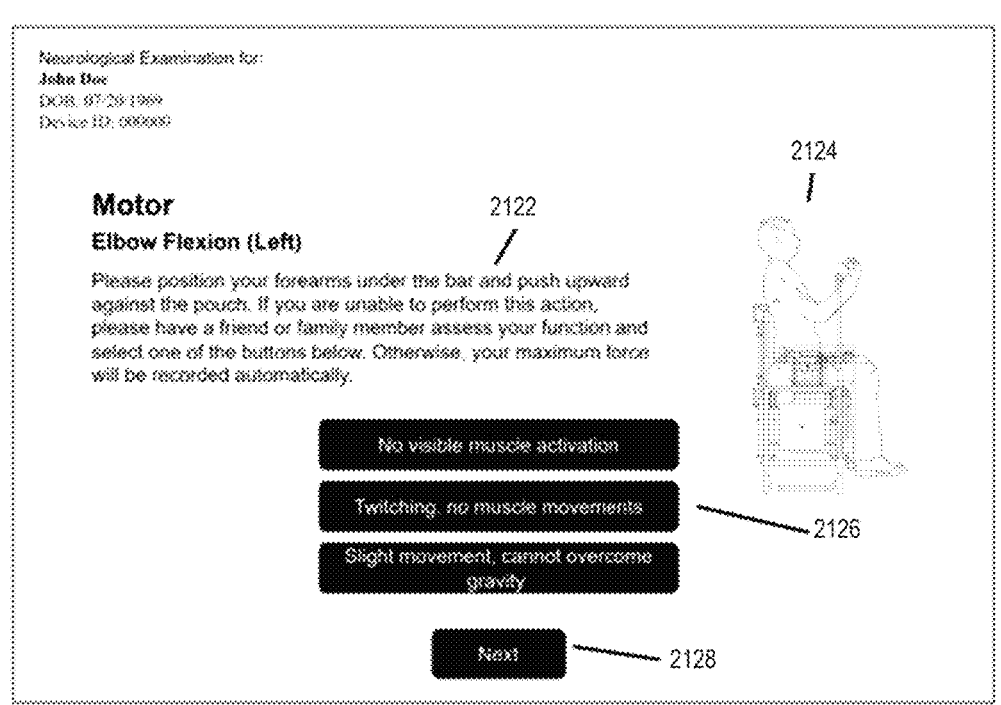

FIGS. 21A-C illustrate GUIs associated with conducting a strength examination, according to certain embodiments. FIG. 21A shows an operator view 2100 when the strength examination is conducted by someone other than a patient or an assistant of the patient. The operator view 2100 may include controls for each part of the test 2110, an ability to open advanced view 2112 with functions like previous test results 2114 and current pressure graph 2115, controls to switch between tests 2116, current strength on a scale 2117, and/or provider instructions 2118. FIG. 21B shows a patient view 2120 (e.g., displayed on the IO module) including instructions 2122 and/or visual aids 2124 that will tell the patient what to do during the test. FIG. 21C shows the patient view 2120 when the test is conducted by the patient or the assistant of the patient, including instructions 2122, visual aids 2124, test controls 2126, and/or controls to switch to the next test 2128.

Figure 22A:
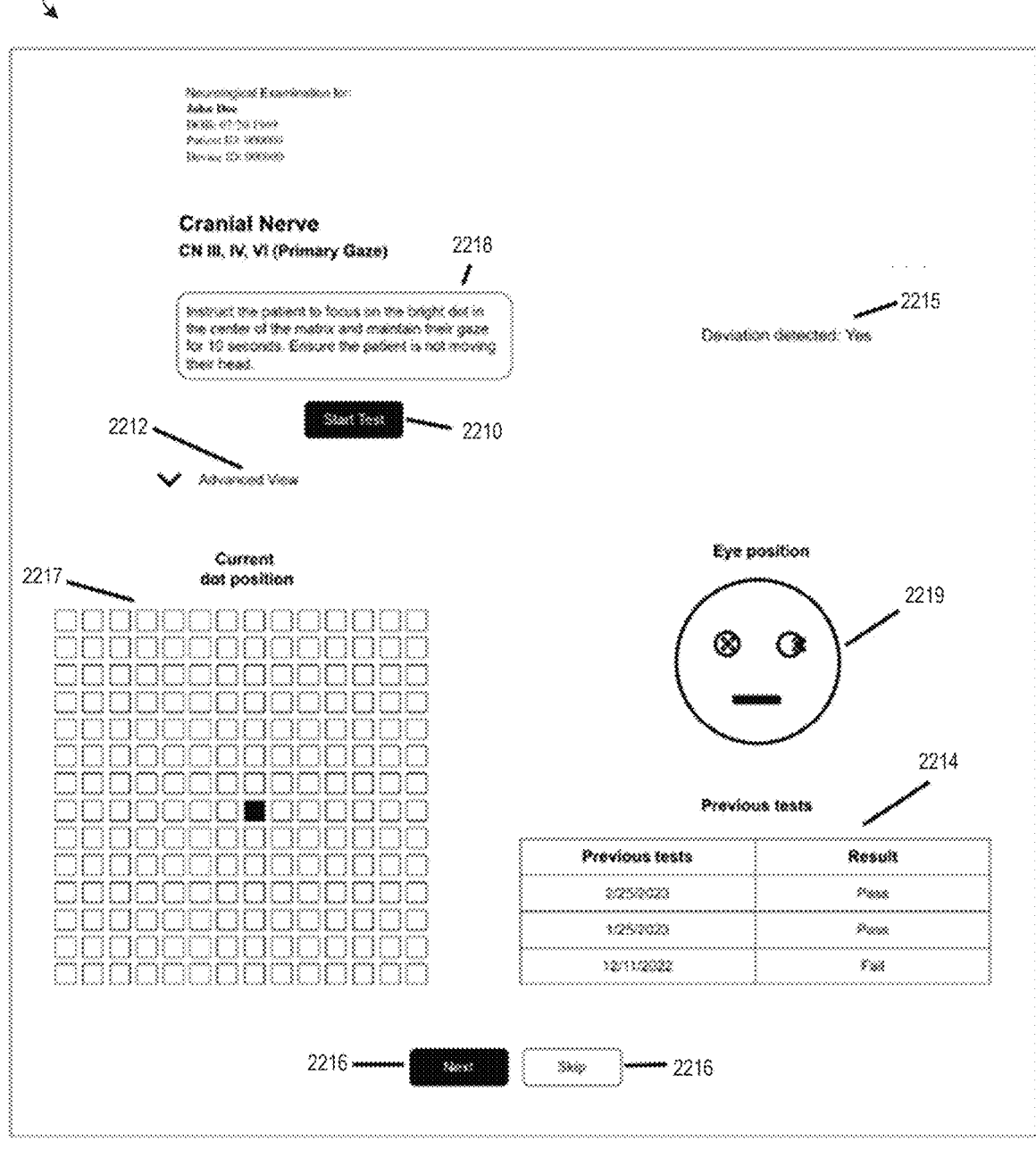
FIGS. 22A-C illustrate GUIs associated with conducting a primary gaze examination, according to certain embodiments.
Figure 22B:
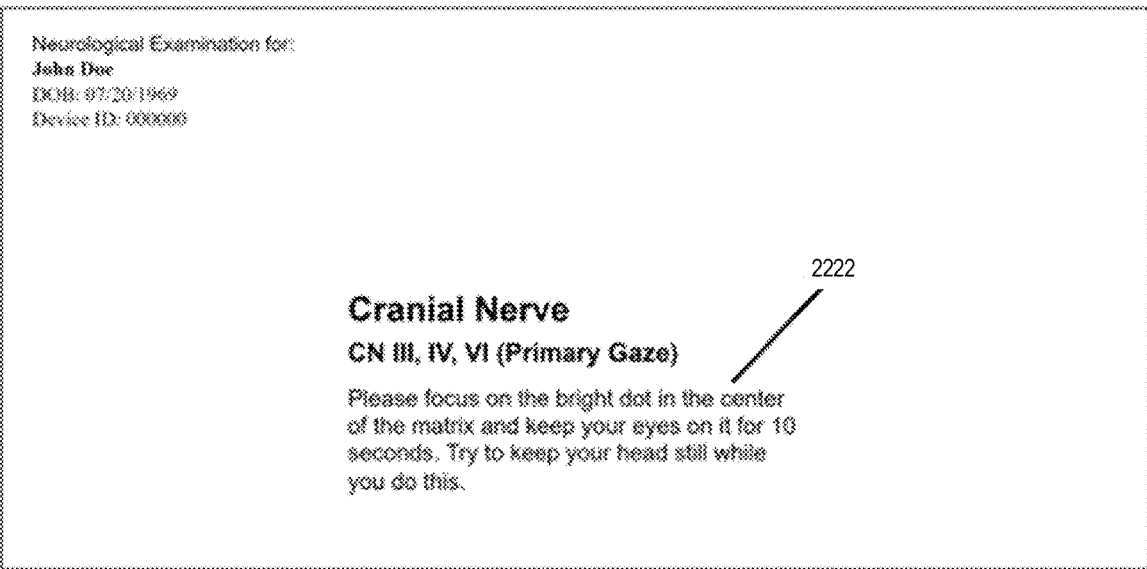
Figure 22C:
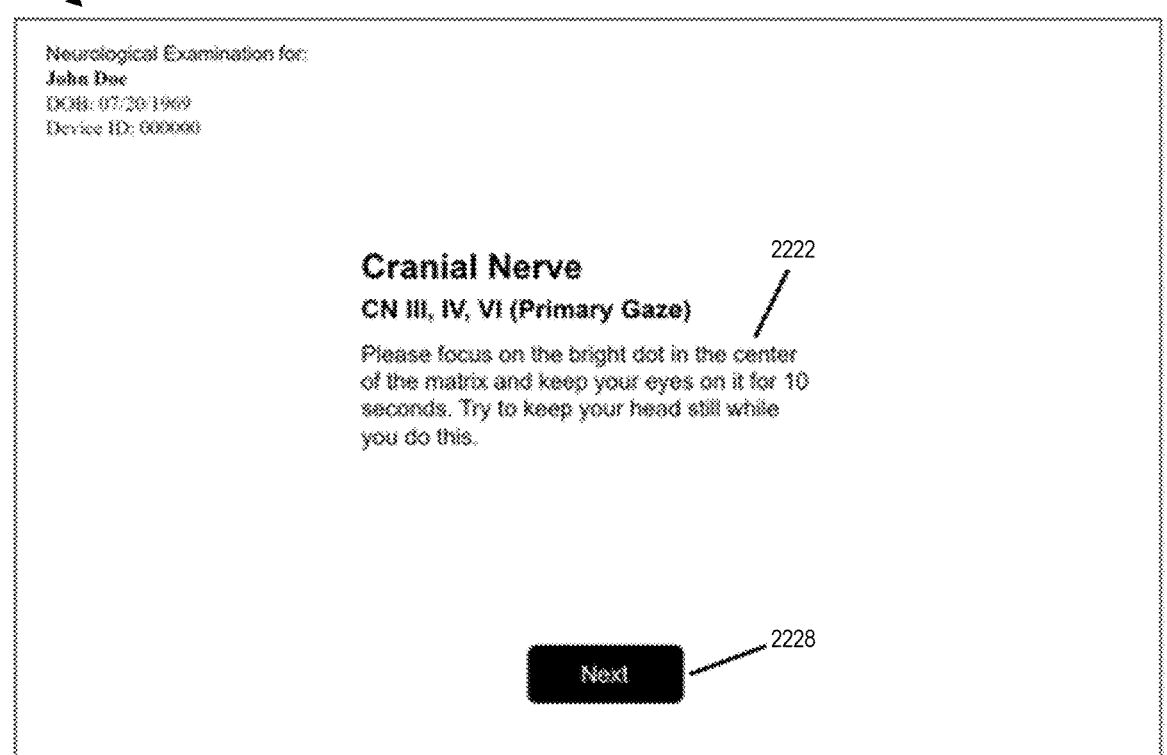

FIGS. 22A-C illustrate GUIs associated with conducting a primary gaze examination, according to certain embodiments. FIG. 22A shows an operator view 2200 when the primary gaze examination is conducted by someone other than a patient or an assistant of the patient. The operator view 2200 may include controls for each part of the test 2210, an ability to open advanced view 2212 with functions like previous test results 2214, deviation detection status 2215, controls to switch between tests 2216, current dot position 2217, provider instructions 2218, and/or patient's eye position 2219. FIG. 22B shows a patient view 2220 (e.g., displayed on the IO module) including instructions 2222 that will tell the patient what to do during the test. FIG. 22C shows the patient view 2220 when the test is conducted by the patient or the assistant of the patient, including instructions 2222 and/or controls to switch to the next test 2228.

Figure 23A:
FIGS. 23A-C illustrate GUIs associated with conducting an ocular pursuit examination, according to certain embodiments.
Figure 23B:
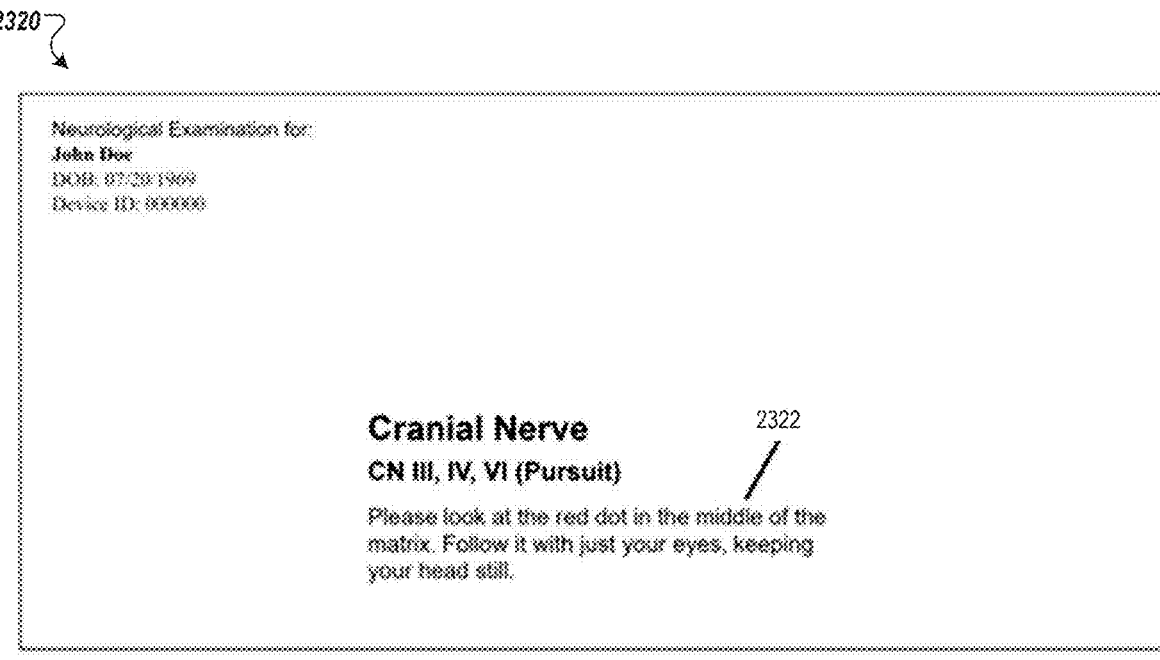
Figure 23C:
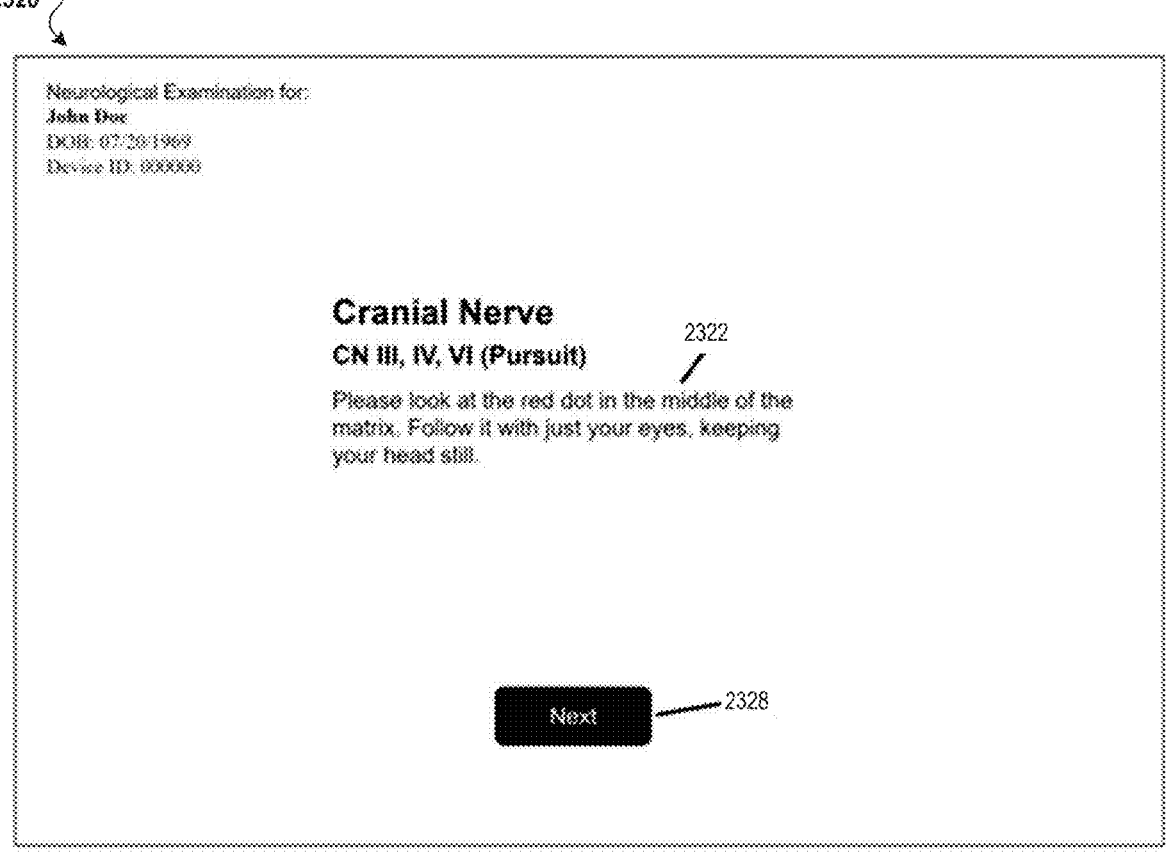

FIGS. 23A-C illustrate GUIs associated with conducting an ocular pursuit examination, according to certain embodiments. FIG. 23A shows an operator view 2300 when the ocular pursuit examination is conducted by someone other than a patient or an assistant of the patient. The operator view 2300 may include controls for each part of the test 2310, saccadic intrusions detection status 2311, an ability to open advanced view 2312 with functions like previous test results 2314 and delay 2315, controls to switch between tests 2316, current dot position 2317, provider instructions 2318, and/or patient's eye position 2319. FIG. 23B shows a patient view 2320 (e.g., displayed on the IO module) including instructions 2322 that will tell the patient what to do during the test. FIG. 23C shows the patient view 2320 when the test is conducted by the patient or the assistant of the patient, including instructions 2322 and/or controls to switch to the next test 2328.

Figure 24A:
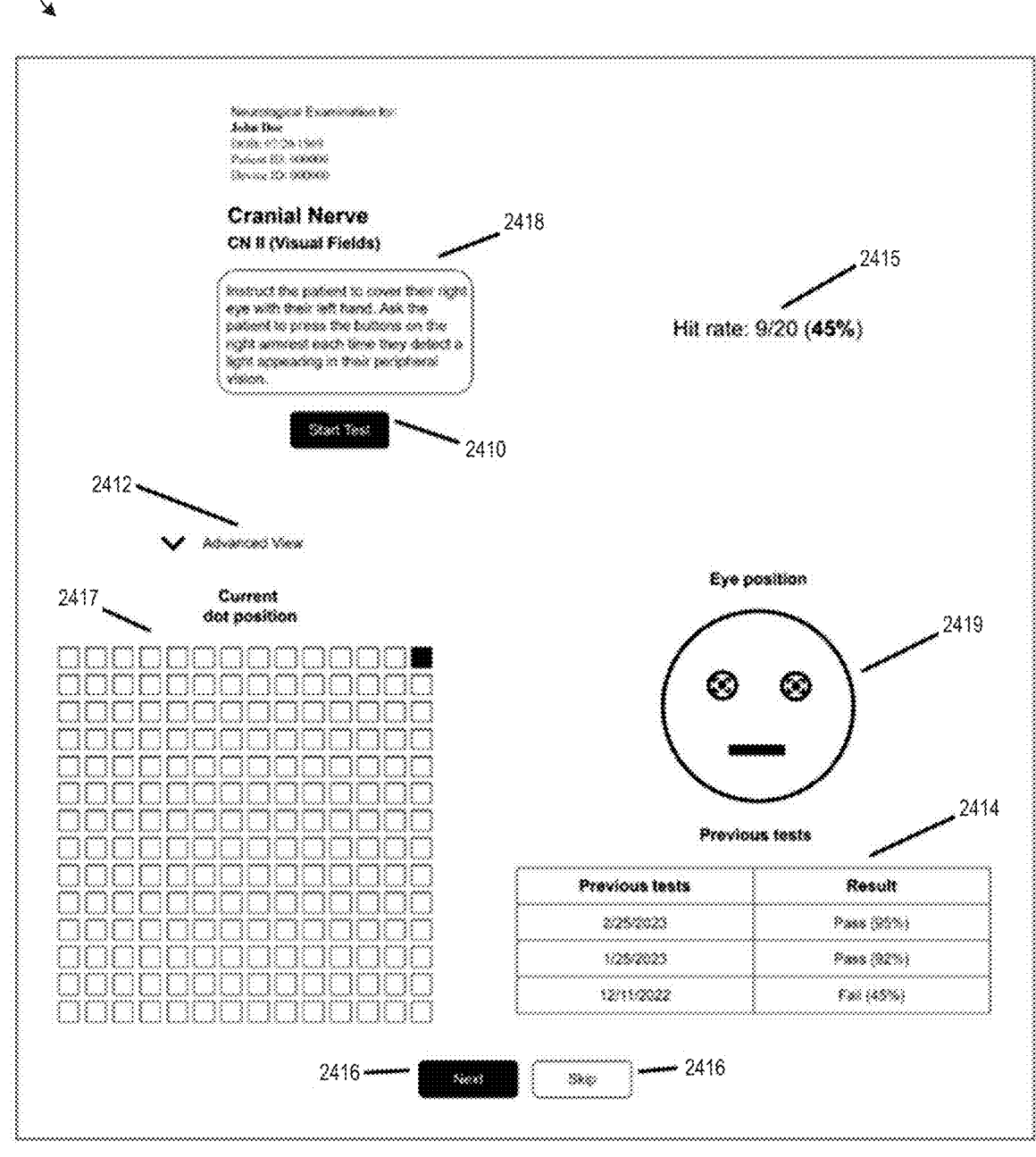
FIGS. 24A-C illustrate GUIs associated with conducting a visual fields examination, according to certain embodiments.
Figures 24B, 24C:
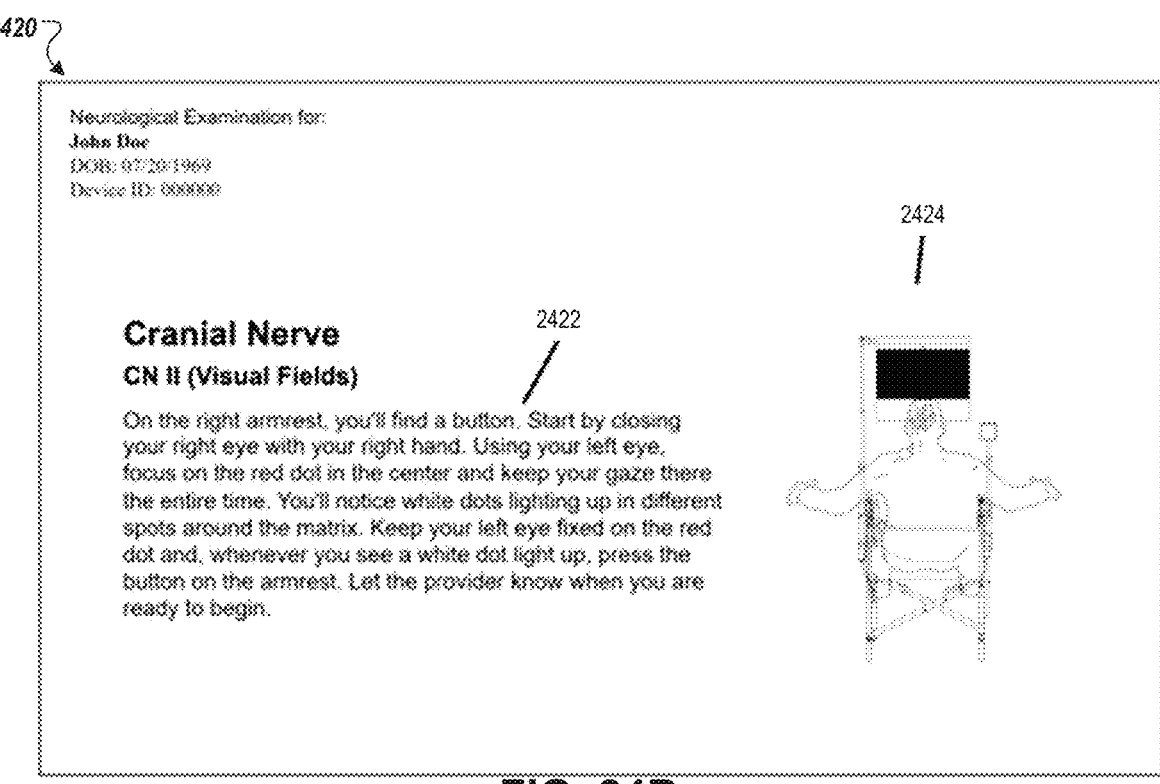

FIGS. 24A-C illustrate GUIs associated with conducting a visual fields examination, according to certain embodiments. FIG. 24A shows an operator view 2400 when the visual fields examination is conducted by someone other than a patient or an assistant of the patient. The operator view 2400 may include controls for each part of the test 2410, an ability to open advanced view 2412 with functions like previous test results 2414, hit rate 2415, controls to switch between tests 2416, current dot position 2417, provider instructions 2418, and/or patient's eye position 2419. FIG. 24B shows a patient view 2420 (e.g., displayed on the IO module) including instructions 2422 and/or visual aids 2424 that will tell the patient what to do during the test. FIG. 24C shows the patient view 2420 when the test is conducted by the patient or the assistant of the patient, including instructions 2422, visual aids 2424, and/or controls to switch to the next test 2428.

Figure 25A:
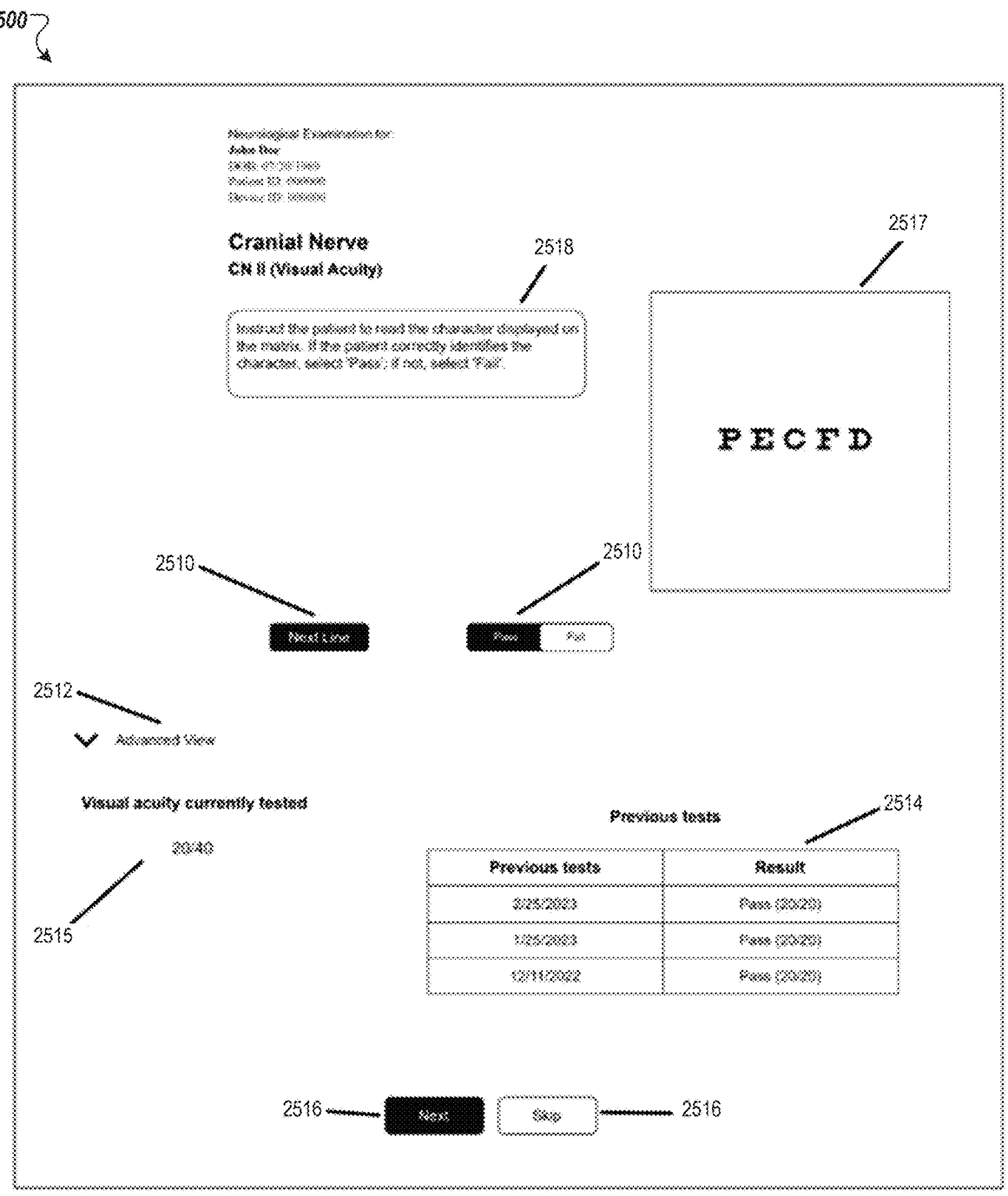
FIGS. 25A-C illustrate GUIs associated with conducting a visual acuity examination, according to certain embodiments.
Figure 25B:
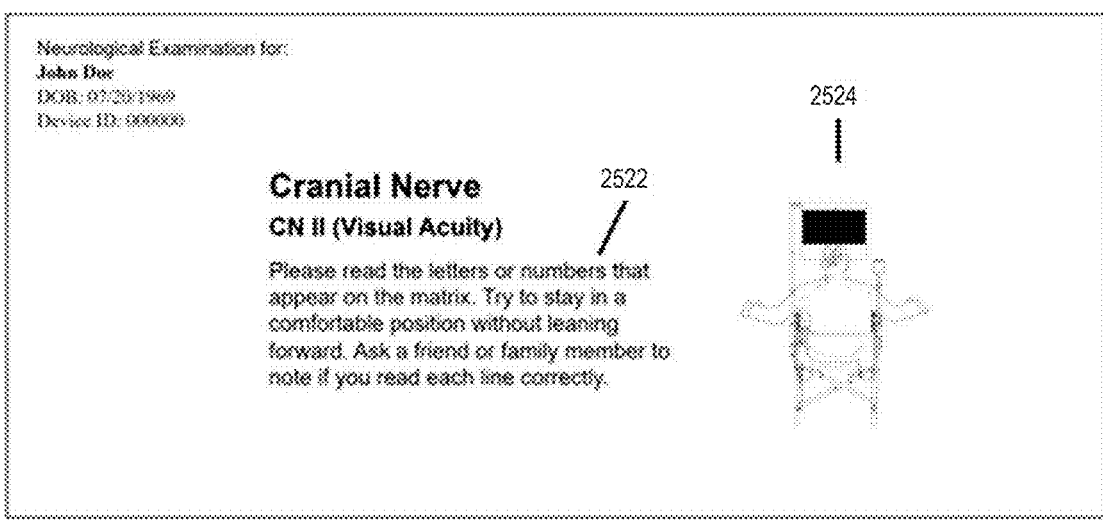
Figure 25C:
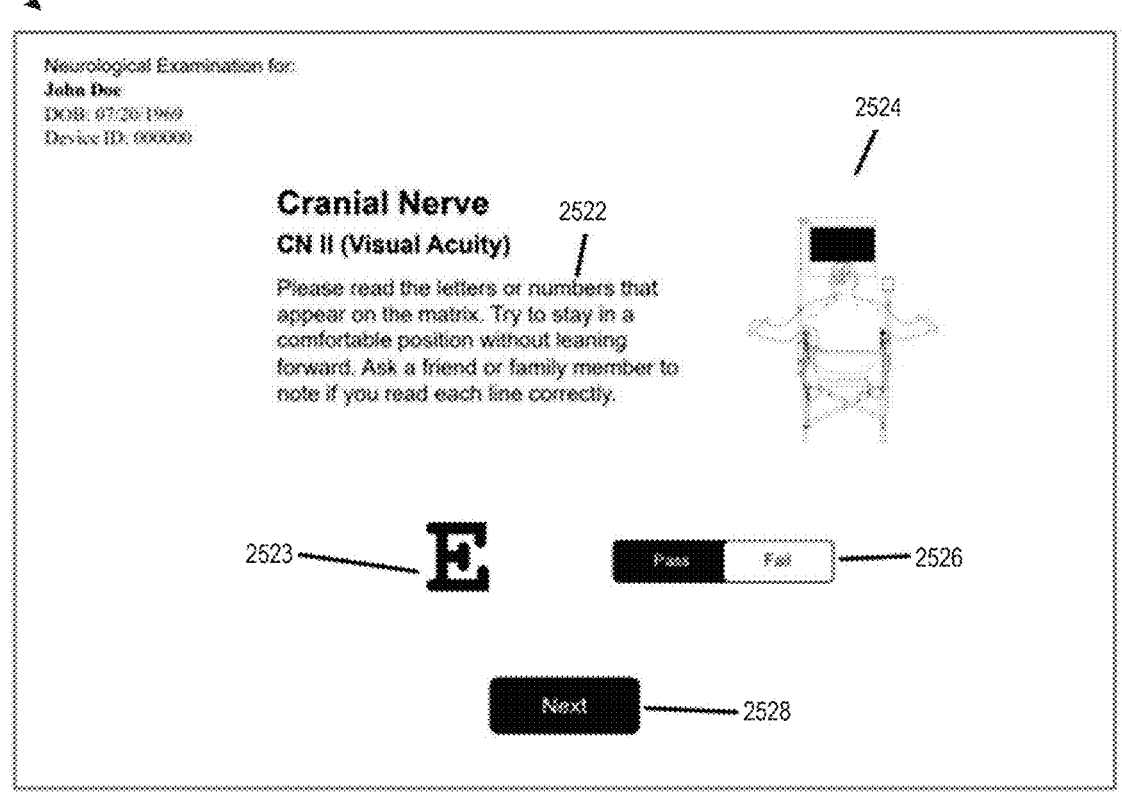

FIGS. 25A-C illustrate GUIs associated with conducting a visual acuity examination, according to certain embodiments. FIG. 25A shows an operator view 2500 when the visual acuity examination is conducted by someone other than a patient or an assistant of the patient. The operator view 2500 may include controls for each part of the test 2510, an ability to open advanced view 2512 with functions like previous test results 2514 and visual acuity currently tested 2515, controls to switch between tests 2516, current line displayed 2517, and/or provider instructions 2518. FIG. 25B shows a patient view 2520 (e.g., displayed on the IO module) including instructions 2522 and/or visual aids 2524 that will tell the patient what to do during the test. FIG. 25C shows the patient view 2520 when the test is conducted by the patient or the assistant of the patient, including instructions 2522, helper aids 2523, visual aids 2524, test controls 2526, and/or controls to switch to the next test 2528.

Figure 26A:
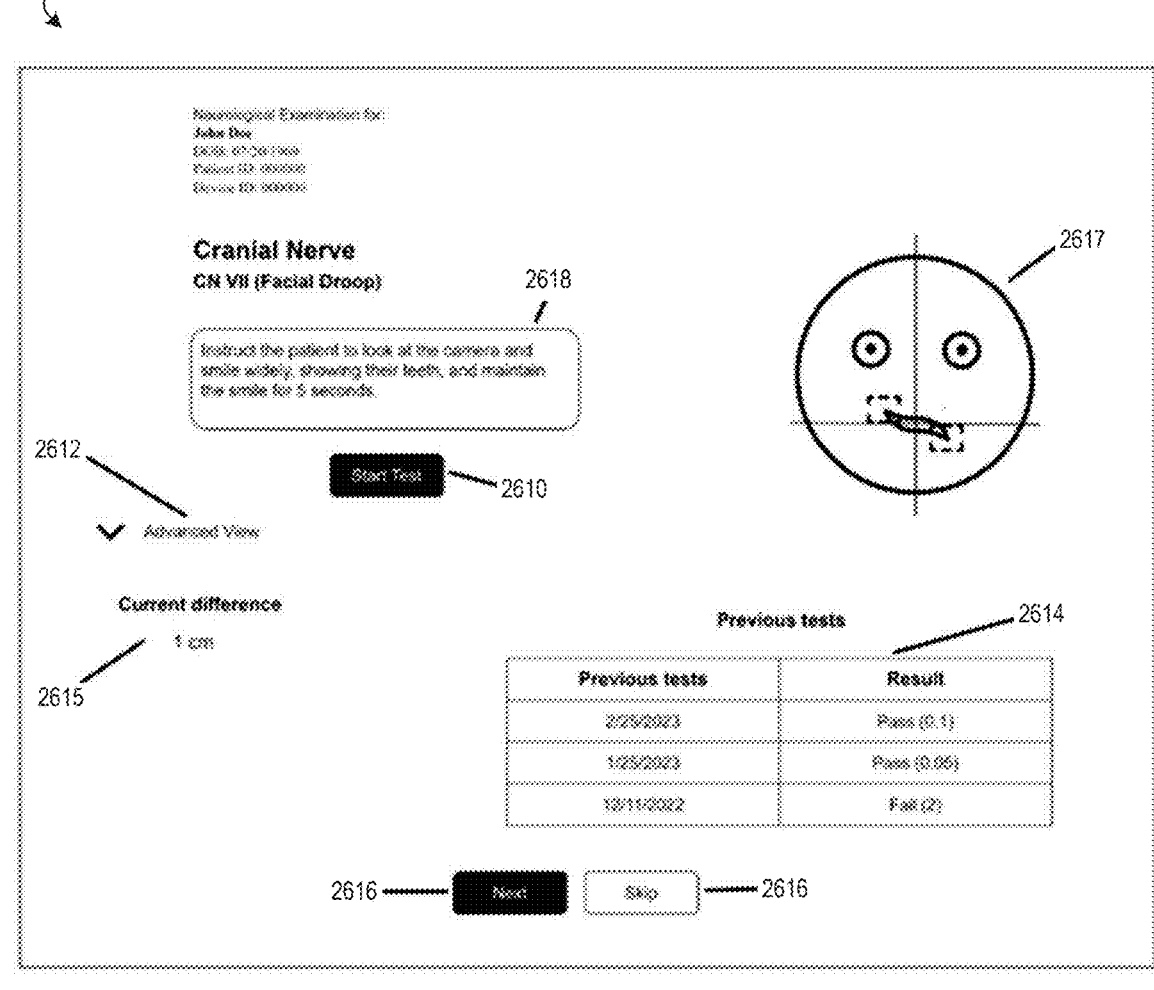

FIGS. 26A-C illustrate GUIs associated with conducting a facial droop examination, according to certain embodiments. FIG. 26A shows an operator view 2600 when the facial droop examination is conducted by someone other than a patient or an assistant of the patient. The operator view 2600 may include controls for each part of the test 2610, an ability to open advanced view 2612 with functions like previous test results 2614 and current height difference between corners of the mouth 2615, controls to switch between tests 2616, view of a patient's face with highlighted corners of a mouth 2617, and/or provider instructions 2618. FIG. 26B shows a patient view 2620 (e.g., displayed on the IO module) including instructions 2622 that will tell the patient what to do during the test. FIG. 26C shows the patient view 2620 when the test is conducted by the patient or the assistant of the patient, including instructions 2622 and/or controls to switch to the next test 2628.

Figure 27A:
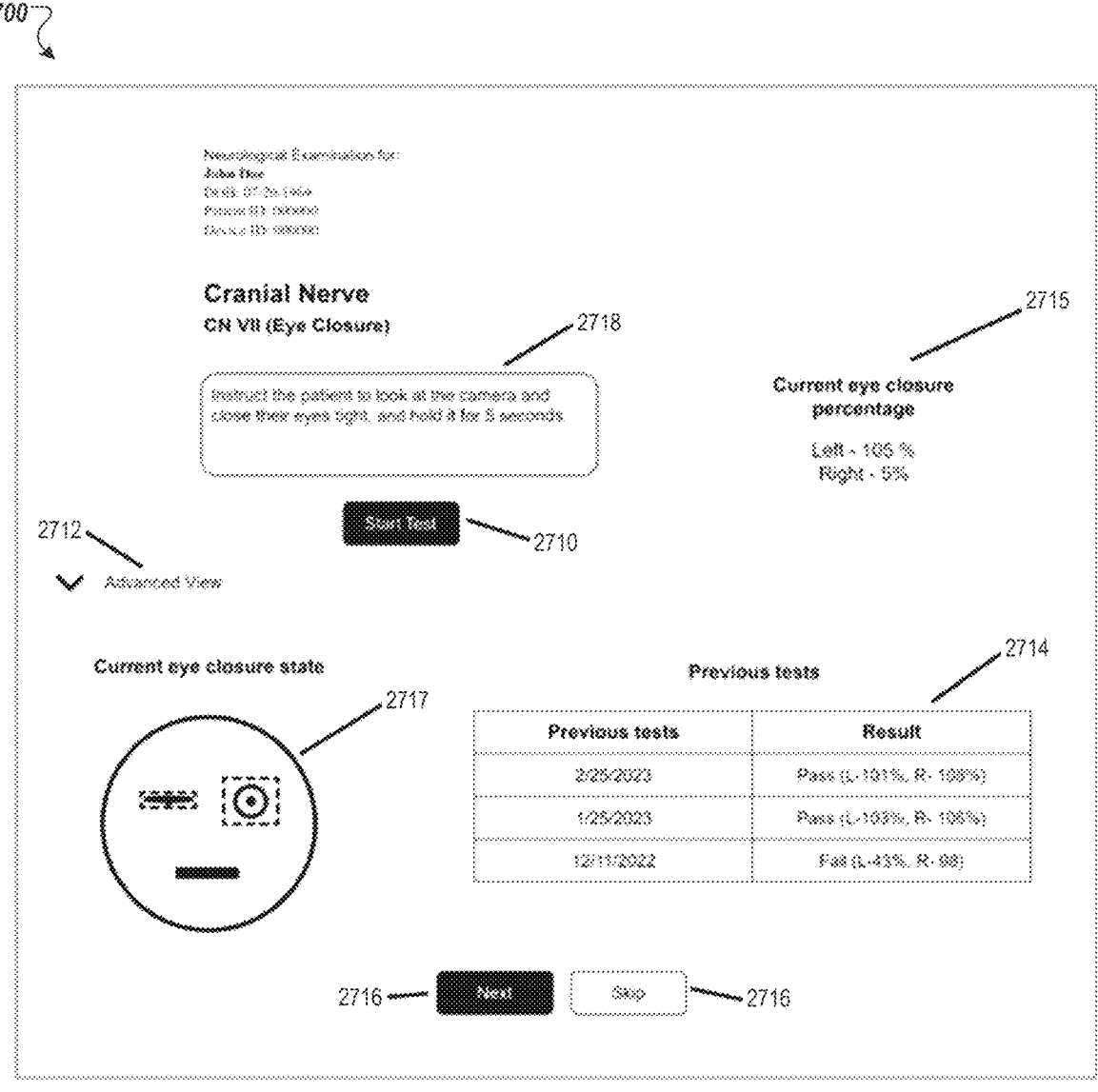

FIGS. 27A-C illustrate GUIs associated with conducting an eye closure examination, according to certain embodiments. FIG. 27A shows an operator view 2700 when the eye closure examination is conducted by someone other than a patient or an assistant of the patient. The operator view 2700 may include controls for each part of the test 2710, an ability to open advanced view 2712 with functions like previous test results 2714, current eye closure percentage for each eye 2715, controls to switch between tests 2716, current eye closure state 2717, and/or provider instructions 2718. FIG. 27B shows a patient view 2720 (e.g., displayed on the IO module) including instructions 2722 that will tell the patient what to do during the test. FIG. 27C shows the patient view 2720 when the test is conducted by the patient or the assistant of the patient, including instructions 2722 and/or controls to switch to the next test 2728.

Figure 28A:
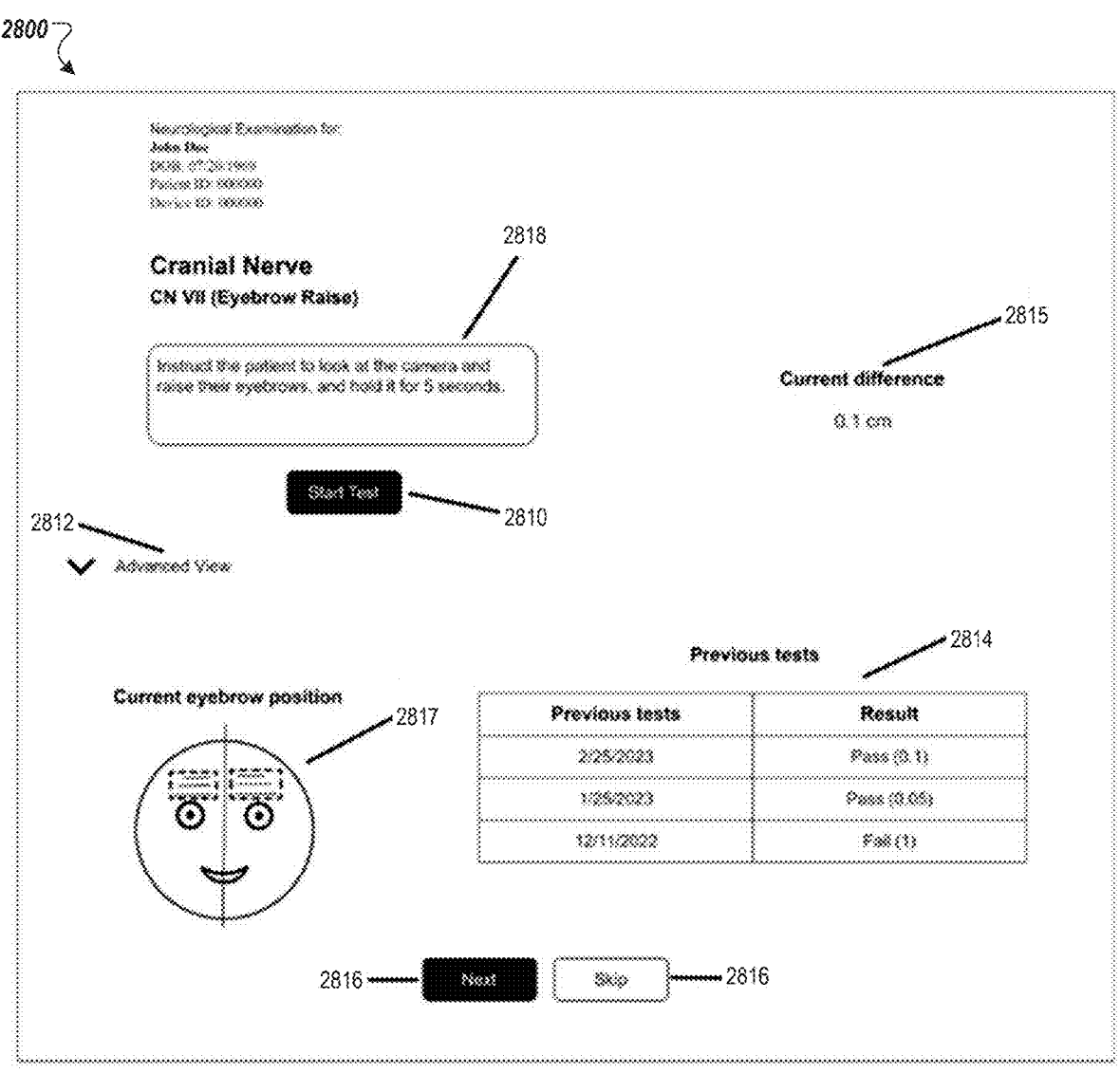
FIGS. 28A-C illustrate GUIs associated with conducting an eyebrow raise examination, according to certain embodiments.
Figure 28B:
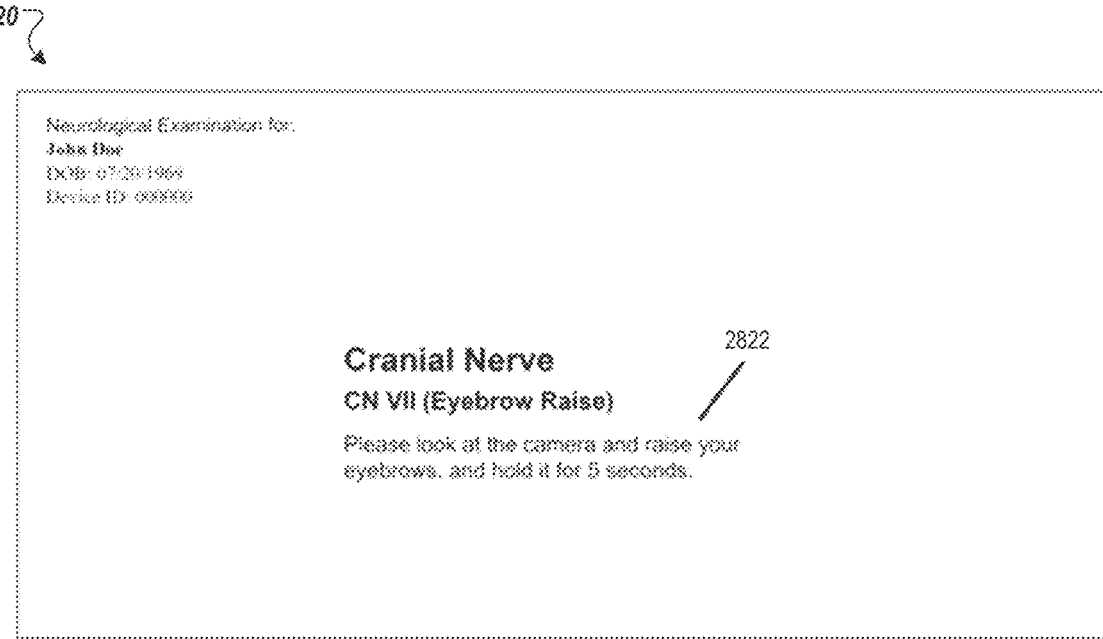
Figure 28C:
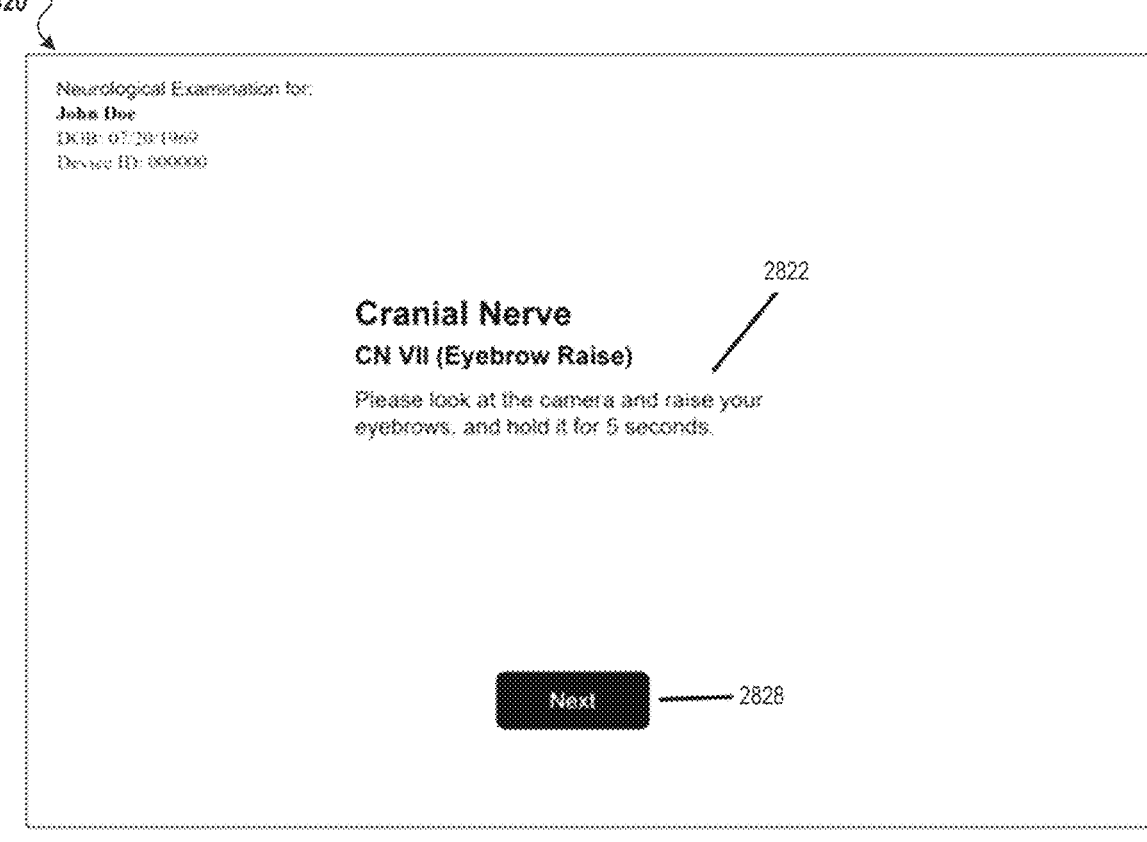

FIGS. 28A-C illustrate GUIs associated with conducting an eyebrow raise examination, according to certain embodiments. FIG. 28A shows an operator view 2800 when the eyebrow raise examination is conducted by someone other than a patient or an assistant of the patient. The operator view 2800 may include controls for each part of the test 2810, an ability to open advanced view 2812 with functions like previous test results 2814, current eyebrow height difference 2815, controls to switch between tests 2816, current eyebrow position 2817, and/or provider instructions 2818. FIG. 28B shows a patient view 2820 (e.g., displayed on the IO module) including instructions 2822 that will tell the patient what to do during the test. FIG. 28C shows the patient view 2820 when the test is conducted by the patient or the assistant of the patient, including instructions 2822 and/or controls to switch to the next test 2828.

Figure 29A:
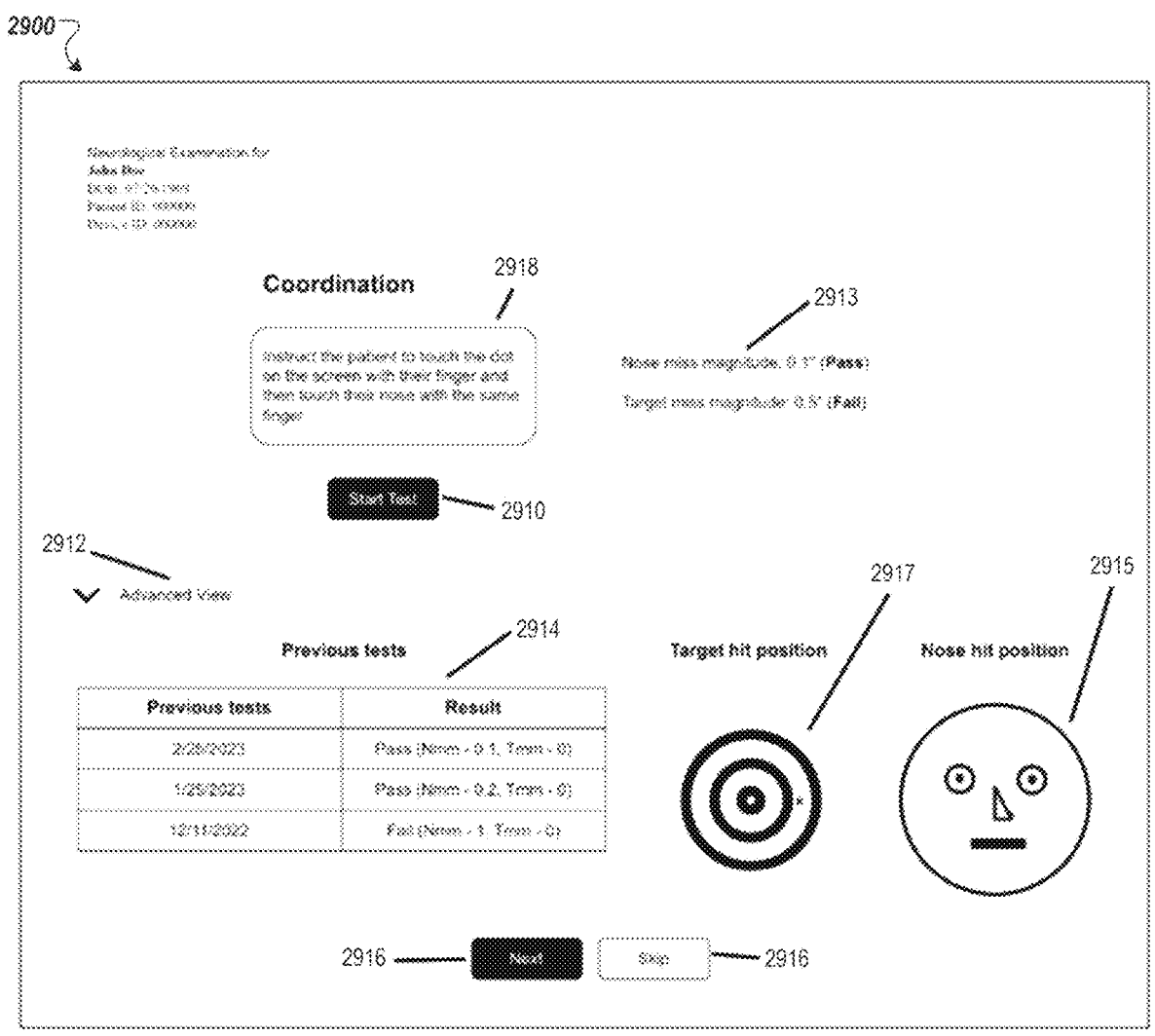
FIGS. 29A-C illustrate GUIs associated with conducting a coordination examination, according to certain embodiments.
Figure 29B:
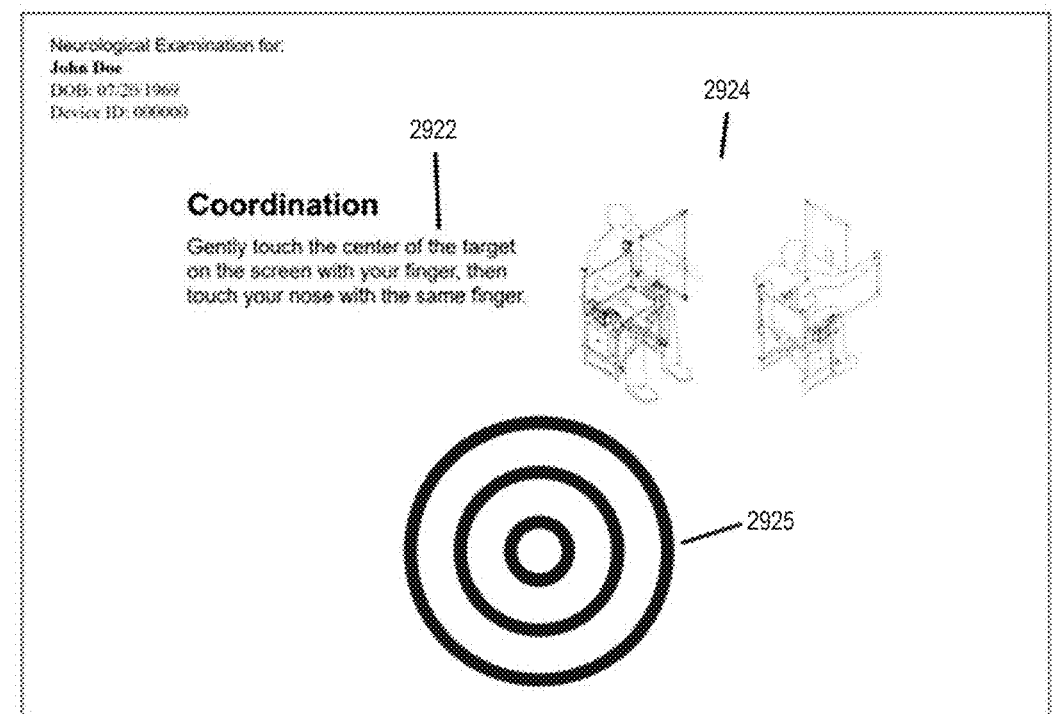
Figure 29C:
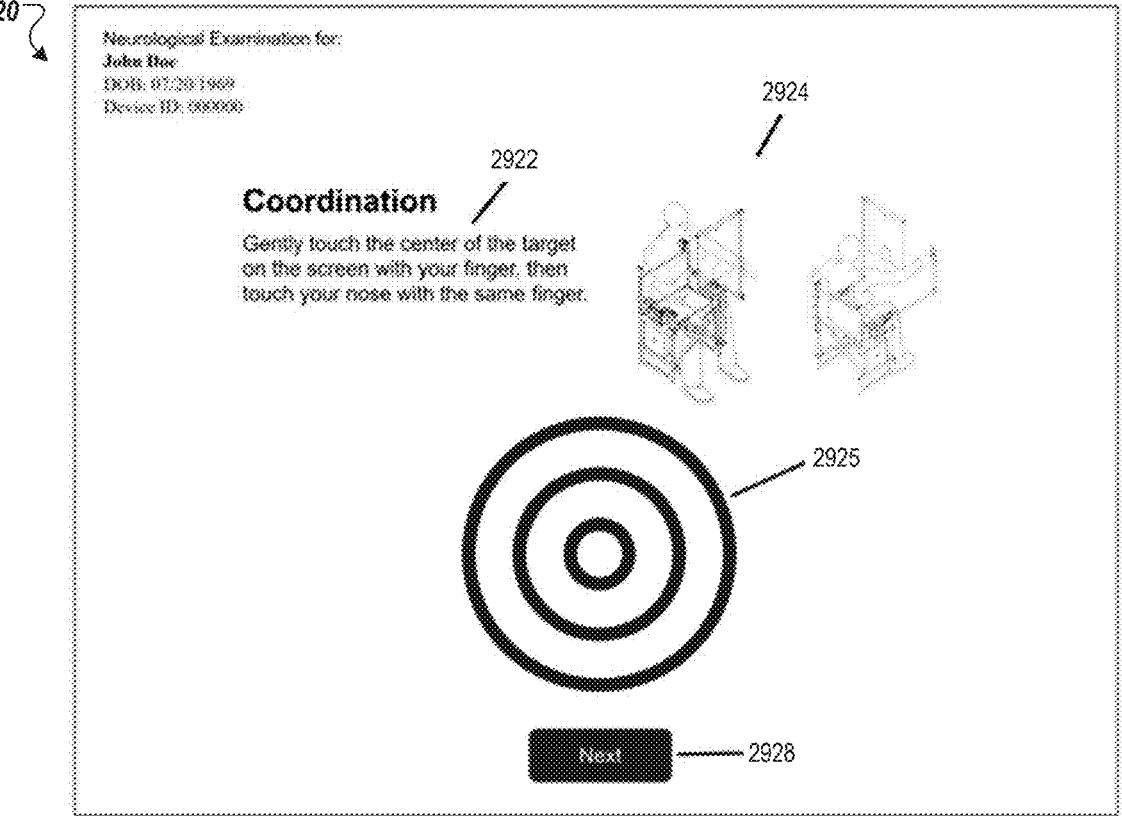

FIGS. 29A-C illustrate GUIs associated with conducting a coordination examination, according to certain embodiments. FIG. 29A shows an operator view 2900 when the coordination examination is conducted by someone other than a patient or an assistant of the patient. The operator view 2900 may include controls for each part of the test 2910, an ability to open advanced view 2912 with functions like previous test results 2914, miss magnitudes 2913, nose hit position 2915, controls to switch between tests 2916, target hit position 2917, and/or provider instructions 2918. FIG. 29B shows a patient view 2920 (e.g., displayed on the IO module) including instructions 2922, visual aids 2924, and/or a target 2925 for the patient to press that will tell the patient what to do during the test. FIG. 29C shows the patient view 2920 when the test is conducted by the patient or the assistant of the patient, including instructions 2922, visual aids 2924, the target 2925, and/or controls to switch to the next test 2928.

Figure 30A:
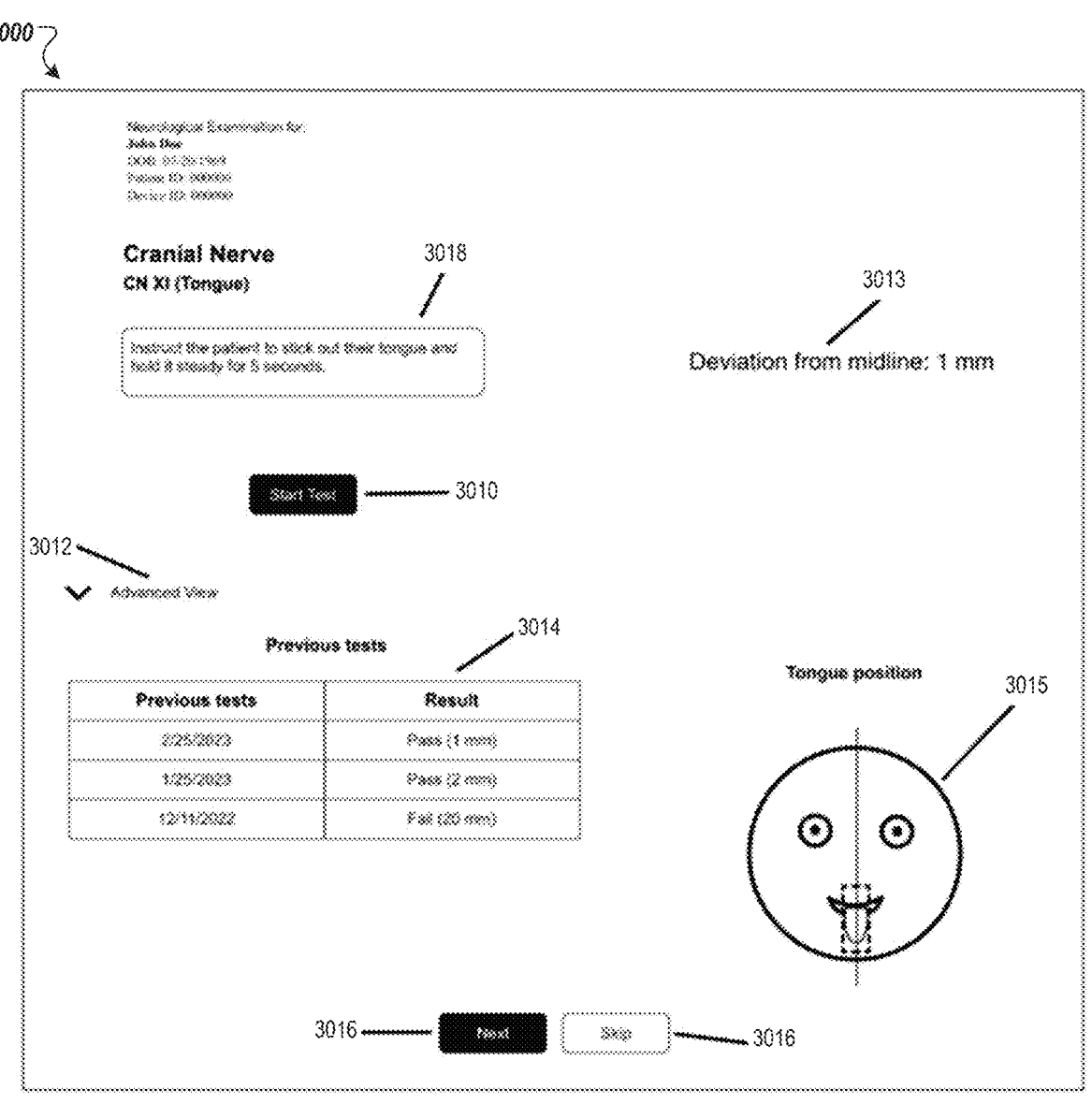
FIGS. 30A-C illustrate GUIs associated with conducting a tongue deviation examination, according to certain embodiments.
Figure 30B:
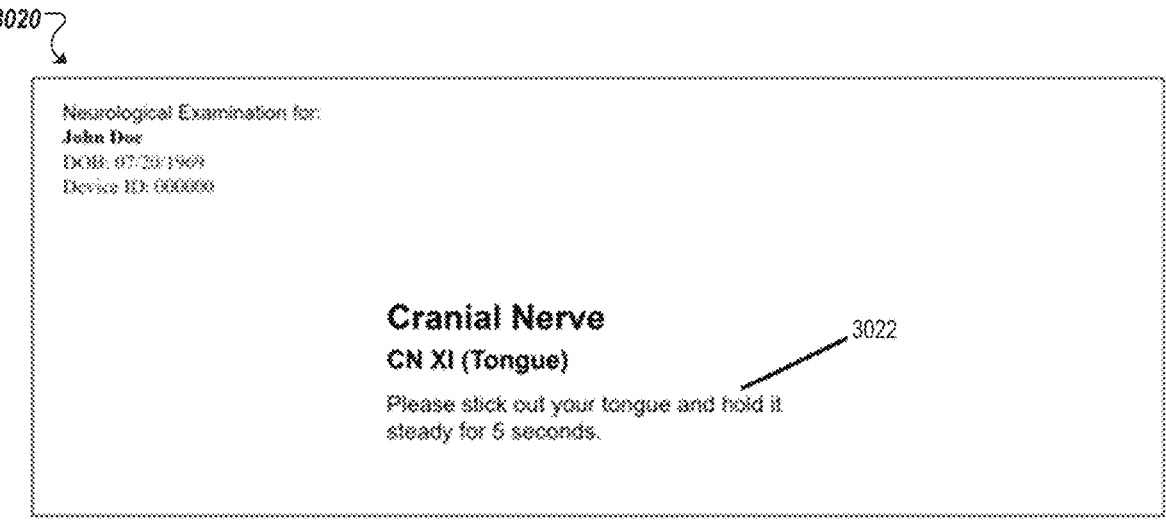
Figure 30C:
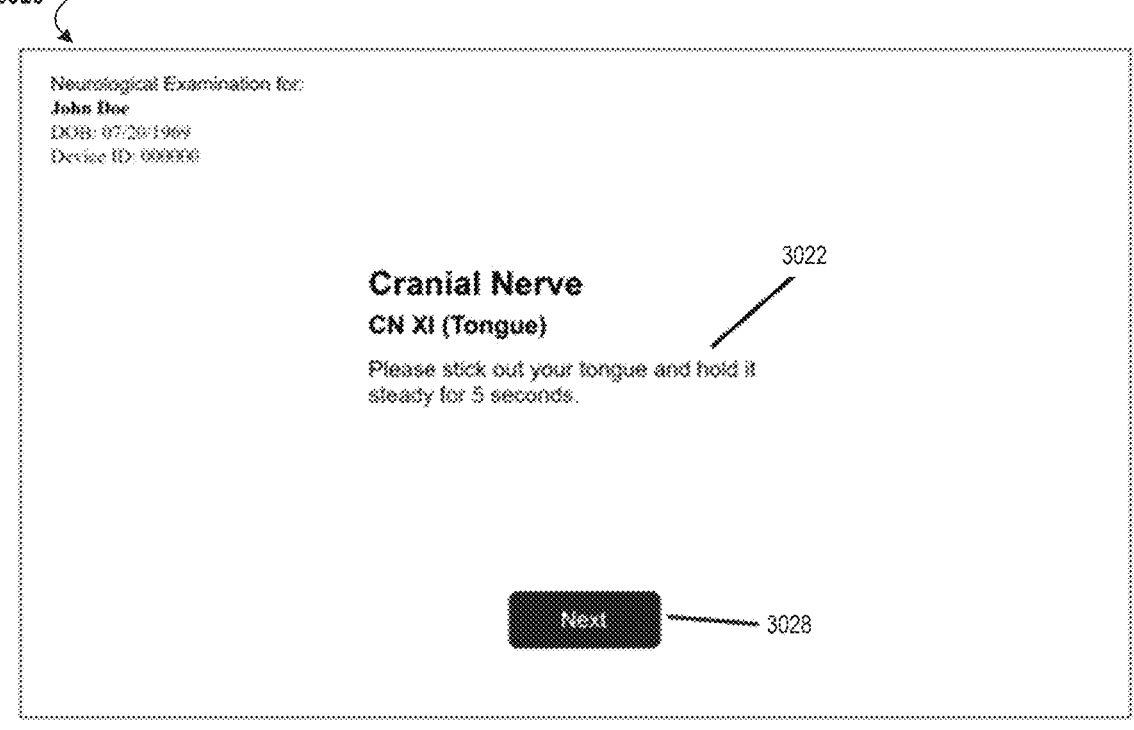

FIGS. 30A-C illustrate GUIs associated with conducting a tongue deviation examination, according to certain embodiments. FIG. 30A shows an operator view 3000 when the tongue deviation examination is conducted by someone other than a patient or an assistant of the patient. The operator view 3000 may include controls for each part of the test 3010, an ability to open advanced view 3012 with functions like previous test results 3014, deviation from midline 3013, tongue position 3015, controls to switch between tests 3016, and/or provider instructions 3018. FIG. 30B shows a patient view 3020 (e.g., displayed on the IO module) including instructions 3022 that will tell the patient what to do during the test. FIG. 30C shows the patient view 3020 when the test is conducted by the patient or the assistant of the patient, including instructions 3022 and/or controls to switch to the next test 3028.

Figure 31:
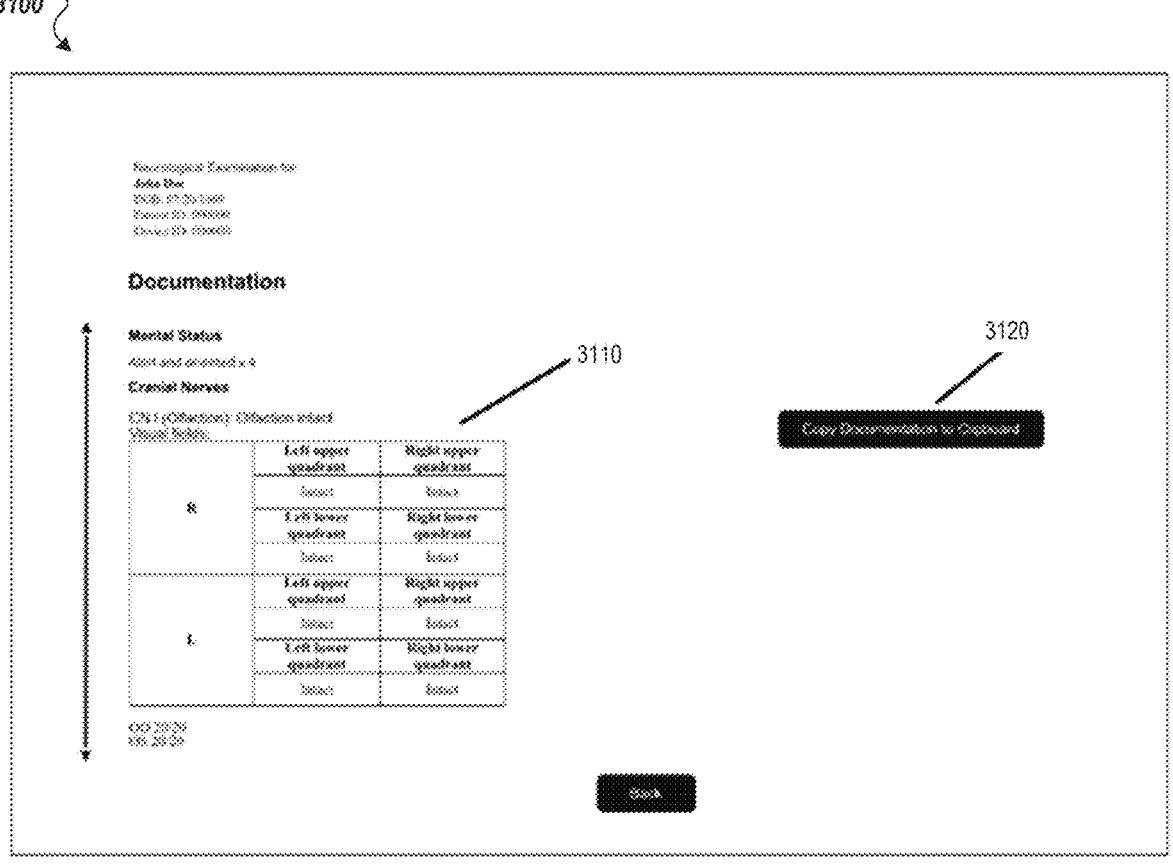
FIG. 31 illustrates a GUI associated with examination results, according to certain embodiments.

FIG. 31 illustrates a GUI associated with examination results 3100, according to certain embodiments. The GUI for examination results 3100 may provide one or more examination results in documentation format 3110, with functions such as copying the report to a clipboard 3120.

FIGS. 32A-C illustrate example computer vision techniques implemented by a processing device of the neurological examination system, according to certain embodiments.

In some embodiments, a processing device (e.g., executing an application) may employ computer vision techniques to analyze images and/or videos captured by a camera, such as a camera integrated into the ocular assessment module system 700 of FIG. 7, to facilitate aspects of neurological examinations. These aspects can include, but are not limited to, evaluating eye movement, assessing the smoothness of ocular pursuit, primary gaze, and/or pupillary reflex. Such evaluations may be conducted using a computer vision, machine learning, deep learning techniques and/or any combination of these techniques. To evaluate eye movement, smoothness of ocular pursuit, primary gaze, and pupillary reflex, the location of the pupils in a frame or series of frames must be identified. This can be achieved using various computer vision techniques that vary in complexity and accuracy.

In some embodiments Haar cascades can be used, which are cascades of classifiers that each learn to identify features like lines, edges, or rectangles. If a region of the frame contains the pattern sought by the initial stage of the cascade, it advances to further stages for more detailed checks. If not, the region is rejected, reducing computation time through early filtering. A Haar cascade-based approach for detecting pupil coordinates can be implemented using open-source software libraries like the open-source computer vision library (OpenCV). A face detection model, such as the Haar cascade model provided by OpenCV, the Histogram of Oriented Gradients+Linear Support Vector Machine-based face detector provided by Dlib, or a Convolutional Neural Network-based face detector like Blaze-Face (from Google Research, available in the open-source MediaPipe framework), can be used to determine if a face is in the frame. If a face is detected, the region of the frame (e.g., a bounding box 3210) containing the face is identified, as seen in FIG. 32A. That region of interest 3220 is then cropped and provided to the Haar cascade trained to detect a feature such as eyes (as seen in FIG. 32B), such as the pretrained model provided by OpenCV. Alternatively, with some loss of performance and accuracy, the eye detection Haar cascade can be applied directly to the image to detect eye regions, bypassing the face detection step. Once the eye region is detected, binary thresholding, contour detection, and other primitive computer vision techniques can be applied to isolate and detect the pupil's location.

Some embodiments employ a facial landmarking model. Facial landmarks 3230 are specific key points on the face, such as points along the eyes, nose, and mouth, which serve as reference points for analyzing facial features. Each landmark is associated with a specific index; for example, the left edge of the lip is represented by index 28 and the right pupil by index 7 in FIG. 32C. These landmarks can be used to track the coordinates of specific features over time. Facial landmarking models can have varied architectures, such as the openly available pretrained Ensemble of Regression Trees model provided by Dlib, which identifies 68 landmarks, or the openly available neural network-based landmarking model BlazeFace Mesh from Google Research, available in the MediaPipe framework, which identifies 473 landmarks. As described above, a face detection model may first be used to identify the region of interest (the face) and its associated bounding box (as seen in FIG. 32B). Then, the cropped image of the face, or in some instances the uncropped image, is provided to a facial landmarking model.

If the landmarking model contains landmarks for the pupil, as in the case of the BlazeFace Mesh, those landmarks can be directly used, whereas if the landmarking model only provides landmarks for regions of the eye other primitive computer vision techniques can be applied to isolate and detect the pupil's location.

Using these techniques, the position and/or size of each pupil can be identified in every frame or at intervals across multiple frames, generating a series of coordinates representing the pupil's location and/or size over time. The change in these coordinates is then analyzed to evaluate eye movement, the smoothness and variance of ocular pursuit, the intactness of primary gaze, and pupil size.

In some embodiments, the processing device (e.g., executing an application, the computational module, etc.) utilizes computational algorithms to analyze images and/or videos captured by the camera (e.g., the camera 740 of the ocular assessment module system 700 of FIG. 7) to assist in various components of a neurological examination, such as assessing smile symmetry, tongue deviation, eyebrow raising, and eyelid closure ability. These assessments are performed by identifying and analyzing facial landmarks using the techniques previously described.

The abovementioned techniques can be used in conjunction with the camera 740 of FIG. 7 for smile symmetry assessment and facial droop detection. The patient is instructed to smile. Key landmarks around the mouth and face are identified (such as indices 13-33 in FIG. 32C), and the degree of droop can be calculated by measuring the vertical differences between these landmarks. To evaluate tongue deviation, the patient is asked to stick out their tongue. The processing device detects key landmarks of the mouth, face, and midline of the tongue, potential using a custom classifier, computing deviation or bias toward one side of the mouth based on these coordinates. For eyebrow asymmetry assessment, the patient is instructed to raise their eyebrows. Key landmarks on the eyebrows and forehead (such as indices 35-45 and 46-59, respectively, in FIG. 32C) are detected, and asymmetry is quantified by calculating vertical differences between corresponding landmarks on each side of the face. For evaluating eyelid closure, the patient is asked to close their eyelids. The processing device identifies landmarks corresponding to the upper and lower eyelids (such as indices 1-10 in FIG. 32C) and determines whether the eyelids are fully closed based on the distance between these landmarks. For coordination assessment, the patient is instructed to press a target displayed on the screen (e.g., a screen in the IO module) and then touch their nose with the same finger. The distance between the fingertip, as identified by a custom classifier, and facial landmarks around the nose are computed to determine if the patient accurately touches the nose or to measure the extent of any deviation.

In some embodiments, the information gathered through the above mentioned techniques and processes correspond to the set of assessment data associated with respective assessment module devices of the neurological examination system. Various sets of assessment data may be gathered when a patient is positioned in the patient placement module and uses one or more of the assessment module devices attached to the patient placement module via one or more arms. The processing device used to gather and/or analyze the various sets of assessment data may be part of the neurological examination system and/or a processing device of a user device (e.g., executing an application). The processing device may determine assessment outcome data based on the various sets of assessment data, and provide the assessment outcome data to the user device.

Figure 33:
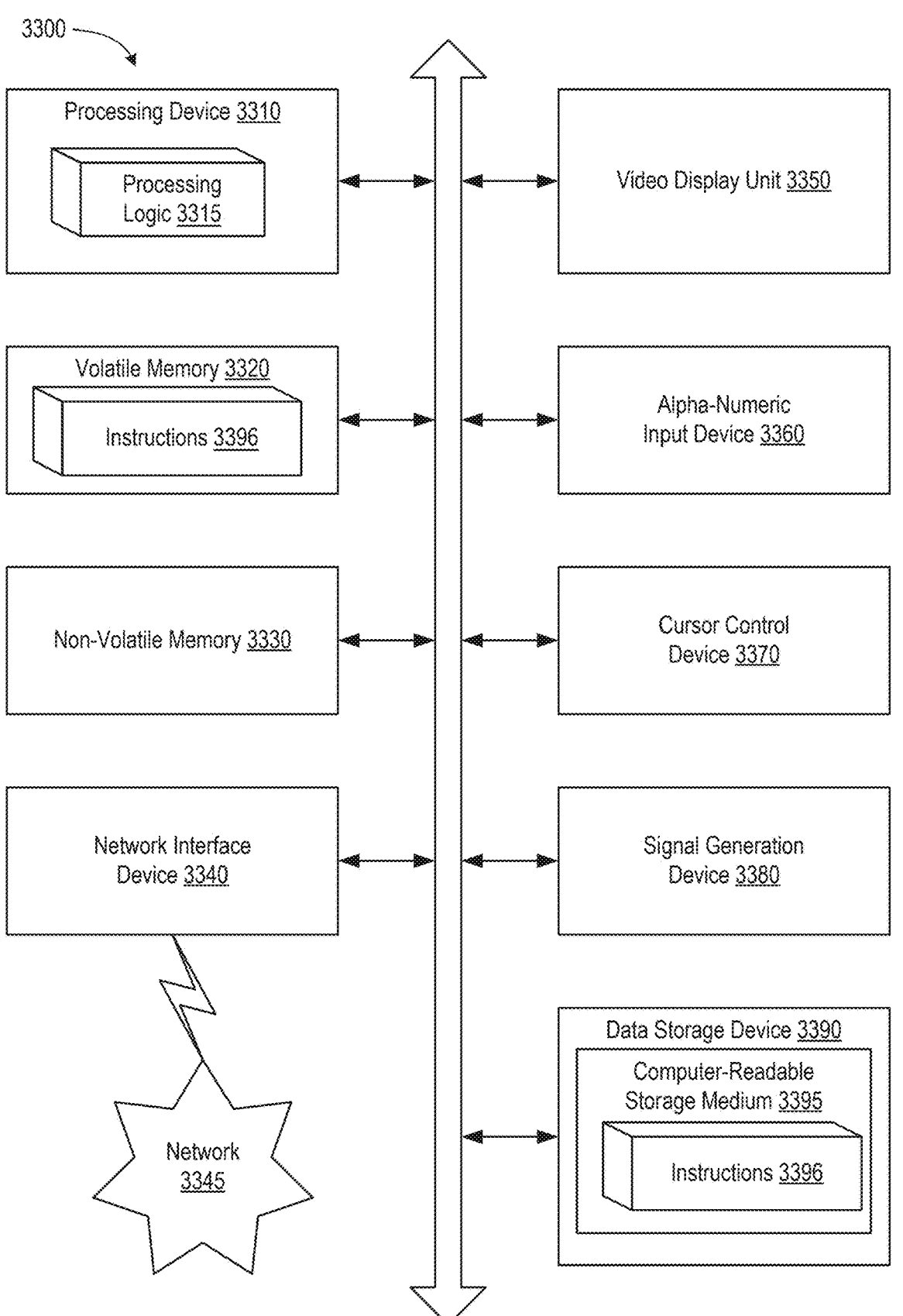
FIG. 33 is a block diagram illustrating an example computer system according to certain embodiments.

FIG. 33 is a block diagram illustrating an example computer system 3300 according to certain embodiments. In some embodiments, computer system 3300 is connected (e.g., via a network, such as a Local Area Network (LAN), an intranet, an extranet, or the Internet) to other computer systems. In some embodiments, computer system 3300 operates in the capacity of a server or a client computer in a client-server environment, or as a peer computer in a peer-to-peer or distributed network environment. In some embodiments, computer system 3300 is provided by a personal computer (PC), a tablet PC, a Set-Top Box (STB), a Personal Digital Assistant (PDA), a cellular telephone, a web appliance, a server, a network router, switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein.

In a further aspect, the computer system 3300 includes a processing device 3310 (e.g., the processing device 140 of FIG. 1, the processing device of a user device, the computational module 1110 of FIG. 11A, etc.), a volatile memory 3320 (e.g., Random Access Memory (RAM)), a non-volatile memory 3330 (e.g., Read-Only Memory (ROM) or Electrically-Erasable Programmable ROM (EEPROM)), and a data storage device 3390, which communicate with each other via a bus.

In some embodiments, processing device 3310 is provided by one or more processors such as a general purpose processor (such as, for example, a Complex Instruction Set Computing (CISC) microprocessor, a Reduced Instruction Set Computing (RISC) microprocessor, a Very Long Instruction Word (VLIW) microprocessor, a microprocessor implementing other types of instruction sets, or a microprocessor implementing a combination of types of instruction sets) or a specialized processor (such as, for example, an Application Specific Integrated Circuit (ASIC), a Field Programmable Gate Array (FPGA), a Digital Signal Processor (DSP), or a network processor).

In some embodiments, computer system 3300 further includes a network interface device 3340 (e.g., coupled to network 3345). In some embodiments, computer system 3300 also includes a video display unit 3350 (e.g., an LCD), an alphanumeric input device 3360 (e.g., a keyboard), a cursor control device 3370 (e.g., a mouse), and a signal generation device 3380.

In some implementations, data storage device 3390 includes a non-transitory computer-readable storage medium 3395 on which store instructions 3396 encoding any one or more of the methods or functions described herein, including instructions for implementing methods described herein.

In some embodiments, instructions 3396 also reside, completely or partially, within volatile memory 3320 and/or within processing device 3310 during execution thereof by computer system 3300, hence, in some embodiments, volatile memory 3320 and processing device 3310 also constitute machine-readable storage media.

While computer-readable storage medium 3395 is shown in the illustrative examples as a single medium, the term "computer-readable storage medium" shall include a single medium or multiple media (e.g., a centralized or distributed database, and/or associated caches and servers) that store the one or more sets of executable instructions. The term "computer-readable storage medium" shall also include any tangible medium that is capable of storing or encoding a set of instructions for execution by a computer that cause the computer to perform any one or more of the methods described herein. The term "computer-readable storage medium" shall include, but not be limited to, solid-state memories, optical media, and magnetic media.

The above listed embodiments do not universally encompass the final forms that a neurological examination system may take. Other iterations may include the inclusion of additional strength assessment module devices throughout the system to perform additional tests based on various movements of the head, neck, back, arms, hands, hips, legs, and feet.

In some embodiments, the methods, components, and features described herein are implemented by discrete hardware components or are integrated in the functionality of other hardware components such as ASICS, FPGAs, DSPs or similar devices. In some embodiments, the methods, components, and features are implemented by firmware modules or functional circuitry within hardware devices. In some embodiments, the methods, components, and features are implemented in any combination of hardware devices and computer program components, or in computer programs.

Unless specifically stated otherwise, terms such as "identifying," "receiving," "causing," "generating," "providing," "obtaining," "determining," "transmitting," or the like, refer to actions and processes performed or implemented by computer systems that manipulates and transforms data represented as physical (electronic) quantities within the computer system registers and memories into other data similarly represented as physical quantities within the computer system memories or registers or other such information storage, transmission or display devices. In some embodiments, the terms "first," "second," "third," "fourth," etc. as used herein are meant as labels to distinguish among different elements and do not have an ordinal meaning according to their numerical designation.

Examples described herein also relate to an apparatus for performing the methods described herein. In some embodiments, this apparatus is specially constructed for performing the methods described herein or includes a general-purpose computer system selectively programmed by a computer program stored in the computer system. Such a computer program is stored in a computer-readable tangible storage medium.

Some of the methods and illustrative examples described herein are not inherently related to any particular computer or other apparatus. In some embodiments, various general-purpose systems are used in accordance with the teachings described herein. In some embodiments, a more specialized apparatus is constructed to perform methods described herein and/or each of their individual functions, routines, subroutines, or operations. Examples of the structure for a variety of these systems are set forth in the description above.

The above description is intended to be illustrative, and not restrictive. Although the present disclosure has been described with references to specific illustrative examples and implementations, it will be recognized that the present disclosure is not limited to the examples and implementations described. The scope of the disclosure should be determined with reference to the following claims, along with the full scope of equivalents to which the claims are entitled.

The preceding description sets forth numerous specific details such as examples of specific systems, components, methods, and so forth in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular implementations may vary from these exemplary details and still be contemplated to be within the scope of the present disclosure.

The terms "over," "under," "between," "disposed on," and "on" as used herein refer to a relative position of one material layer or component with respect to other layers or components. For example, one layer disposed on, over, or under another layer may be directly in contact with the other layer or may have one or more intervening layers. Moreover, one layer disposed between two layers may be directly in contact with the two layers or may have one or more intervening layers. Similarly, unless explicitly stated otherwise, one feature disposed between two features may be in direct contact with the adjacent features or may have one or more intervening layers.

The words "example" or "exemplary" are used herein to mean serving as an example, instance or illustration. Any aspect or design described herein as "example" or "exemplary" is not necessarily to be construed as preferred or advantageous over other aspects or designs. Rather, use of the words "example" or "exemplary" is intended to present concepts in a concrete fashion.

Reference throughout this specification to "one embodiment," "an embodiment," or "some embodiments" means that a particular feature, structure, or characteristic described in connection with the embodiment is included in at least one embodiment. Thus, the appearances of the phrase "in one embodiment," "in an embodiment," or "in some embodiments" in various places throughout this specification are not necessarily all referring to the same embodiment. In addition, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Also, the terms "first," "second," "third," "fourth," etc. as used herein are meant as labels to distinguish among different elements and can not necessarily have an ordinal meaning according to their numerical designation. When the term "about," "substantially," or "approximately" is used herein, this is intended to mean that the nominal value presented is precise within ±2%, ±5%, ±7%, ±10%, ±12%, ±15%, ±17%, or ±20%.

Although the operations of the methods herein are shown and described in a particular order, the order of operations of each method may be altered so that certain operations may be performed in an inverse order so that certain operations may be performed, at least in part, concurrently with other operations. In another embodiment, instructions or sub-operations of distinct operations may be in an intermittent and/or alternating manner.

It is understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled. While certain embodiments have been described and shown in the accompanying drawings, it is to be understood that such embodiments are merely illustrative of and not restrictive on the present disclosure, and that this present disclosure is not be limited to the specific constructions and arrangements shown and described, since various other modifications may occur to those ordinarily skilled in the art.

What is claimed is:

1. A system comprising:

a patient placement module configured to receive a patient;

a plurality of arms connected to the patient placement module;

a strength assessment module device connected to a first arm of the plurality of arms, wherein the strength assessment module device is configured to provide a set of strength assessment data associated with a neurological examination of the patient; and a stereognosis assessment module device connected to a second arm of the plurality of arms, wherein the stereognosis assessment module device is configured to provide a set of tactile sensory interpretation assessment data associated with the neurological examination of the patient, and wherein the stereognosis assessment module device comprises:

a first structure configured to store a first physical object and a second structure configured to store a second physical object, wherein the first structure comprises a first input door and a first output door and the second structure comprises a second input door and a second output door;

an input funnel coupled to the first structure and the second structure, wherein the first structure is separated from the input funnel by the first input door and the second structure is separated from the input funnel by the second input door;

an output funnel coupled to the first structure and the second structure, wherein the first structure is separated from the output funnel by the first output door and the second structure is separated from the output funnel by the second output door; and a pickup area configured to receive the first physical object responsive to the first output door moving from a first position to a second position or the second physical object responsive to the second output door moving from the first position to the second position, wherein the moving from the first position to the second position is responsive to actuation of the stereognosis assessment module device by the patient or a user.

2. The system of claim 1, wherein the strength assessment module device comprises a force sensor configured to provide the set of strength assessment data, wherein the set of strength assessment data is associated with a force applied by the patient to the strength assessment module device.

3. The system of claim 2, wherein the strength assessment module device further comprises:

an inflatable bag coupled to the force sensor, wherein the force sensor is configured to measure the force applied by the patient to the inflatable bag; and

a pump coupled to the inflatable bag, wherein the pump is configured to inflate the inflatable bag.

4. The system of claim 1, further comprising a sensory assessment module device connected to the patient placement module, wherein the sensory assessment module device is configured to provide a set of sensory assessment data associated with the neurological examination of the patient, the set of sensory assessment data corresponding to at least one of pain sensation of the patient, temperature sensation of the patient, or vibration sensation of the patient.

5. The system of claim 4, wherein the sensory assessment module device comprises:

a vibration component configured to provide a vibration to the patient; and a heating component configured to provide a temperature to the patient.

6. The system of claim 4, further comprising an ocular assessment module device connected to the patient placement module, wherein the ocular assessment module device is configured to provide a set of visual assessment data associated with the neurological examination of the patient.

7. The system of claim 6, wherein the ocular assessment module device comprises:

a display device configured to present visual stimuli; and a camera configured to provide image data associated with an eye movement of the patient associated with the visual stimuli.

8. The system of claim 6, further comprising an auditory assessment module device connected to the patient placement module, wherein the auditory assessment module device is configured to provide a set of auditory assessment data associated with the neurological examination of the patient, wherein the set of auditory assessment data is associated with vestibulocochlear nerve function of the patient.

9. The system of claim 8, wherein the auditory assessment module device comprises at least one of:

a speaker component configured to provide sound to the patient; or a vibration component comprising a vibration generator and one or more vibration stems configured to provide vibration to the patient.

10. The system of claim 8, further comprising an olfactory assessment module device connected to the patient placement module, wherein the olfactory assessment module device is configured to provide a set of olfactory assessment data associated with the neurological examination of the patient.

11. The system of claim 10, wherein the olfactory assessment module device comprises:

a fan configured to blow air;

a set of tubes comprising one or more scented materials, each of the one or more scented materials associated with a respective scent of a plurality of different scents; and controllable gates configured to provide the respective scent to the patient responsive to the fan blowing air through the set of tubes.

12. The system of claim 1, wherein the plurality of arms are movable between a corresponding first position and a corresponding second position, wherein the corresponding first position is an operational position adjustable to the patient and is associated with providing a respective set of assessment data, and wherein the corresponding second position is a stowed position and is not associated with providing the respective set of assessment data.

13. The system of claim 1, wherein the first arm is configured to position the strength assessment module device into different areas around the patient to assess at least two muscle groups of the patient.

14. The system of claim 13, wherein the at least two muscle groups are associated with at least two or more of:
 a hand;
 a foot;
 an ankle;
 a knee;
 a thigh;
 a hip;
 a wrist;
 an elbow;
 a shoulder; or
 a head of the patient.

15. A system comprising:
 a patient placement module configured to receive a patient;
 a plurality of arms connected to the patient placement module;
 a strength assessment module device connected to a first arm of the plurality of arms, wherein the strength assessment module device is configured to provide strength assessment data associated with a neurological examination of the patient;
 a sensory assessment module device connected to the patient placement module via a second arm of the plurality of arms, wherein the sensory assessment module device is configured to provide a set of sensory assessment data associated with the neurological examination of the patient; and
 a stereognosis assessment module device connected to the patient placement module via a third arm of the plurality of arms, wherein the stereognosis assessment module device is configured to provide a set of tactile sensory interpretation assessment data associated with the neurological examination of the patient, and wherein the stereognosis assessment module device comprises:
  a first structure configured to store a first physical object and a second structure configured to store a second physical object, wherein the first structure comprises a first input door and a first output door and the second structure comprises a second input door and a second output door;
  an input funnel coupled to the first structure and the second structure, wherein the first structure is separated from the input funnel by the first input door and the second structure is separated from the input funnel by the second input door;
  an output funnel coupled to the first structure and the second structure, wherein the first structure is separated from the output funnel by the first output door and the second structure is separated from the output funnel by the second output door; and
  a pickup area configured to receive the first physical object responsive to the first output door moving from a first position to a second position or the second physical object responsive to the second output door moving from the first position to the second position, wherein the moving from the first position to the second position is responsive to actuation of the stereognosis assessment module device by the patient or a user.

16. The system of claim 15 further comprising an ocular assessment module device connected to the patient placement module, wherein the ocular assessment module device is configured to provide a set of ocular assessment data associated with the neurological examination of the patient.

17. The system of claim 16 further comprising at least one of:
 an auditory assessment module device configured to provide a set of auditory assessment data associated with vestibulocochlear nerve function of the patient; or
 an olfactory assessment module device configured to provide a set of olfactory assessment data associated with olfaction of the patient.

18. A system comprising:
 a patient placement module configured to receive a patient;
 a plurality of arms connected to the patient placement module;
 a strength assessment module device connected to a first arm of the plurality of arms, wherein the strength assessment module device is configured to provide a set of strength assessment data associated with a neurological examination of the patient;
 a stereognosis assessment module device connected to a second arm of the plurality of arms, wherein the stereognosis assessment module device is configured to provide a set of tactile sensory interpretation assessment data associated with the neurological examination of the patient, and wherein the stereognosis assessment module device comprises:
  a first structure configured to store a first physical object and a second structure configured to store a second physical object, wherein the first structure comprises a first input door and a first output door and the second structure comprises a second input door and a second output door;
  an input funnel coupled to the first structure and the second structure, wherein the first structure is separated from the input funnel by the first input door and the second structure is separated from the input funnel by the second input door;
  an output funnel coupled to the first structure and the second structure, wherein the first structure is separated from the output funnel by the first output door and the second structure is separated from the output funnel by the second output door; and
  a pickup area configured to receive the first physical object responsive to the first output door moving from a first position to a second position or the second physical object responsive to the second output door moving from the first position to the second position, wherein the moving from the first position to the second position is responsive to actuation of the stereognosis assessment module device by the patient or a user; and
 a processing device connected to at least one of the strength assessment module device, the stereognosis assessment module device, or the patient placement module, the processing device to:
  receive, from the strength assessment module device, the set of strength assessment data;
  determine, based on the set of strength assessment data, strength assessment outcome data;
  receive, from the stereognosis assessment module device, the set of tactile sensory interpretation assessment data;
  determine, based on the set of tactile sensory interpretation assessment data, tactile sensory interpretation assessment outcome data; and provide at least one of the strength assessment outcome data or the tactile sensory interpretation assessment outcome data to a user device.

19. The system of claim 18, further comprising:

a sensory assessment module device connected to the patient placement module, wherein the sensory assessment module device is configured to provide a set of sensory assessment data associated with the neurological examination of the patient; and an ocular assessment module device connected to the patient placement module, wherein the ocular assessment module device is configured to provide a set of ocular assessment data associated with the neurological examination of the patient.

20. The system of claim 19, wherein the processing device is further to:

receive, from the sensory assessment module device, the set of sensory assessment data;

determine, based on the set of sensory assessment data, sensory assessment outcome data;

receive, from the ocular assessment module device, the set of ocular assessment data;

determine, based on the set of ocular assessment data, ocular assessment outcome data; and provide at least one of the sensory assessment outcome data or the ocular assessment outcome data to the user device.

\* \* \* \* \*